United States Patent
Boulos

(10) Patent No.: US 11,591,323 B2
(45) Date of Patent: Feb. 28, 2023

(54) MUSCARINIC AGONISTS AS NON-STEROIDAL AND NON-OPIOID ANALGESICS AND METHODS OF USE THEREOF

(71) Applicant: Barry University, Miami Shores, FL (US)

(72) Inventor: John Boulos, Miami Lakes, FL (US)

(73) Assignee: BARRY UNIVERSITY, Miami Shores, FL (US)

( * ) Notice: Subject to any disclaimer, the term of this patent is extended or adjusted under 35 U.S.C. 154(b) by 0 days.

(21) Appl. No.: 16/809,851

(22) Filed: Mar. 5, 2020

(65) Prior Publication Data

US 2020/0283427 A1 Sep. 10, 2020

Related U.S. Application Data

(60) Provisional application No. 62/814,367, filed on Mar. 6, 2019.

(51) Int. Cl.
| | | |
|---|---|---|
| *C07D 409/06* | (2006.01) | |
| *C07D 413/06* | (2006.01) | |
| *C07D 471/08* | (2006.01) | |
| *A61K 9/00* | (2006.01) | |

(52) U.S. Cl.
CPC ......... *C07D 413/06* (2013.01); *C07D 409/06* (2013.01); *C07D 471/08* (2013.01); *A61K 9/0029* (2013.01); *A61K 9/0053* (2013.01)

(58) Field of Classification Search
CPC .......................... A61K 31/4535; C07D 409/06
USPC .......................................... 514/326; 546/212
See application file for complete search history.

(56) References Cited

U.S. PATENT DOCUMENTS

| | | |
|---|---|---|
| 9,156,833 B2 | 10/2015 | Boulos |
| 9,629,833 B2 | 4/2017 | Boulos |
| 9,662,318 B2 | 5/2017 | Boulos |

OTHER PUBLICATIONS

"Novel M2-selective, Gi-biased agonists of muscarinic acetylcholine receptors." British Journal of Pharmacology. Randakova, Alena & Nelic, Dominik & Ungerová, Dana & Nwokoye, Peter & Su, Qiwen & Dolezal, Vladimír & El-Fakahany, Esam & Boulos, John & Jakubik, Jan. (2020). 177. 10.1111/bph.14970.

"Agonist-Specific Conformations of the M2 Muscarinic Acetylcholine Receptor Assessed by Molecular Dynamics" Alena Randáková, Dominik Nelic, Vladimír Doležal, Esam E. El-Fakahany, John Boulos, and Jan Jakubík, Journal of Chemical Information and Modeling 2020 60 (4), 2325-2338, DOI: 10.1021/acs.jcim.0c00041.

"Applications and limitations of fitting of the operational model to determine relative efficacies of agonists." Jakubik, J., Randáková, A., Rudajev, V. et al., Sci Rep 9, 4637 (2019). https://doi.org/10.1038/s41598-019-40993-w.

"Synthesis of N-Substituted Piperidine Salts as Potential Muscarinic Ligands for Alzheimer's Applications" John Boulos, Jan Jakubik, Alena Randakova, Cristina Avila—First published Wiley Online Library (wileyonlinelibrary.com): Sep. 12, 2013.

*Primary Examiner* — Jeffrey H Murray
(74) *Attorney, Agent, or Firm* — Fox Rothschild LLP

(57) ABSTRACT

Novel Gi/o-biased muscarinic agonists selectively activate only one specific signaling pathway and are novel pharmacophores for development of new painkillers (analgesics). Methods of making and using these agonists are also described. The muscarinic agonists are of the formula:

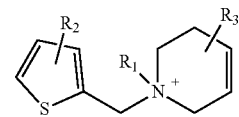

or an analog, derivative or pharmaceutically acceptable salt thereof, wherein:

$R_1$=H or Me; $R_2$=H, Me, Et, OMe, OEt, F, Cl, Br, I, or $NO_2$; and $R_3$=H, Me, Et, OMe, or $CO_2Me$ ($R_3$ may be bonded to any carbon of the rings).

5 Claims, 16 Drawing Sheets

Compounds 6

Compounds 8

Compounds 9

Compounds 10

MUSCARINIC AGONISTS AS NON-STEROIDAL AND NON-OPIOID ANALGESICS AND METHODS OF USE THEREOF

CROSS-REFERENCE TO RELATED APPLICATION

This application claims priority to U.S. Provisional Application No. 62/814,367 filed Mar. 6, 2019, which is herein incorporated by reference in its entirety.

FIELD OF THE INVENTION

The invention relates generally to the fields of pharmacology, medicine, and neurochemistry. In particular, the invention relates to synthesis and use of novel non-steroidal and non-opioid muscarinic agonist compounds as analgesics.

BACKGROUND

Opioid overdose is a national crisis that affects thousands of Americans every year. Not only it is a public health crisis but an economic burden to the healthcare system and to many families. Opioids, prescribed as pain relievers, are highly addictive with multiple adverse side effects. Therefore, it is of great importance for the science community to develop alternative drug therapies, to reduce or eliminate the use of opioids as painkillers, with lower or no side effects.

SUMMARY

A novel approach to drug therapy is to target $M_2$ and $M_4$ muscarinic receptors with selective agonists serving as analgesics for alleviating pain after surgery, dental work, cancer treatment or other conditions. G-protein-coupled receptors (GPCRs) represent a large protein family responsible for mediating extracellular to intracellular signaling. They are located in the plasma membrane of all cell types of various tissues and are involved in the control of numerous central and peripheral physiological responses, as well as being a major drug target in human disease. This family of receptors consists of muscarinic receptors designated as $M_1$-$M_5$. Activation of $M_2$ and $M_4$ receptors results in the coupling to the Gi/o family of G proteins, inhibition of adenylate cyclase, reduction in cAMP and a decrease in neurotransmitter release. Activation of $M_1$, $M_3$ and $M_5$ receptors results in coupling to the Gq/11 family of G proteins, activation of phospholipase C, release of inositol triphosphate (IP3), and subsequent mobilization of intracellular calcium ion. These pathways represent each receptor's coupling capacity leading to the regulation of enzymes and neurotransmitters for intercellular chemical communication and biological function. Although individual GPCRs preferentially couple to a particular class of G-proteins, their specificity is not absolute and usually activate multiple G-proteins with various potency, efficacy and kinetics. Structurally diverse agonists may induce different changes in conformation of GPCRs causing non-uniform modulation of signaling pathways and lead to signaling bias. As described below, this bias has been explored to develop functionally selective drugs with much lower adverse effects than other common drugs. Evidence suggest that analgesic effects of muscarinic agonists are mediated by Gi/o G-proteins coupled to $M_2$ and $M_4$ receptors, and the experiments described below demonstrate that the novel muscarinic agonists described herein are the first to activate only the $\alpha_i$ subunit of G proteins. Therefore, the novel Gi/o biased muscarinic agonists described herein that selectively activate only one specific signaling pathway are novel pharmacophores for development of new painkillers (analgesics).

Accordingly, described herein is a composition including a pharmaceutically acceptable carrier and a muscarinic agonist having the formula:

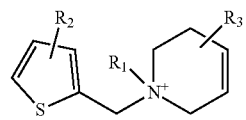

or an analog, derivative or pharmaceutically acceptable salt thereof, wherein:
$R_1$=H or Me;
$R_2$=H, Me, Et, OMe, OEt, F, Cl, Br, I, or $NO_2$; and
$R_3$=H, Me, Et, OMe or $CO_2Me$;
and wherein $R_2$ and $R_3$ may be bonded to any carbon of the 2 rings,
in a therapeutically effective amount for selectively activating at least one of: muscarinic receptor $M_2$ and muscarinic receptor $M_4$, and selectively activating Gi/o signaling in a subject. In one embodiment of the composition, $R_1$, $R_2$ and $R_3$=H and the muscarinic agonist has the formula:

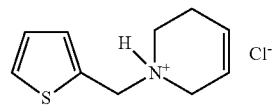 [SMILES: C1=CC[NH+](Cc2cccs2)CC1 ; [Cl-]]

In another embodiment of the composition, $R_1$=Me, $R_2$ and $R_3$=H, and the muscarinic agonist has the formula:

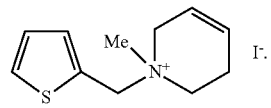

In the compositions, the therapeutically effective amount is from about 1 mg to about 1000 mg. The compositions can be formulated for, as examples, oral or parenteral administration.

Also described herein is a composition including a pharmaceutically acceptable carrier and a muscarinic agonist having the formula:

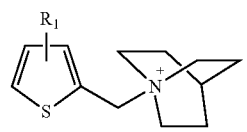

or an analog, derivative or pharmaceutically acceptable salt thereof, wherein:
$R_1$=H, Me, Et, OMe, OEt, F, Cl, Br, I, or $NO_2$, and $R_1$ can be bonded to any carbon atom of the thiophene ring,
in a therapeutically effective amount for selectively activating at least one of: muscarinic receptor $M_2$ and muscarinic receptor $M_4$, and selectively activating Gi/o signaling in a subject. In one embodiment, the muscarinic agonist has the formula:

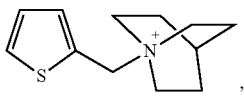

wherein $R_1$=H.

In the compositions, the therapeutically effective amount is from about 1 mg to about 1000 mg. The compositions can be formulated for, as examples, oral or parenteral administration.

Further described herein is a composition including a pharmaceutically acceptable carrier and a muscarinic agonist having the formula:

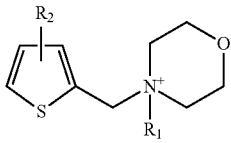

or an analog, derivative or pharmaceutically acceptable salt thereof, wherein:

$R_1$=H or Me;

$R_2$=H, Me, Et, OMe, OEt, F, Cl, Br, I, or $NO_2$;

and wherein $R_2$ can be bonded to any carbon atom of the thiophene ring, in a therapeutically effective amount for selectively activating at least one of: muscarinic receptor $M_2$ and muscarinic receptor $M_4$, and selectively activating Gi/o signaling in a subject. In one embodiment of the composition, the muscarinic agonist has the formula:

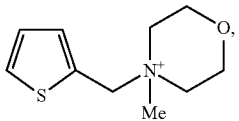

wherein $R_1$=Me, and $R_2$=H.

In the compositions, the therapeutically effective amount is from about 1 mg to about 1000 mg. The compositions can be formulated for, as examples, for oral or parenteral administration.

Still further described herein is a composition including a pharmaceutically acceptable carrier and a muscarinic agonist having the formula:

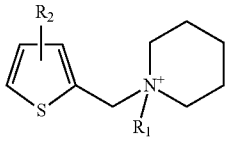

or an analog, derivative or pharmaceutically acceptable salt thereof, wherein:

$R_1$=H or Me;

$R_2$=H, Me, Et, OMe, OEt, F, Cl, Br, I, or $NO_2$; and wherein $R_2$ can be bonded to any carbon atom of the thiophene ring, in a therapeutically effective amount for selectively activating at least one of: muscarinic receptor $M_2$ and muscarinic receptor $M_4$, and selectively activating Gi/o signaling in a subject. In one embodiment of the composition, the muscarinic agonist has the formula ($R_1$=Me, $R_2$=H):

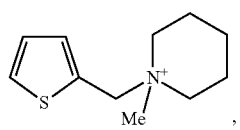

wherein $R_1$=Me, and $R_2$=H.

In the compositions, the therapeutically effective amount is from about 1 mg to about 1000 mg. The compositions can be formulated for, as examples, oral or parenteral administration.

Additionally described herein is a kit for treating a disease or disorder associated with activity of one or both of muscarinic receptor $M_2$ and muscarinic receptor $M_4$ in a subject (e.g., a human). The kit includes: (a) any of the compositions described herein; (b) instructions for use; and (c) packaging. In a typical embodiment, the disease or disorder is a central nervous system disorder and/or a peripheral nervous disorder, and the therapeutically effective amount is an amount sufficient to alleviate, decrease or eliminate pain or discomfort caused by or associated with the disease or disorder in the subject.

Also described herein is a method of treating pain in a subject (e.g., human). The method includes administering to the subject any of the compositions described herein in an amount effective for alleviating, decreasing or eliminating the pain. In the method, the pain is caused by or associated with a disease or disorder that is associated with activity of one or both of muscarinic receptor $M_2$ and muscarinic receptor $M_4$ in a subject. In some embodiments, the disease or disorder is a central nervous system disorder and/or a peripheral nervous disorder. In the method, the composition can be administered, as examples, orally or parenterally. In some embodiments, the composition is administered via injection The terms "group," "functional group," "pendant group," "moiety," "molecular moiety," or the like are somewhat synonymous in the chemical arts and are used to refer to distinct, definable portions or units of a molecule, and to units that perform some function. Examples of groups that are suitable for the compounds described herein include, but are not limited to, H, Me, Et, OMe, OEt, $NO_2$, F, Cl, Br, $CO_2Me$, and the like.

By the term "muscarinic agonist" is meant any compound that binds to a G protein-coupled receptor, resulting in the activation of the G protein and transduction of extracellular to intracellular signals through multiple pathways. A "selective muscarinic agonist" is a muscarinic agonist that preferably binds and activates only one receptor (or 2) subtype(s) among multiple subtypes of the same family. A biased muscarinic agonist is an agonist that leads to the activation of a specific signaling pathway through one or more receptor subtypes. In some embodiments, "a partial muscarinic agonist" is an agonist that reaches only a fractional response of the full agonist's maximal effect ($E_{max}$) in functional assays. When referring to any of the novel muscarinic agonists described herein, the free base, a pharmaceutically acceptable salt or solvate thereof for each compound is encompassed.

The term "purified" means separated from many other entities (small molecules, compounds, proteins, nucleic acids), and does not require the material to be present in a form exhibiting absolute purity, exclusive of the presence of other entities. In some embodiments, a small molecule, compound, protein, nucleic acid or other entity is considered pure (purified) when it is removed from substantially all other entities.

By the terms "to modulate" and "modulates" is meant to increase or decrease. These terms can refer to increasing or decreasing an activity, level or function of a molecule (e.g., protein, peptide, nucleic acid, small molecule, metabolite), or effecting a change with respect to one or more biological or physiological mechanisms, effects, responses, functions, pathways or activities in which, for example, $M_2$ and/or $M_4$ muscarinic receptors are involved. For example, an agonist of a muscarinic receptor (e.g., $M_2$, $M_4$) would increase or up-regulate at least partially the activity and/or function of the receptor.

The terms "agent" and "therapeutic agent" as used herein refer to a chemical entity or biological product, or combination of chemical entities or biological products, administered to a subject (a mammal such as a human) to treat a disease or condition (e.g., a neurological condition, peripheral nervous disorder, etc.). Examples of therapeutic agents include small molecules (compounds) and biologics, which may be referred to herein as a "drug" or "therapeutic drug".

The terms "patient," "subject" and "individual" are used interchangeably herein, and mean a subject, typically a mammal, to be treated, diagnosed, and/or to obtain a biological sample from. Subjects include, but are not limited to, humans, non-human primates, horses, cows, sheep, pigs, rats, mice, insects, dogs, and cats. A human in need of treatment for pain is an example of a subject.

The terms "sample," "patient sample," "biological sample," and the like, encompass a variety of sample types obtained from a patient, individual, or subject and can be used in a therapeutic drug screening, diagnostic or monitoring assay. The patient sample may be obtained from a healthy subject, a diseased patient or a patient having associated symptoms of a particular disease or disorder (e.g., a neurological or peripheral nervous disorder). Moreover, a sample obtained from a patient can be divided and only a portion may be used for therapeutic drug screening. Further, the sample, or a portion thereof, can be stored under conditions to maintain sample for later analysis. The definition specifically encompasses blood and other liquid samples of biological origin (including, e.g., cerebrospinal fluid, plasma, serum, peripheral blood), solid tissue samples such as a biopsy specimen or tissue cultures or cells derived therefrom and the progeny thereof. In a specific embodiment, a sample includes a cerebrospinal fluid sample. In another embodiment, a serum sample is used. The definition also includes samples that have been manipulated in any way after their procurement, such as by centrifugation, filtration, precipitation, dialysis, chromatography, treatment with reagents, washing, or enriched for certain cell populations. The terms further encompass a clinical sample, and also include cells in culture, cell supernatants, tissue samples, and the like. Samples may also include fresh-frozen and/or formalin-fixed, paraffin-embedded tissue blocks, such as blocks prepared from clinical or pathological biopsies, prepared for pathological analysis or study by immunohistochemistry.

As used herein, the terms "central nervous system disorder" and "central nervous system disease" mean any disorder or disease of the central nervous system (CNS).

As used herein, the terms "peripheral nervous disease" and "peripheral nervous disorder" mean any disease or disorder outside the brain and spinal cord.

By "therapeutically effective amount" is meant an amount of a composition of the present invention effective to yield the desired therapeutic response without undue adverse side effects (such as toxicity, irritation, or allergic response). For example, an amount effective to reach maximal effect ($E_{max}$) upon activation of either or both $M_2$ and $M_4$ muscarinic receptors of organ tissues. As another example, an amount effective for promoting or increasing activation or activity of $M_2$ and $M_4$ muscarinic receptors on neuromuscular cells for analgesics purpose in a subject. The specific therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or their derivatives.

As used herein, the terms "therapeutic treatment" and "therapy" are defined as the application or administration of a therapeutic agent (e.g., an analgesic compound as described herein) or therapeutic agents to a patient who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Although compounds, compositions, methods and kits similar or equivalent to those described herein can be used in the practice or testing of the present invention, suitable compounds, compositions, methods and kits are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 17A, accumulation of inositol phosphates (IPX) (M1, M3 and M5 CHO cells) or cAMP (M2 and M4 CHO cells), FIG. 17B, accumulation of inositol IPX (left) or cAMP (right) at non-tranfects CHO-K1 cells, was measured after stimulation by increasing concentrations of carbachol or tested compounds (see legend). Data are expressed as folds over basal level and are means±SD from 5 independent experiments performed in triplicates.

DETAILED DESCRIPTION

Figure 1:
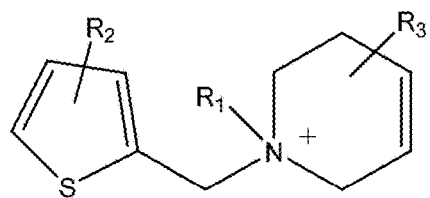
FIG. 1 shows chemical structures of some embodiments of muscarinic receptor agonist compounds as described herein.
Figure 1:
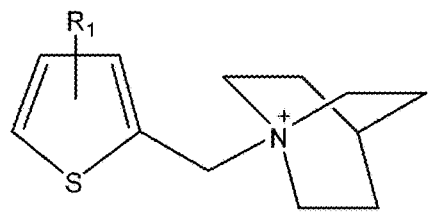
Figure 1:
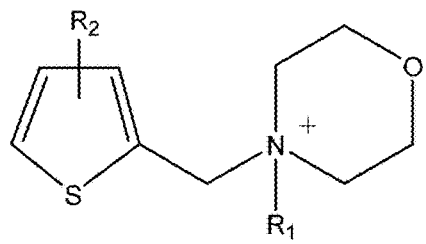
Figure 1:
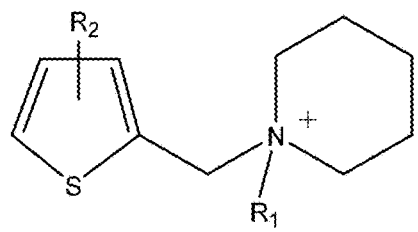

Described herein are novel and much-needed non-steroidal and non-opioid compounds capable of treating pain in an individual by selectively activating $M_2$ and $M_4$ receptors resulting in the coupling of the receptors to the Gi/o family of G proteins, inhibition of adenylate cyclase, reduction in cAMP, and a decrease in neurotransmitter release. These non-steroidal and non-opioid compounds are selective muscarinic agonists. Methods of preparing and synthesizing these compounds, and the use of these compounds for treating pain in a subject (e.g., a human suffering from pain), are also described herein.

Selective Muscarinic Agonists and Compositions Thereof

In one embodiment, a muscarinic agonist has the formula:

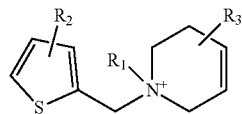

or an analog, derivative or pharmaceutically acceptable salt thereof, wherein:
$R_1$=H or Me; $R_2$=H, Me, Et, OMe, OEt, F, Cl, Br, I, or $NO_2$; and $R_3$=H, Me, Et, OMe, or $CO_2Me$ ($R_2$ and $R_3$ may be bonded to any carbon of the rings). In the Examples below, this muscarinic agonist is referred to as compound 6. In another embodiment, a muscarinic agonist has the formula:

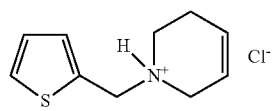

wherein $R_1$, $R_2$, and $R_3$=H. In the Examples below, this muscarinic agonist is referred to as compound 6A. In another embodiment, a muscarinic agonist has the formula:

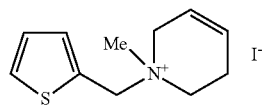

wherein $R_1$=Me, and $R_2$, and $R_3$=H. In the Examples below, this muscarinic agonist is referred to as compound 7A.

In one embodiment, a muscarinic agonist has the formula:

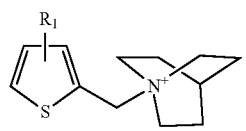

wherein $R_1$=H, Me, Et, OMe, OEt, F, Cl, Br, I, or $NO_2$. In the Examples below, this muscarinic agonist is referred to as compound 8. In another embodiment, the muscarinic agonist has the formula:

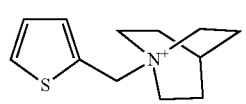

In the Examples below, this muscarinic agonist is referred to as compound 8A ($R_1$=H)

In one embodiment, a muscarinic agonist has the formula:

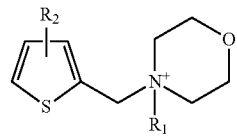

wherein $R_1$=H or Me; $R_2$=H, Me, Et, OMe, OEt, F, Cl, Br, I, or $NO_2$. In the Examples below, this muscarinic agonist is referred to as compound 9. In another embodiment, a muscarinic agonist has the formula:

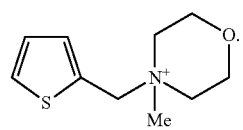

In the Examples below, this muscarinic agonist is referred to as compound 9A ($R_1$=Me, $R_2$=H)

In one embodiment, a muscarinic agonist has the formula:

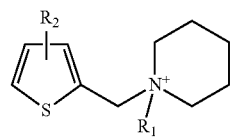

wherein $R_1$=H or Me; $R_2$=H, Me, Et, OMe, OEt, F, Cl, Br, I, or $NO_2$. In the Examples below, this muscarinic agonist is referred to as compound 10. In another embodiment, a muscarinic agonist has the formula:

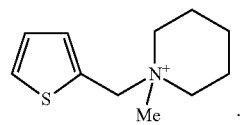 [SMILES: C[N+]1(Cc2cccs2)CCCCC1]

In the Examples below, this muscarinic agonist is referred to as compound 10A ($R_1$=Me, $R_2$=H)

The selective muscarinic agonists (compounds) described herein may exist in enantiomeric as well as diastereomeric forms, and diastereomeric or racemic mixtures. Any suitable analogs or derivatives of the selective muscarinic agonists may also be used. Methods of making the muscarinic agonists are described in detail in the Example below.

Compositions including a muscarinic agonist according to any embodiments described herein typically also include a pharmaceutically acceptable carrier. The therapeutically effective amount is typically from about 1 mg to about 1000 mg. A composition including at least one muscarinic agonist as described herein can be formulated for any suitable form of administration, e.g., oral, parenteral (injection).

Methods of Treating Pain in an Individual

Methods of treating pain in an individual (e.g., human) include administering to the individual a muscarinic agonist as described herein or a composition including a muscarinic agonist as described herein in a therapeutically effective amount to alleviate or eliminate the pain. In a typical embodiment, the pain is caused by or associated with a disease or disorder that is associated with activity of one or both of $M_2$ and $M_4$ muscarinic receptors. In some embodiments, the individual is suffering from a CNS disorder or a peripheral nervous disorder. Specific examples of pain include pain caused after surgery, dental work and cancer treatment. In the example of surgery, administering a muscarinic agonist or composition to an individual suffering from pain decreases the excitability of nociceptive sensory neurons. The muscarinic agonists and compositions containing muscarinic agonists described herein may be used to treat any type of pain that is associated with $M_2$ and/or $M_4$ activity.

The methods described herein can further include detecting a state or condition of pain caused by, for example, a CNS disorder or peripheral nervous disorder in the individual. The detection is typically done prior to administering to the individual a muscarinic agonist or a composition including a muscarinic agonist. Methods of detecting pain caused by, for example, a CNS disorder or peripheral nervous disorder, in an individual are well known in the art.

Any suitable methods of administering a muscarinic agonist or composition including a muscarinic agonist as described herein to an individual may be used. In these methods, the muscarinic agonists and compositions can be administered to an individual by any suitable route, e.g., oral, buccal (e.g., sub-lingual), parenteral (e.g., subcutaneous, intramuscular, intradermal, or intravenous), and topical (i.e., both skin and mucosal surfaces, including airway surfaces), administration. In an embodiment, a muscarinic agonist or composition may be administered systemically by intravenous injection. In another embodiment, a muscarinic agonist or composition may be administered directly to a target site, by, for example, surgical delivery to an internal or external target site, or by catheter to a site accessible by a blood vessel. If administered via intravenous injection, the muscarinic agonist or composition may be administered in a single bolus, multiple injections, or by continuous infusion (e.g., intravenously, by peritoneal dialysis, pump infusion). For parenteral administration, the muscarinic agonist or composition is preferably formulated in a sterilized pyrogen-free form.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that modulates activity of a muscarinic receptor(s), the composition may include suitable parenterally acceptable carriers and/or excipients. The active therapeutic agent(s) (a muscarinic agonist) may be incorporated into microspheres, microcapsules, nanoparticles, liposomes, or the like for controlled release. Furthermore, the composition may include suspending, solubilizing, stabilizing, pH-adjusting agents, and/or dispersing agents.

Formulations for oral use include tablets containing the active ingredient(s) (e.g., a muscarinic receptor agonist or a derivative thereof) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches such as potato starch, calcium carbonate, sodium chloride, lactose, calcium phosphate, calcium sulfate, or sodium phosphate); granulating and disintegrating agents (cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug (a muscarinic agonist as described herein) in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

As indicated above, a muscarinic agonist or composition as described herein may be in a form suitable for sterile injection. To prepare such a composition, the suitable active therapeutic agent(s) (e.g., a therapeutically effective amount of a muscarinic agonist) is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution (D5W, 0.9% sterile saline). The aqueous formulation may also contain one or more preservatives (e.g., methyl, ethyl or n-propyl p-hydroxybenzoate). In cases where the therapeutic agent(s) (1 or more muscarinic agonists) is only sparingly or slightly soluble in water, a dissolution enhancing or solubilizing agent can be added, or the solvent may include 10-60% w/w of propylene glycol or the like. The muscarinic agonists and compositions described herein may be administered to an individual (e.g., rodents, humans, nonhuman primates, canines, felines, ovines, bovines, insects) in any suitable formulation according to conventional pharmaceutical practice (see, e.g., *Remington: The Science and Practice of Pharmacy* (21st ed.), ed. A. R. Gennaro, Lippincott Williams & Wilkins, (2005) and *Encyclopedia of Pharmaceutical Technology*, ($3^{rd}$ ed.) eds. J. Swarbrick and J. C. Boylan, Marcel Dekker, CRC Press, New York (2006), a standard text in this field, and in USP/NF). A description of exemplary pharmaceutically acceptable carriers and diluents, as well as pharmaceutical formulations, can be found in Remington: supra. Other substances may be added to the muscarinic agonists and compositions to stabilize and/or preserve them.

Optionally, a muscarinic agonist or composition as described herein may be administered in combination with any other appropriate therapy; such methods are known to the skilled artisan and described in Remington: The Science and Practice of Pharmacy, supra. Combinations are expected to be advantageously synergistic. Therapeutic combinations that specifically activate one or both of $M_2$ and $M_4$ muscarinic receptors are identified as useful in the methods described herein The therapeutic methods described herein in general include administration of a therapeutically effective amount of the muscarinic agonists and compositions described herein to an individual (e.g., human) in need thereof, particularly a human. Such treatment will be suitably administered to individuals, particularly humans, suffering from, having, susceptible to, or at risk for a disease, disorder, or symptom thereof (e.g., pain). Determination of those individuals "at risk" can be made by any objective or subjective determination by a diagnostic test or opinion of a subject or health care provider.

In one embodiment, the invention provides a method of monitoring treatment progress. The method includes the step of determining a level of change in one or more suitable parameters or markers depending upon the disease or disorder being treated, using, for example, one or more diagnostic markers or diagnostic measurement (e.g., screen, assay) in a subject suffering from or susceptible to a disorder or symptoms thereof associated with activity of $M_2$ and/or $M_4$ muscarinic receptors in which the subject has been administered a therapeutic amount of a muscarinic agonist or composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Effective Doses

The muscarinic agonists and compositions described herein are preferably administered to an individual in need thereof (e.g., human suffering from pain) in an effective amount, that is, an amount capable of producing a desirable result in a treated individual. Desirable results include for example, reducing or eliminating pain in the individual. Such a therapeutically effective amount can be determined according to standard methods. Toxicity and therapeutic efficacy of the muscarinic agonists and compositions utilized in the methods described herein can be determined by standard pharmaceutical procedures. As is well known in the medical and veterinary arts, dosage for any one individual depends on many factors, including the individual's size, body surface area, age, the particular composition to be administered, time and route of administration, general health, and other drugs being administered concurrently. A delivery dose of a muscarinic agonist or composition as described herein is determined based on preclinical efficacy and safety.

Kits

Described herein are kits for treating pain in an individual. A typical kit includes a composition including a muscarinic agonist as described herein and a pharmaceutically acceptable carrier, and instructions for use. Kits also typically include a container and packaging. Instructional materials for preparation and use of the kit components are generally included. While the instructional materials typically include written or printed materials, they are not limited to such. Any medium capable of storing such instructions and communicating them to an end user is encompassed by the kits herein. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The present invention is further illustrated by the following specific examples. The examples are provided for illustration only and should not be construed as limiting the scope of the invention in any way.

Example 1—Discovery and Synthesis of Gi/o Biased Muscarinic Agonists as Potential Non-Steroidal and Non-Opioid Analgesics Potent and functionally selective partial agonists 6A-7D were synthesized and two of these compounds, 6A ($R_1$=$R_2$=$R_3$=H) & 7A ($R_1$=Me, $R_2$=$R_3$=H), were found to be $M_2$/$M_4$ functionally selective muscarinic agonists with unprecedented bias towards the Gi/o signaling pathway based on a novel scaffold containing the NCCSC backbone. These compounds retained their potency, efficacy and bias towards the Gi/o pathway in both dissipated tissues and primary cultures. This NCCSC scaffold that bridges a thiophene ring to a tetrahydropyridinyl, compounds 6, or other nitrogenous cyclic moieties as in compounds 8 (quinuclidinyl), compounds 9 (morpholinyl) and compounds 10 (piperidinyl) via a methylene group ($CH_2$), is a novel pharmacophore in the search for novel non-steroidal and non-opioid analgesics acting via $M_2$ and $M_4$ muscarinic receptors (FIG. 1).

Experimental Results

Binding assay: The binding affinity of compounds 6A-7D was assessed in competition with 1 nM N-methylscopolamine ([$^3$H]NMS). All compounds completely inhibited the binding of [$^3$H]NMS, suggesting competitive mutually exclusive interaction. The equilibrium inhibition constant is reported as $pK_i$ (Table 1).

TABLE 1

Inhibition Constants.

| | $R_1$ | $R_2$ | M1 | M2 | M3 | M4 | M5 |
|---|---|---|---|---|---|---|---|
| 6A | —H | —H | 4.35 ± 0.07 | 4.37 ± 0.06 | 4.43 ± 0.03 | 4.27 ± 0.02 | 4.3 ± 0.1 |
| 6B | —H | —CH3 | 4.6 ± 0.1 | 4.99 ± 0.07* | 4.64 ± 0.04 | 4.54 ± 0.05 | 4.62 ± 0.07 |
| 6C | —H | —Br | 5.12 ± 0.02 | 5.0 ± 0.1 | 4.85 ± 0.06 | 4.90 ± 0.06 | 4.89 ± 0.04 |
| 6E | —H | —CH3 | 4.5 ± 0.1 | 4.9 ± 0.1 | 4.3 ± 0.1 | 4.5 ± 0.1 | 4.5 ± 0.1 |
| 7A | —CH3 | —H | 4.95 ± 0.07 | 5.1 ± 0.1 | 5.1 ± 0.1 | 5.1 ± 0.1 | 5.0 ± 0.2 |
| 7B | —CH3 | —CH3 | 5.4 ± 0.1 | 5.64 ± 0.07* | 5.28 ± 0.05 | 5.36 ± 0.08 | 5.47 ± 0.04 |
| 7C | —CH3 | —Br | 5.82 ± 0.03 | 6.03 ± 0.03 | 5.69 ± 0.07 | 5.84 ± 0.07 | 6.01 ± 0.08 |
| 7D | —CH3 | —Cl | 5.86 ± 0.08 | 6.16 ± 0.06* | 5.47 ± 0.02 | 5.51 ± 0.06 | 5.77 ± 0.05 |

Figure 2:
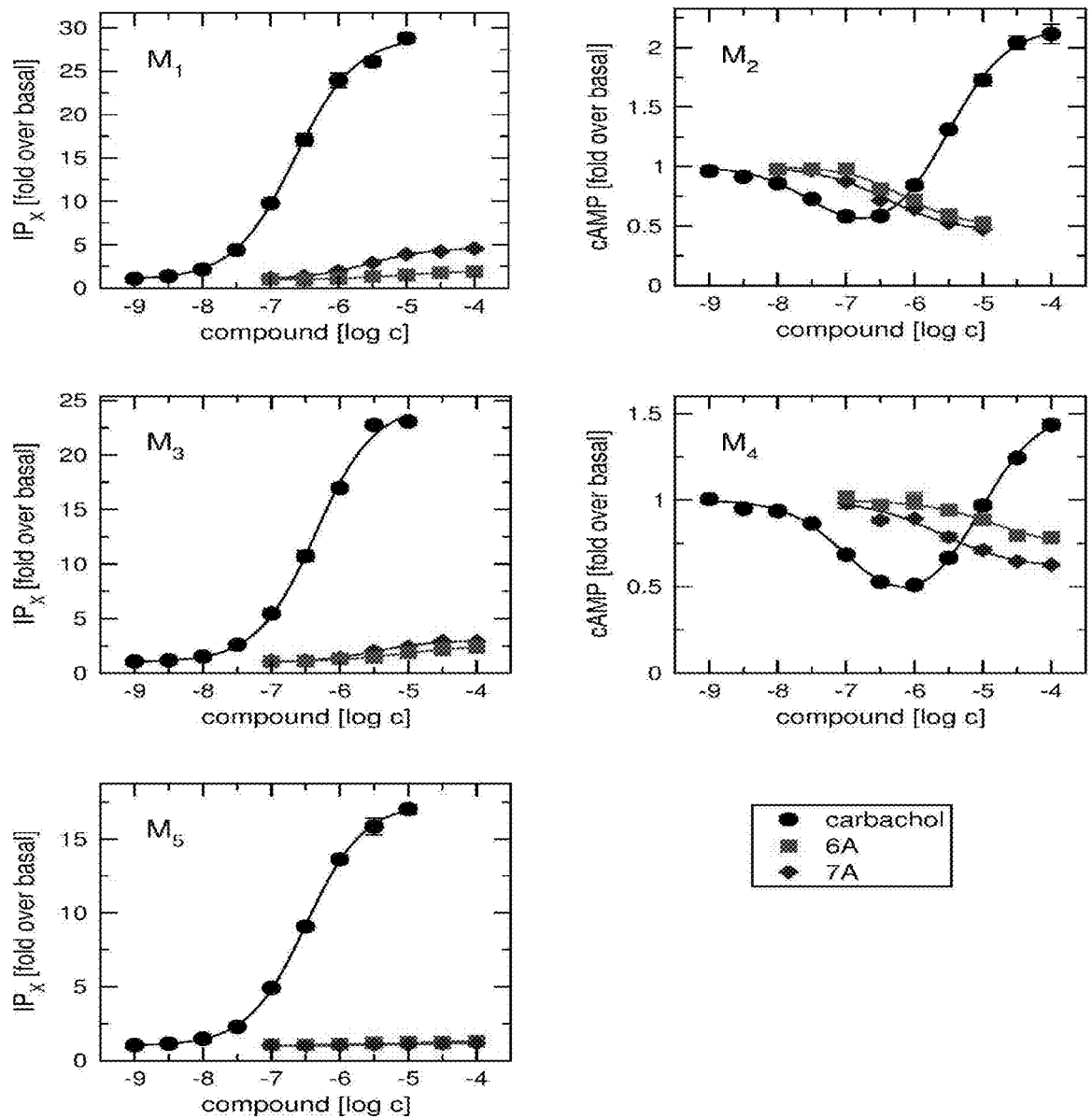
FIG. 2 is a series of graphs showing preferential functional responses to agonists in CHO cells that express individual subtypes of muscarinic receptors. Accumulation of inositol phosphates ($IP_X$) (M1, M3 and M5 CHO cells) or cAMP (M2 and M4 CHO cells) were measured after stimulation by increasing concentrations of carbachol or tested compounds 6A and 7A. Data are expressed as folds over basal level and are means±SD from 5 independent experiments performed in triplicates.

*significantly different (P < 0.05) from other subtypes according to ANOVA and Tukey-Kramer post test.
Inhibition constants ($K_i$) of compounds are expressed as negative logarithms of mean ± SD of 6 independent experiments performed in quadruplicates.
$R_3$ = H in all compounds 6A-7D Functional Assays:

The ability of tested compounds to activate preferential responses via muscarinic receptors was determined by measuring accumulation of inositol phosphates (IPX) at M1, M3 and M5 receptors or inhibition of forskolin-stimulated production of cAMP at M2 and M4 receptors. These results were then compared to responses evoked by the classical non-selective agonist, carbachol. In particular, compounds 6A and 7A displayed comparable responses (Emax) to that of carbachol with potencies (pEC50) at M2 and M4 receptors higher than at other subtypes (FIG. 2). Overall, all compounds were more potent and more efficacious at M2 and M4 receptors than at other receptors.

Figure 3:
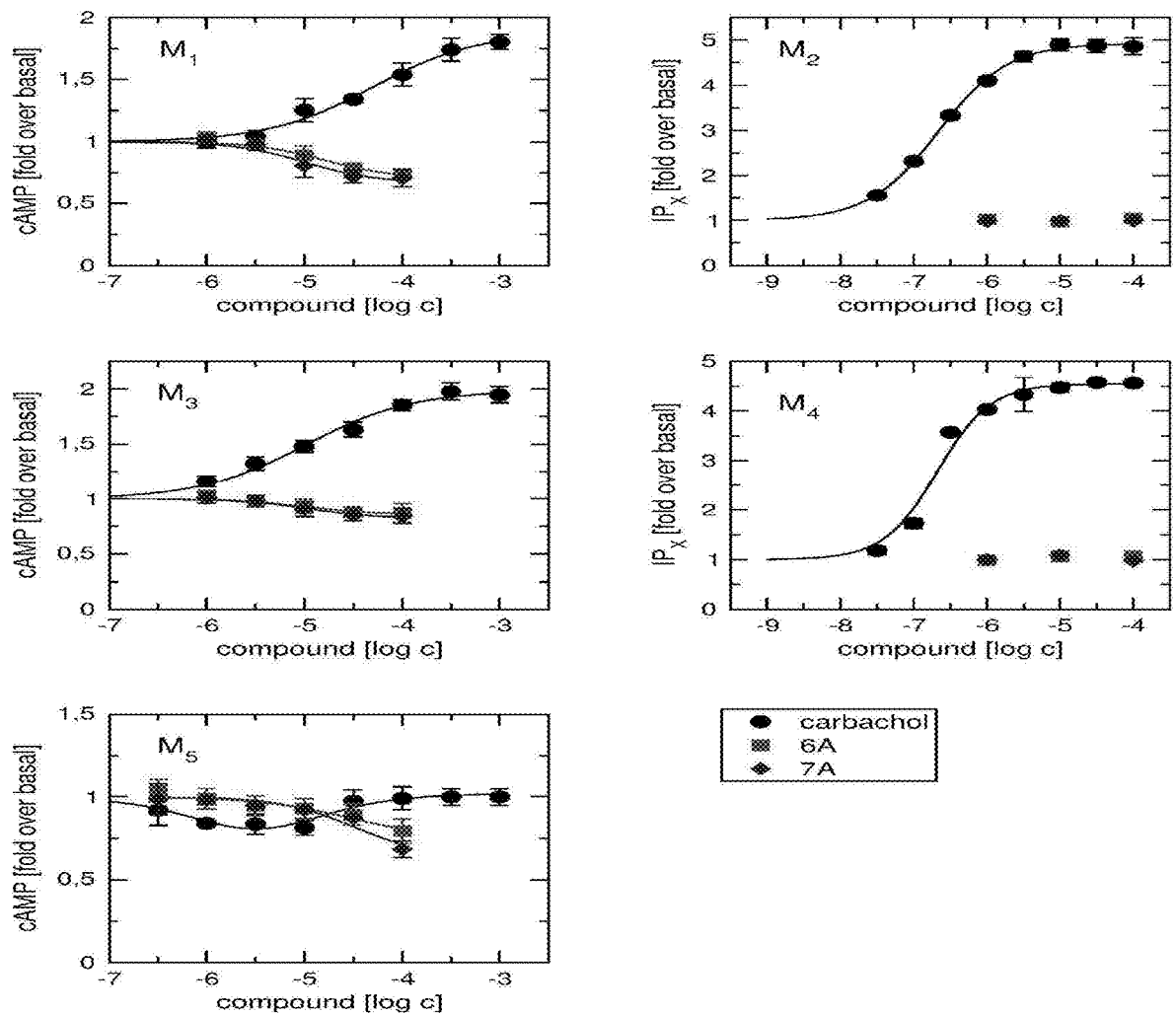
FIG. 3 is a series of graphs showing non-preferential functional responses to agonists in CHO cells that express individual subtypes of muscarinic receptors. Non-preferential signaling was measured, namely accumulation of cAMP (M1, M3 and M5) or $IP_X$ (M2 and M4 CHO cells) after stimulation by increasing concentrations of carbachol or compounds 6A and 7A. Levels of IPX and cAMP are expressed as folds over basal level. Data are means±SD from 5 independent experiments performed in triplicates.

The ability of the two most efficacious compounds 6A and 7A to activate non-preferential responses via muscarinic receptors was determined by measuring of forskolin-stimulated production of cAMP at M1, M3 and M5 receptors or accumulation of $IP_X$ at M2 and M4 receptors co-transfected with promiscuous $G_{15}$ G-protein (FIG. 3). Since activation of phospholipase C (PLC) via M2 and M4 receptors is weak, cells were transferred with G15 G-protein to facilitate coupling. Carbachol activated non-preferential signaling pathways at all receptor subtypes. Carbachol increased cAMP level at M1 and M3 receptors (Gs) and stimulated accumulation of $IP_X$ (Gq) at M2 and M4 receptors. At M5 receptors, carbachol inhibited forskolin-stimulated production of cAMP at nanomolar concentrations but increased cAMP level at micromolar concentrations. In contrast to carbachol, compounds 6A and 7A inhibited cAMP production (Gi/o) at M1, M3 and M5 receptors but did not stimulate $IP_X$ accumulation at M2 and M4 receptors.

Figure 4:
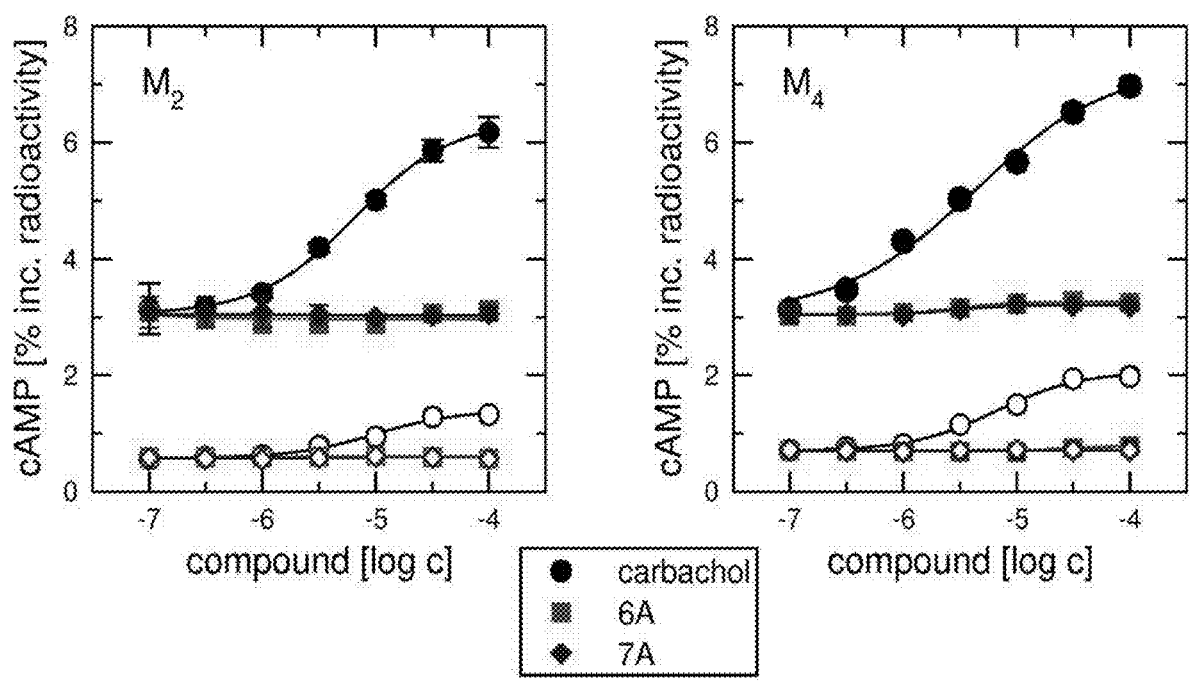
FIG. 4 is a pair of graphs showing accumulation of cAMP at PTX-treated CHO cells. Accumulation of cAMP was measured in CHO cells expressing M2 or M4 receptors that had been treated with pertussis toxin (PTX). Cells were stimulated by increasing concentrations of carbachol, compound 6A or compound 7A in the presence (full symbols) or absence (open symbols) of 10 μM forskolin. Level of cAMP is expressed as percent of incorporated radioactivity converted to cAMP. Data are means±SD from 5 independent experiments performed in triplicates.

To exclude the possibility that activation of the non-preferential Gs pathway was obscured by activation of the preferential Gi/o pathway, accumulation of cAMP was measured in CHO cells expressing M2 or M4 receptors where Gi/o G-proteins were inactivated by pertussis toxin (PTX) treatment (FIG. 4). PTX treatment was successful as carbachol caused no decrease in cAMP. In fact, carbachol caused an increase in forskolin-stimulated (full circles) as well as basal (open circles) accumulation of cAMP in PTX-treated cells. Unlike carbachol, compounds 6A and 7A did not change cAMP levels (did not activate the non-preferential Gs pathway) even after inactivation of Gi/o G-proteins by PTX.

Figure 5:
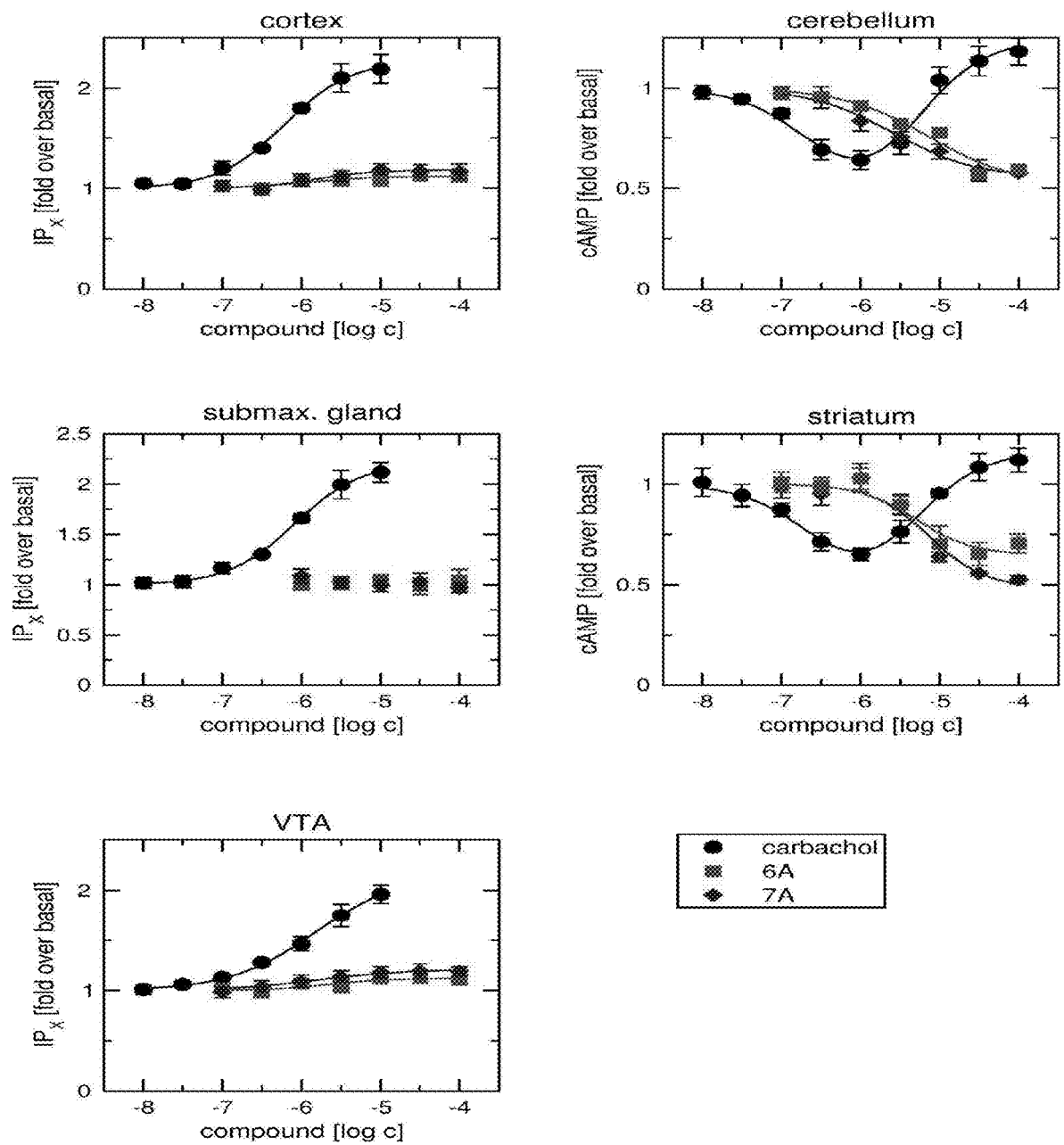
FIG. 5 is a series of graphs showing functional responses to agonists in dissipated rat tissues. Accumulation of IPX in brain cortex (upper left), submaxillary gland (middle left) and ventral tegmental area (VTA, lower left) or cAMP in the cerebellum (upper right) and striatum (middle right) after stimulation by increasing concentrations of carbachol or compounds 6A and 7A was measured. Levels of IPX and cAMP are expressed as folds over basal level. Data are means±SD from 5 independent experiments performed in triplicates.

Effects of compounds 6A and 7A were then measured ex vivo in dissipated rat tissues (FIG. 5). Accumulation of $IP_X$ was measured in dissipated brain cortex (rich in M1 & M3), submaxillary gland (M1 & M3), and ventral tegmental area (M5). Native tissues express about 10-times less muscarinic receptors than CHO cell lines. Accumulation of cAMP was measured in cerebellum (M2) and striatum (M4). Carbachol produced profound accumulation of $IP_X$ in the cortex, submaxillary gland and VTA. In contrast to carbachol, compounds 6A and 7A produced no increase in $IP_X$ levels in submaxillary gland and led to negligible increases in $IP_X$ in the cortex and ventral tegmental area (VTA). In the cerebellum (M2 rich) and striatum (M4 rich), carbachol caused transient decrease in forskolin-stimulated cAMP level at nanomolar concentrations followed by an increase at micromolar concentrations. In contrast to carbachol, compounds 6A and 7A caused only a decrease in cAMP level. Emax of inhibition of cAMP synthesis in the cerebellum and striatum by compounds 6A and 7A was comparable to inhibition by carbachol. Taken together, compounds 6A and 7A only inhibited cAMP synthesis in dissipated tissues and are as efficacious as the full agonist carbachol.

Figure 6:
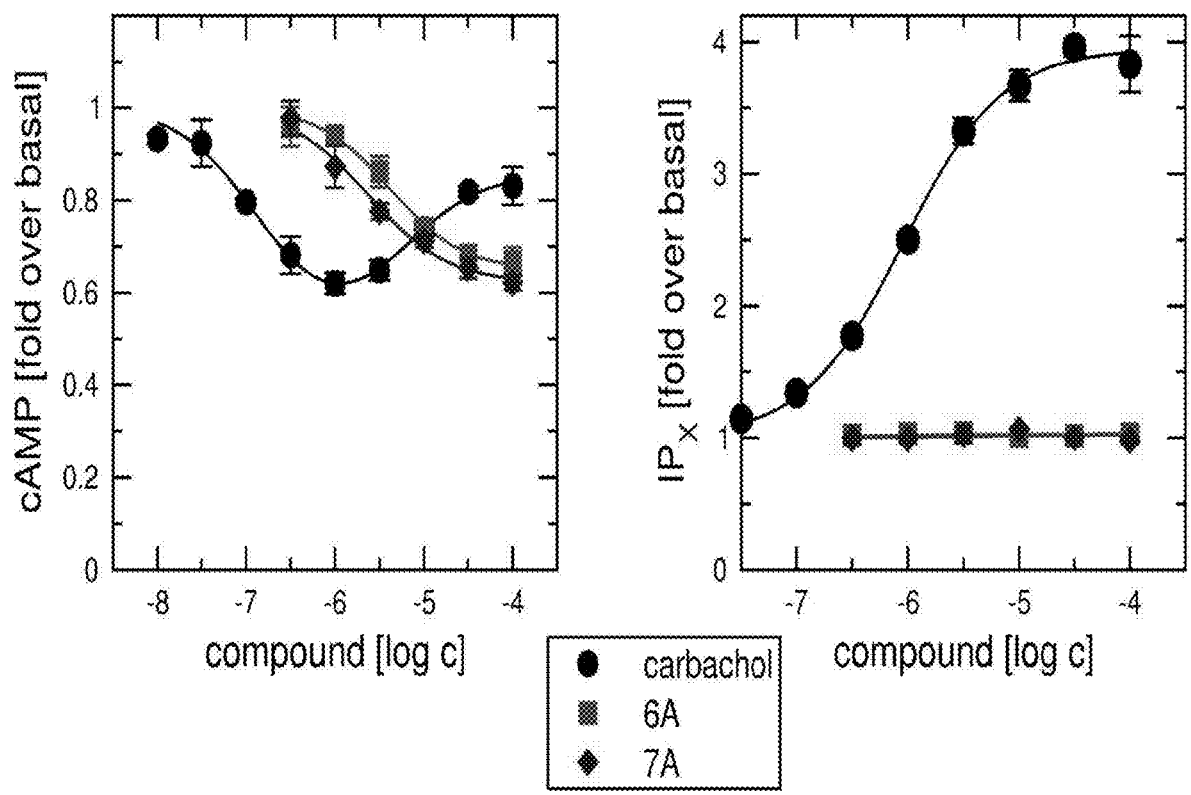
FIGS. 6A and 6B are a pair of graphs showing functional responses to agonists in primary culture of smooth muscle cells. Accumulation of cAMP (left) or IPX (right) in primary culture of smooth muscle cells were measured after stimulation by increasing concentrations of carbachol or compounds 6A and 7A. Levels of IPX and cAMP are expressed as folds over basal level. Data are means±SD from 5 independent experiments performed in triplicates.

Effects of compounds 6A and 7A on both cAMP and $IP_X$ levels were also measured in primary cultures of rat aorta smooth muscle cells that express mainly M2 and to a lesser extent M3 receptors (FIG. 6). Carbachol caused a transient decrease in cAMP level (left) as well as increase in $IP_X$ level (right). Similar to dissipated tissues, compounds 6A and 7A only inhibited cAMP synthesis. Maximal inhibition of cAMP synthesis by compounds 6A and 7A was the same as inhibition by carbachol (about 40%). Receptor expression levels are far lower in tested native tissues than in transfected cell lines and vary among tissues, being highest in the striatum and lowest in the submaxillary gland. Relative expression levels of G-proteins are also known to vary among tissues and cell lines. Thus, it is great to see that the pharmacological profile of the new compounds is conserved despite these variations.

Figure 7:
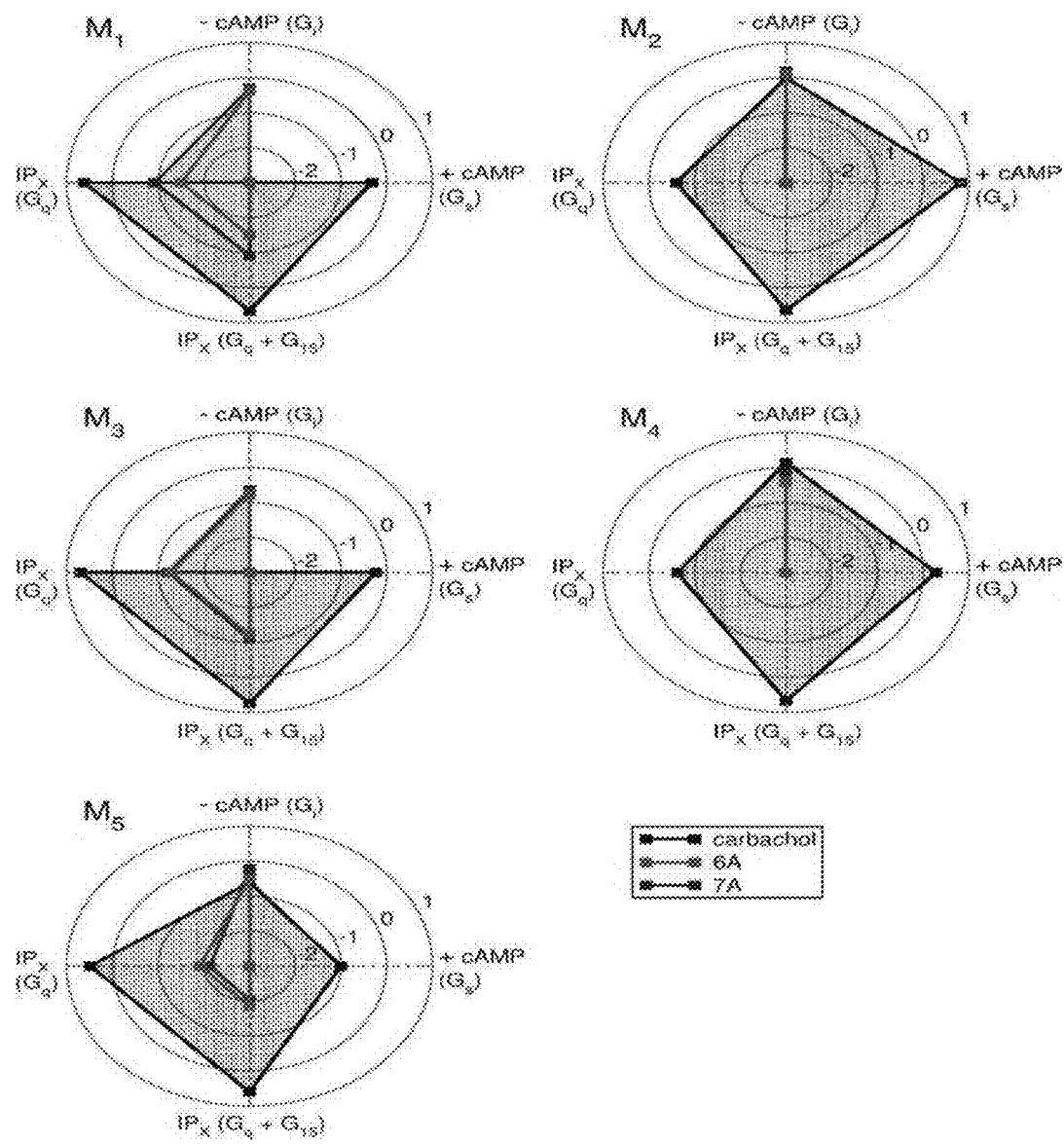
FIG. 7 is a series of polar plots of operational efficiency coefficient τ.

To calculate the operational efficacy coefficient τ (tau) of preferential as well as non-preferential functional response to tested agonists (polar plots, FIG. 7), the system Emax was determined from functional responses to the reference agonists carbachol, oxotremorine and pilocarpine. Since carbachol and oxotremorine did not inhibit forskolin-stimulated production of cAMP at M1 and M3 receptors, system Emax for these systems was determined from functional responses to pilocarpine and compounds 6A and 7A. Equation 1 was fitted to the experimental data $$y = E_{max} * \tau^{nH} * x^{nH} / (x+K_A)^{nH} + \tau^{nH} * x^{nH} \qquad \text{Eq. 1}$$

where y is the functional response at concentration of tested compound x, $E_{max}$ is maximal response of the system, $K_A$ is equilibrium dissociation constant and nH is slope factor. For comparison of effects of agonists at different receptors and signalling pathways, the relative intrinsic activity ($RA_i$) was calculated according to Eq. 2:

$$RA_i = \frac{E'_{MAXcarbachol} * EC_{50a}}{E'_{MAXa} * EC_{50carbachol}} \qquad \text{Eq. 2}$$

Where $EC_{50a}$ and $E'_{MAXa}$ are half-effective concentration and apparent maximal response to the tested compound, respectively. A putative signaling bias between pathway j1 and j2 was estimated by $\Delta\Delta \log(\tau/K_A)$ method according to Eq. 3 [20]:

$$\text{bias} = 10^{\Delta\Delta \log\left(\frac{\tau}{K_A}\right)_{j1-j2}} \qquad \text{Eq. 3}$$

Where $$\Delta\Delta\log\left(\frac{\tau}{K_A}\right)_{j1-j2} = \Delta\log\left(\frac{\tau}{K_A}\right)_{j1} - \Delta\log\left(\frac{\tau}{K_A}\right)_{j2}$$

any receptor subtype. Their Gq efficacy was always lower than that of carbachol while their Gi/o efficacy, except at M4, was always higher than that of carbachol. Compounds 6A and 7A, being Gi/o efficacious at $M_1$ and $M_3$ receptors, displayed an absolute Gi/o bias whereas carbachol showed no Gi/o efficacy at these receptors. Compounds 6A and 7A were especially efficacious at Gi/o pathway at M2 and M4 and also Gi/o biased at these receptors. Compounds 6A and 7A also exerted about 10-fold and 30-fold Gi/o over Gq+G15 at M5 receptors, respectively.

TABLE 2

Efficacies of compounds 6A and 7A to elicit preferential response.
Efficacies of compounds 6A and 7A to elicit preferential response
(stimulation of IPX production at M1, M3 and M5 receptors and inhibition
of cAMP production at M2 and M4 receptors are expressed as intrinsic
activities relative to carbachol (RAi) and as $\Delta\log(\tau/KA)$ to carbachol.

|  | 6A | | 7A | |
| --- | --- | --- | --- | --- |
|  | $RA_i$ | $\Delta\log(\tau/K_A)$ | $RA_i$ | $\Delta\log(\tau/K_A)$ |
| $M_1$ | 0.0010 ± 0.0001 | 2.98 ± 0.26 | 0.0111 ± 0.0002 | 1.96 ± 0.16 |
| $M_2$ | 0.067 ± 0.007* | 1.22 ± 0.08* | 0.140 ± 0.008* | 0.93 ± 0.09* |
| $M_3$ | 0.0058 ± 0.0005 | 2.23 ± 0.23 | 0.011 ± 0.001 | 1.94 ± 0.20 |
| $M_4$ | 0.0046 ± 0.0004 | 2.15 ± 0.16 | 0.0209 ± 0.0011 | 1.58 ± 0.22 |
| $M_5$ | 0.0025 ± 0.0008 | 2.60 ± 0.82 | 0.0007 ± 0.0002 | 3.17 ± 0.88 |

*significantly different (P < 0.01) from other subtypes according ANOVA and Tukey post-test. Values are means ± SD from 5 independent experiments performed in triplicates.

Reaction Scheme 1

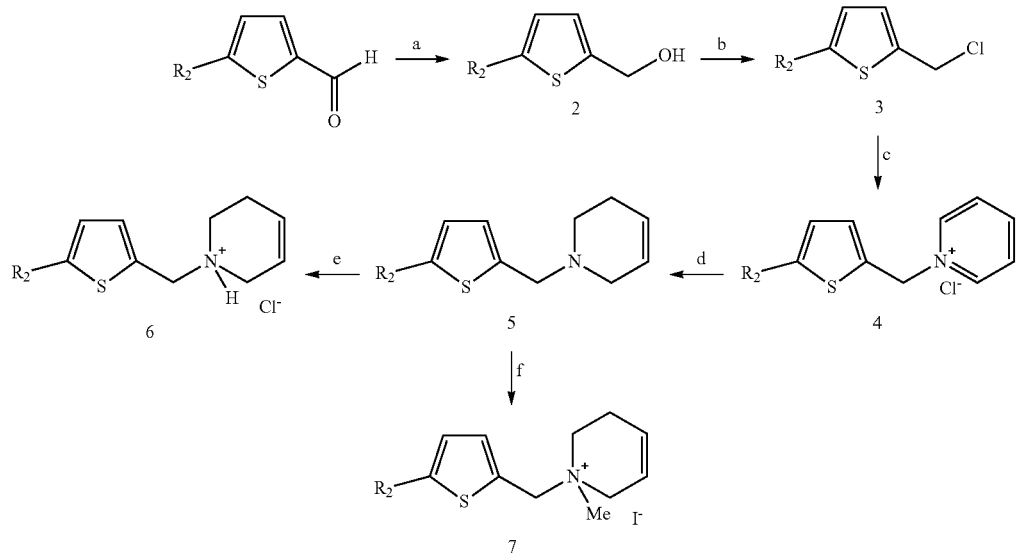

Reagents: a) NaBH₄ b) Ph₃P/CCl₄ c) Pyridine d) NaBH₄ e) HCl gas f) CH₃I $RA_i$ values were calculated to analyse potential selectivity of 6A and 7A intrinsic activities relative to carbachol. Compounds 6A and 7A had the highest $RA_i$ at $M_2$ receptors (Table 2). The reference agonist carbachol was efficacious at stimulation of $IP_X$ (Gq) and cAMP (Gs) production at all subtypes and in lowering cAMP level (Gi/o) at M2, M4 and M5 receptors. Compounds 6A and 7A had no Gs efficacy at A: $R_2$=H C: $R_2$=Br E: $R_2$=Me at C4
B: $R_2$=Me D: $R_2$=Cl Experimental Methods Materials Reagents were purchased from Aldrich Chemical Company (St. Louis, Mo.) unless otherwise noted, and all starting liquid materials were distilled before use. NMR spectra were recorded on a Varian 300 MHz spectrometer housed at Barry University. Mass spectra were recorded on a Perkin Elmer Clarus 560 S GC/MS system. Elemental analyses were carried out by Galbraith Laboratories (Knoxville, Tenn.) and biological assays were conducted at the Institute of Physiology of the Czech Academy of Sciences in Prague. Melting points were recorded on a MEL-TEMP II purchased from Laboratory Devices and are uncorrected. All radiolabeled compounds (N-[$^3$H]methyl scopolamine, myo-[2-$^3$H(N)]inositol and [2,8-$^3$H]adenine) were purchased from American Radiolabeled Chemicals, Inc. (Saint Louis, Mo.). Common chemicals were purchased from (Sigma, Prague, CZ) in the highest available purity.

Chemical Synthesis (Scheme 1)

(thiophen-2-yl)methanol (2A)

Procedure was the same as 2B. Reagents used: 1.50 g of sodium methylate, 3.0 g of sodium borohydride, 12.0 g of thiophene carboxaldehyde (0.107 mol), 75 mL of methanol. 11.0 g recovered (90.16%). $^1$H-NMR (300 MHz, CDCl$_3$) δ 7.3 (1H, d), 7.0 (2H, m), 4.8 (2H, s), 2.2 (1H, bs).

2-(chloromethyl)thiophene (3A)

Procedure was the same as 3B. Reagents used: 9.5 g (0.083 mol) of 2A, 25.32 g (0.0966 mol) of triphenyl phosphine, 60 mL of anhydrous carbon tetrachloride. 7.0 g recovered (63.64%) at 45° C./5 mm Hg. $^1$H-NMR (300 MHz, CD$_3$Cl$_3$) δ 7.75 (1H, d), 7.5 (2H, m), 4.8 (2H, s).

1-[(thiophen-2-yl)methyl]pyridin-1-ium chloride (4A)

Procedure was the same as 4B. Reagents used: 7.0 g of 3A (0.0528 mol), 4.43 g (0.0528 mol) of pyridine, 20 mL of acetonitrile. 8.72 g recovered (78%). $^1$H-NMR (300 MHz, D$_2$O) δ 8.8 (2H, d), 8.4 (1H, t), 7.9 (2H, t), 7.4 (1H, d), 7.2 (1H, dd), 7.0 (1H, d), 5.9 (2H, s).

1-[(thiophen-2-yl)methyl]-1,2,3,6-tetrahydropyridine (5A)

Procedure was the same as 5B. Reagents used: 6.4 g of 4A (0.0302 mol) in 50 mL of methanol, 5.71 g sodium borohydride (0.151 mol), 75 mL of 0.1 N sodium hydroxide. 4.78 g recovered (88.51%). $^1$H-NMR (300 MHz, CDCl$_3$) δ 7.2 (1H, d), 6.9-7.0 (2H, m), 5.8 (1H, m), 5.7 (1H, m), 3.8 (2H, s), 3.0 (2H, m), 2.6 (2H, t), 2.2 (2H, m).

1-[(thiophen-2-yl)methyl]-1,2,3,6-tetrahydropyridin-1-ium chloride (6A)

Procedure was the same as 6B. Reagents used: 1.0 g of 5A (0.0056 mol) in 10 mL of methylene chloride, excess HCl gas. 0.51 g recovered (42.5%) after recrystallization from n-butanol, m.p. 193.5-194.4° C. $^1$H-NMR (300 MHz, D$_2$O) δ 7.5 (1H, d), 7.2 (1H, d), 7.0 (1H, dd), 5.8 (1H, m), 5.55 (1H, m), 4.45 (2H, s), 3.6 (2H, m), 3.5 (1H, m), 3.1 (1H, m), 2.3 (2H, m). Anal. Calcd. For C$_{10}$H$_{14}$NSCl: C, 55.70%, H, 6.5%, N, 6.5%, S, 14.85%, Cl, 16.45%. Found: C, 55.52%, H, 6.42%, N, 6.14%, S, 14.33%, Cl, 16.50%.

1-methyl-1-[(thiophen-2-yl)methyl]-1,2,3,6-tetrahydropyridin-1-ium iodide (7A)

Procedure was the same as 7B. Reagents used: 1.0 mL of methyl iodide, 1.0 g of 5A (0.0056 mol), 2.0 mL acetonitrile.

0.92 g (51.4%) recovered after recrystallization from n-butanol, m.p. 129-130° C. $^1$H-NMR (300 MHz, D$_2$O) δ 7.6 (1H, d), 7.3 (1H, d), 7.1 (1H, dd), 5.9 (1H, m), 5.6 (1H, m), 4.6 (2H, s), 3.9 (1H, m), 3.6 (1H, m), 3.4 (2H, m), 2.9 (3H, s), 2.4 (2H, m). Anal. Calcd. For C$_{11}$H$_{16}$NSI: C, 41.13%, H, 4.99%, N, 4.36%, S, 9.97%, I, 39.55%. Found: C, 41.16%, H, 4.94%, N, 4.16%, S, 9.20%, I, 39.59%.

(5-methylthiophen-2-yl)methanol (2B)

A solution containing 1.50 g of sodium methylate, 3.0 g of sodium borohydride and 25 ml of methanol was slowly added to a mixture containing 13.5 g (0.107 mol) of 5-methyl thiophenecarboxaldehyde and 50.0 mL of methanol with stirring and cooling. The reaction mixture was acidified over crushed ice with 6 M HCl. The mixture was then extracted with anhydrous ether several times, combined ether extracts were dried over anhydrous magnesium sulfate, filtered and concentrated to afford 4.6 g (33.6%). $^1$H-NMR (300 MHz, CD$_3$COCD$_3$) δ 6.7 (1H, d), 6.6 (1H, d), 4.6 (2H, s), 4.4 (1H, bs), 2.4 (3H, s).

2-(chloromethyl)-5-methylthiophene (3B)

A mixture containing 2.3 g of 2B (0.018 mol), 13 ml of anhydrous CCl$_4$ and 5.47 g of triphenylphosphine (0.021 mol) was refluxed for over one hour. After cooling, 100 mL of anhydrous pentane was added and the reaction mixture was filtered, residue washed with another 100 mL of anhydrous pentane. The combined pentane extracts was concentrated and distilled under vacuum to afford 1.44 g (54.75%) at 800/15 mm Hg. $^1$H-NMR (300 MHz, CD$_3$COCD$_3$) δ 7.0 (1H, d), 6.7 (1H, d), 4.9 (2H, s), 2.5 (3H, s).

1-[(5-methylthiophen-2-yl)methyl]pyridin-1-ium chloride (4B)

A mixture containing 1.44 g of 3B (0.010 mol), 0.84 g of pyridine (0.010 mol) and 5.0 mL of acetonitrile was stirred overnight at room temperature. The solution was concentrated to afford 1.92 g (86.88%). $^1$H-NMR (300 MHz, D$_2$O) δ 8.8 (2H, d), 8.4 (1H, t), 7.9 (2H, t), 7.0 (1H, d), 6.65 (1H, d), 5.8 (2H, s), 2.35 (3H, s).

1-[(5-methylthiophen-2-yl)methyl]-1,2,3,6-tetrahydropyridine (5B)

A solution containing 0.38 g (0.010 mol) of sodium borohydride and 17.0 mL of 0.10 N NaOH was slowly added to another solution of 1.92 g (0.00852 mol) of 4B in 12.0 mL of methanol with stirring and cooling. After 30 minutes of additional stirring and cooling, the solution was acidified with 6 M HCl and pH was readjusted to 7-8 with 1M NaOH. The solution was then extracted three times with CH$_2$Cl$_2$ and all organic extracts were combined, dried over anhydrous MgSO$_4$, filtered and concentrated to yield 1.50 g (92.0%). $^1$H-NMR (300 MHz, CDCl$_3$) δ 6.75 (1H, d), 6.6 (1H, d), 5.8 (1H, m), 5.7 (1H, m), 3.8 (2H, s), 3.0 (2H, d), 2.6 (2H, d), 2.45 (3H, s), 2.2 (2H, m).

1-[(5-methylthiophen-2-yl)methyl]-1,2,3,6-tetrahydropyridin-1-ium chloride (6B)

Excess hydrogen chloride gas was passed through a solution containing 0.75 g (0.00389 mol) of 5B dissolved in 9 mL of acetonitrile. The solution was stirred overnight at room temperature, concentrated and the residue was recrystallized from n-butanol/ether to yield 0.645 g (72.39%), m.p. 175-176° C. ¹H-NMR (300 MHz, D₂O) δ 6.95 (1H, d), 6.7 (1H, d), 5.8 (1H, m), 5.55 (1H, m), 4.35 (2H, s), 3.6-3.4 (3H, m), 3.05 (1H, m), 2.35 (3H, s), 2.25 (2H, m). Anal. Calcd. For $C_{11}H_{16}NSCl$: C, 57.51%, H, 6.97%, N, 6.10%, S, 13.97%, Cl, 15.45%. Found: C, 57.08%, H, 7.12%, N, 5.83%, S, 14.10%, Cl, 15.92%.

1-methyl-1-[(5-methylthiophen-2-yl)methyl]-1,2,3, 6-tetrahydropyridin-1-ium iodide (7B)

Excess iodomethane was added to a solution containing 0.75 g (0.00389 mol) of 5B dissolved in 9 mL of acetonitrile. The solution was stirred overnight at room temperature, concentrated and the residue was recrystallized from n-butanol to yield 0.50 g (38.46%), m.p. 159-160° C. ¹H-NMR (300 MHz, D₂O) δ 7.1 (1H, d), 6.75 (1H, d), 5.9 (1H, m), 5.6 (1H, m), 4.5 (2H, s), 3.95-3.85 (1H, m), 3.65 (1H, m), 3.4-3.3 (2H, m), 2.9 (3H, s), 2.4 (2H, m), 2.35 (3H, s). Anal. Calcd. For $C_{12}H_{18}NSI$: C, 42.99%, H, 5.37%, N, 4.18%, S, 9.57%, I, 37.89%. Found: C, 43.57%, H, 5.42%, N, 4.17%, S, 9.21%, I, 39.51%.

(5-bromothiophen-2-yl)methanol (2C)

A solution containing 1.06 g (0.020 mol) sodium methylate, 2.15 g (0.0573 mol) of sodium borohydride and 25 ml of methanol was slowly added to a mixture containing 9.57 g (0.0535 mol) of 5-bromo thiophenecarboxaldehyde and 30.0 mL of methanol with stirring and cooling. The reaction mixture was acidified over crushed ice with 6 M HCl. The mixture was then extracted with anhydrous ether several times, combined ether extracts dried over anhydrous magnesium sulfate, filtered and concentrated to afford 6.5 g (67.15%). ¹H-NMR (300 MHz, CDCl₃) δ 6.9 (1H, d), 6.8 (1H, d), 4.6 (2H, s), 2.0 (1H, bs).

2-bromo-5-(chloromethyl)thiophene (3C)

Procedure same as 3B. Reagents used: 6.55 g (0.0362 mol) of 2C, 10.94 g (0.042 mol) of triphenyl phosphine, 25 mL of anhydrous carbon tetrachloride. About 4.67 g recovered (64.7%). The crude product was distilled under vacuum to afford 2.17 g of pure 3C (30.1%), b.p. 70° C./10 mm Hg. ¹H-NMR (300 MHz, CD₃Cl₃) δ 6.9 (1H, d), 6.8 (1H, d), 4.7 (2H, s).

1-[(5-bromothiophen-2-yl)methyl]pyridin-1-ium chloride (4C)

Procedure same as 4B. Reagents used: 2.17 g of 3C (0.0109 mol), 0.84 g (0.010 mol) of pyridine, 5 mL of acetonitrile. 2.30 g (72.7%) recovered. ¹H-NMR (300 MHz, D₂O) δ 9.8 (2H, d), 8.4 (2H, t), 7.9 (1H, t), 7.0 (1H, d), 6.9 (1H, d), 5.8 (2H, s).

1-[(5-bromothiophen-2-yl)methyl]-1,2,3,6-tetrahydropyridine (5C)

Procedure was same as 5B. Reagents used: 2.0 g of 4C (0.0069 mol) in 10 mL of methanol, 0.40 g sodium borohydride (0.0105 mol), 14 mL of 0.1 N sodium hydroxide. 1.36 g recovered (76.8%). ¹H-NMR (300 MHz, CDCl₃) δ 6.9 (1H, d), 6.7 (1H, d), 5.8 (1H, m), 5.65 (1H, m), 3.75 (2H, s), 3.0 (2H, d), 2.6 (2H, t), 2.2 (2H, m).

1-[(5-bromothiophen-2-yl)methyl]-1,2,3,6-tetrahydropyridin-1-ium chloride (6C)

Procedure same as 6B. Reagents used: 0.55 g of 5C (0.00213 mol) in 10 mL of acetonitrile, excess HCl gas. 0.30 g recovered (47.6%) after recrystallization from n-butanol, m.p. 205.3-206.5° C. ¹H-NMR (300 MHz, D₂O) δ 7.05 (1H, d), 6.95 (1H, d), 5.9-5.8 (1H, m), 5.55 (1H, m), 4.4 (2H, m), 3.4-3.6 (3H, m), 3.1 (1H, m), 2.3 (2H, m). Anal. Calcd. For $C_{10}H_{13}NSBrCl$: C, 40.79%, H, 4.41%, N, 4.75%, S, 10.87%. Found: C, 40.70%, H, 4.53%, N, 4.88%, S, 9.79.

1-[(5-bromothiophen-2-yl)methyl]-1-methyl-1,2,3,6-tetrahydropyridin-1-ium iodide (7C)

Procedure same as 7B. Reagents used: 1.0 mL of methyl iodide, 0.80 g of 5C (0.0031 mol), 1.5 mL acetonitrile. 0.90 g (72.58%) recovered after recrystallization from n-butanol, m.p. 151-152.3° C. ¹H-NMR (300 MHz, D₂O) δ 7.1 (1H, d), 7.05 (1H, d), 5.9 (1H, m), 5.6 (1H, m), 4.6 (2H, s), 3.9-3.8 (1H, m), 3.7-3.6 (1H, m), 3.4-3.3 (2H, m), 2.9 (3H, s), 2.4 (2H, m). Anal. Calcd. For $C_{11}H_{15}NBrSI$: C, 33.04%, H, 3.75%, N, 3.50%, S, 8.00%. Found: C, 33.4%, H, 3.82%, N, 3.62%, S, 7.02%.

(5-chlorothiophen-2-yl)methanol (2D)

0.821 g (0.022 mol) of sodium borohydride dissolved in 30 mL of 0.1N NaOH was slowly added to a mixture containing 2.8 g (0.0191 mol) of 5-chloro thiophenecarboxaldehyde and 10.0 mL of methanol with stirring and cooling. The reaction mixture was acidified over crushed ice with 6 M HCl. The mixture was then extracted with anhydrous ether several times, combined ether extracts dried over anhydrous magnesium sulfate, filtered and concentrated to afford 1.87 g (65.9%). ¹H-NMR (300 MHz, CDCl₃) δ 7.0 (1H, d), 6.9 (1H, d), 4.7 (2H, s), 2.2 (1H, bs).

2-chloro-5-(chloromethyl)thiophene (3D)

Procedure was the same as 3B. Reagents used: 1.85 g (0.0126 mol) of 2D, 3.83 g (0.0146 mol) of triphenyl phosphine, 10 mL of anhydrous carbon tetrachloride to afford 1.53 g (72.8%). ¹H-NMR (300 MHz, CD₃Cl₃) δ 6.85 (1H, d), 6.78 (1H, d), 4.7 (2H, s).

1-[(5-chlorothiophen-2-yl)methyl]pyridin-1-ium chloride (4D)

Procedure was the same as 4B. Reagents used: 1.50 g of 3D (0.0090 mol), 0.62 g (0.009 mol) of pyridine, 5 mL of acetonitrile. 1.2 g (54.3%) recovered. ¹H-NMR (300 MHz, D₂O) δ 8.75 (1H, t), 8.4 (2H, t), 7.9 (2H, t), 7.06 (1H, d), 6.85 (1H, d), 5.75 (2H, s).

1-[(5-chlorothiophen-2-yl)methyl]-1,2,3,6-tetrahydropyridine (5D)

Procedure was the same as 5B. Reagents used: 1.2 g of 4D (0.0049 mol) in 6 mL of methanol, 0.282 g sodium borohydride (0.00744 mol) in 8 mL of 0.1 N sodium hydroxide. 0.87 g recovered (83.5%). ¹H-NMR (300 MHz, CDCl₃) δ 6.75 (1H, d), 6.7 (1H, d), 5.75 (1H, m), 5.65 (1H, m), 3.7 (2H, s), 3.0 (2H, m), 2.6 (2H, t), 2.2 (2H, m).

1-[(5-chlorothiophen-2-yl)methyl]-1-methyl-1,2,3,6-tetrahydropyridin-1-ium iodide (7D)

Procedure was the same as 7B. Reagents used: 1.0 mL of methyl iodide, 0.40 g of 5D (0.00187 mol), 2 mL acetonitrile. 0.56 g (83.6%) recovered after recrystallization from n-butanol, m.p. 153.4-155.2° C. $^1$H-NMR (300 MHz, D$_2$O) δ 7.1 (1H, d), 6.9 (1H, d), 5.9 (1H, m), 5.6 (1H, m), 4.55 (2H, s), 3.95-3.8 (1H, m), 3.7-3.6 (1H, m), 3.4-33 (2H, m), 2.95 (3H, s), 2.45 (2H, m). Anal. Calcd. For C$_{11}$H$_{15}$NSICl: C, 37.17%, H, 4.22%, N, 3.94%, S, 9.00%. Found: C, 37.57%, H, 4.27%, N, 3.84%, S, 9.21%.

(4-methylthiophen-2-yl)methanol (2E)

Same procedure as 2B. Reagents used: 0.2284 g of sodium methylate, 0.45 g of sodium borohydride, 2.10 g of 4-methylthiophene carboxaldehyde (0.017 mol), 25 mL of methanol. 2.03 g of recovered (96.3%). $^1$H-NMR (300 MHz, CDCl$_3$) δ 6.85 (1H, s), 6.90 (1H, s), 4.65 (2H, s), 2.25 (3H, s).

2-(chloromethyl)-4-methylthiophene (3E)

Procedure was the same as 3B. Reagents used: 2.00 g (0.0156 mol) of 2E, 4.01 g (0.0153 mol) of triphenyl phosphine, 12 mL of anhydrous carbon tetrachloride. 2.0 g recovered (87.3%). $^1$H-NMR (300 MHz, CD$_3$Cl$_3$) δ 7.1 (1H, s), 7.0 (1H, s), 4.9 (2H, s), 2.2 (3H, s).

1-[(4-methylthiophen-2-yl)methyl]pyridin-1-ium chloride (4E)

Procedure was the same as 4B. Reagents used: 2.0 g of 3E (0.0137 mol), 1.08 g (0.0137 mol) of pyridine, 5 mL of acetonitrile. 1.23 g recovered (39.8%). $^1$H-NMR (300 MHz, D$_2$O) δ 9.8 (2H, d), 8.4 (1H, t), 7.95 (2H, m), 7.1 (1H, s), 7.05 (1H, s), 5.8 (2H, s), 2.1 (3H, s).

1-[(4-methylthiophen-2-yl)methyl]-1,2,3,6-tetrahydropyridine (5E)

Procedure was the same as 5B. Reagents used: 1.2 g of 4E (0.0053 mol) in 7 mL of methanol, 0.218 g sodium borohydride (0.00576 mol), 10 mL of 0.1 N sodium hydroxide. 0.50 g recovered (49.0%). $^1$H-NMR (300 MHz, CD$_3$COCD$_3$) δ 6.4 (1H, s), 6.3 (1H, s), 5.7 (1H, m), 5.65 (1H, m), 3.7 (2H, s), 2.95 (2H, m), 2.85 (2H, t), 2.55 (2H, t), 2.2 (3H, s).

1-[(4-methylthiophen-2-yl)methyl]-1,2,3,6-tetrahydropyridin-1-ium chloride (6E)

Excess hydrogen chloride gas was passed through a solution containing 0.25 g (0.0013 mol) of 5E dissolved in 2 mL of dichloromethane. The solution was stirred overnight at room temperature, concentrated and the residue was recrystallized from n-butanol to yield 0.20 g (68.9%), m.p. 149-152° C. $^1$H-NMR (300 MHz, D$_2$O) δ 7.06 (1H, s), 7.05 (1H, s), 5.9-5.8 (1H, m), 5.6-5.5 (1H, m), 4.4 (2H, s), 3.6-3.40 (3H, m), 3.1-3.0 (1H, m), 2.3 (2H, s), 2.1 (3H, s). Anal. Calcd. For C$_{11}$H$_{16}$NSCl: C, 57.51%, H, 6.97%, N, 6.10%, S, 13.97%. Found: C, 56.27%, H, 6.76%, N, 5.79%, S, 13.17%.

Biological

Cell Culture and Membrane Preparation

Chinese hamster ovary cells stably transfected with the genes of human variants of muscarinic receptors were purchased from Missouri S&T cDNA Resource Center (Rolla, Mo., USA). Cell cultures and crude membranes were prepared as described previously. Cells were grown to confluency in 75 cm$^2$ flasks in Dulbecco's modified Eagle's medium supplemented with 10% fetal bovine serum and 2 million of cells were subcultured to 100 mm Petri dishes. Medium was supplemented with 5 mM butyrate for the last 24 hours of cultivation to increase receptor expression. Cells were detached by mild trypsinization on day 5 after subculture. Detached cells were washed twice in 50 ml of phosphate-buffered saline and 3 min centrifugation at 250×g. Washed cells were suspended in 20 ml of ice-cold incubation medium (100 mM NaCl, 20 mM Na-HEPES, 10 mM MgCl$_2$, pH=7.4) supplemented with 10 mM EDTA and homogenized on ice by two 30 sec strokes using Polytron homogenizer (Ultra-Turrax; Janke & Kunkel GmbH & Co. KG, IKA-Labortechnik, Staufen, Germany) with a 30-sec pause between strokes. Cell homogenates were centrifuged for 30 min at 30,000×g. Supernatants were discarded, pellets suspended in fresh incubation medium, incubated on ice for 30 minutes and centrifuged again. Resulting membrane pellets were kept at −80° C. until assayed within 10 weeks at a maximum.

Equilibrium Radioligand Binding Experiments

All radioligand binding experiments were optimized and carried out as described earlier. Briefly, membranes were incubated in 96-well plates at 30° C. in the incubation medium described above. Incubation volume was 400 µl or 800 µl for competition and saturation experiments with [$^3$H]NMS, respectively. Approximately 30 µg of membrane proteins per sample were used. N-methylscopolamine binding was measured directly in saturation experiments using six concentrations (30 pM to 1000 pM) of [$^3$H]NMS for 1 hour. Nonspecific binding was determined in the presence of 1 µM unlabeled atropine. Incubations were terminated by filtration through Whatman GF/C glass fiber filters (Whatman) using a Brandel cell harvester (Brandel, Geithesburg, Md., USA). Filters were dried in microwave oven and then solid scintillator Meltilex A was melted on filters (105° C., 90 s) using a hot plate. The filters were cooled and counted in Wallac Microbeta scintillation counter.

Measurements of the Production of cAMP and of Inositol Phosphates

Levels of second messenger cAMP and inositol phosphates were determined in radiochemical chromatography assays as described previously (Jakubik et al., 1996). To determine level of cAMP, cells in suspension were pre-incubated for 1 h with 0.4 µM [$^3$H]adenine, washed, and incubated for 10 min in the presence of isobutylmethylxanthine and 10 µM forskolin. Then about 200 thousands cells per 0.8 ml sample were incubated for 1 h with carbachol or tested compounds. Incubation was ended by addition of 0.2 ml of 2.5 M HCl to the samples. Samples were applied to alumina columns (1.5 g of alumina per column), washed with 2 ml ammonium acetate (pH=7.0) and eluted from columns with 4 ml ammonium acetate and measured by liquid scintillation spectrometry. To determine the rate of formation of inositol phosphates IP$_X$, suspended cells were pre-incubated with 0.1 µM [$^3$H]myo-inositol for 60 min, washed, and incubated with 10 mM LiCl for 15 min, followed by incubation with carbachol or tested compounds for 60 min. The incubation was stopped by addition of 0.5 ml of chloroform methanol HCl mixture (2:1:0.1). After separation of water and organic phases, 0.6 ml of water phase was applied to Dowex columns (1.5 g of Dowex per column), washed by 20 ml of 60 mM ammonium formate/5 mM sodium borate buffer and eluted from columns with 4 ml of 1M ammonium formate/0.1 formic acid buffer and measured by liquid scintillation spectrometry. All pre-incubations and incubations were carried in Krebs-HEPES buffer (KHB; final concentrations in mM: NaCl 138; KCl 4; CaCl$_2$ 1.3; $MgCl_2$ 1; $NaH_2PO_4$ 1.2; HEPES 20; glucose 10; pH adjusted to 7.4) supplemented with 10 mM glucose at 37° C.

Conclusion

Described herein is the development of novel muscarinic agonists exerting unprecedented signaling bias towards the Gi/o signaling pathway leading to high functional selectivity at $M_2$ and $M_4$ receptors. Small muscarinic agonists were synthesized, namely 1-H-1-[(5-substituted thiophen-2-yl) methyl]-3,6-dihydro-2H-pyridin-1-ium hydrochloride and methyl iodide salts (6A and 7A, respectively). Compounds displayed various potency and efficacy to stimulate muscarinic receptors and are mainly partial agonists. In measurements of functional response to agonists, compounds (6A and 7A) only inhibited forskolin-stimulated synthesis of cAMP at $M_2$ and $M_4$ receptors. In contrast to the classical non-selective agonist carbachol, compounds 6A and 7A did not activate $G_s$ nor $G_q$ signaling pathways. Coupling selectivity may be influenced by the expression level of receptors and members of the signaling pathways, including G-proteins and effectors. To exclude contribution of this system bias, the functional response to compounds 6A and 7A was also measured ex vivo in several dissipated rat tissues and primary culture of rat smooth muscle cells. Similar to CHO cells, 6A and 7A only activated the $G_{i/o}$ signaling pathway, supporting real ligand bias.

Similar to the analgesia mediated by opioid receptors, activation of $M_2$ receptors leads to activation of $G_{i/o}$ G-proteins and consequent decrease in cAMP which causes attenuation in the activity of tetrodotoxin-resistant voltage-gated sodium channels. The βγ dimers released from activated $G_{i/o}$ G-proteins activate inwardly-rectifying potassium channels. A decrease in the activity of sodium channels and activation of potassium channels result in a decrease in excitability of nociceptive sensory neurons. Muscarinic agonists represent one of the most promising strategies for developing novel analgesic agents to replace addictive opioid analgesics. In conclusion, compounds 6A and 7A may serve as leads and a pharmacophore in the search for novel non-steroidal and non-opioid analgesics. Additional analogues, compounds 8, 9 and 10, are currently in development and being tested for potency and efficacy at both $M_2$ and $M_4$ muscarinic receptors.

Example 2—Additional Muscarinic Agonists

Additional analogues of 6, 8, 9 and 10 with a variety of $R_2$ and $R_3$ (H, Me, Et, OMe, OEt, $NO_2$, F, Cl, Br), $R_1$ (H, Me) and $R_3$ (H, Me, Et, OMe, $CO_2Me$) substituents are synthesized using the methods described above to identify additional potent and efficacious muscarinic agonists.

Example 3—Novel $M_2$-Selective, $G_i$-Biased Agonists of Muscarinic Acetylcholine Receptors Novel agonists of muscarinic acetylcholine receptors were synthesized and their binding and function was tested in CHO cells expressing individual subtypes of muscarinic receptors, primary cultures and dissipated native tissues. Binding of novel compounds was modelled in silico. Two of the tested new compounds (1-(thiophen-2-ylmethyl)-3,6-dihydro-2H-pyridinium [also referred to as 6A and 1-[(thiophen-2-yl)methyl]-1,2,3,6-tetrahydropyridin-1-ium chloride (6A)] and 1-methyl-1-(thiophen-2-ylmethyl)-3,6-dihydro-2H-pyridinium) [also referred to as 7A and 1-methyl-1-[(thiophen-2-yl)methyl]-1,2,3,6-tetrahydropyridin-1-ium iodide] only inhibited cAMP synthesis in CHO cells, primary cultures and native tissues, with selectivity for M2 muscarinic receptors and displaying bias towards the Gi signalling pathway at all subtypes of muscarinic receptors. Molecular modelling revealed interactions with the orthosteric binding site in a way specific for a given agonist followed by agonist-specific changes in the conformation of the receptor. The identified compounds may serve as lead-structures for novel non-steroidal and non-opioid analgesics acting via $M_2$ and $M_4$ muscarinic receptors with reduced side effects associated with activation of phospholipase C signalling pathway. Agonists, solely inhibiting cAMP synthesis, as described herein (e.g., 6A, 7A), may serve as novel pharmacophores for development of new painkillers with reduced side-effects mediated by phospholipase C pathway.

Materials and Methods

Materials: Reagents were purchased from Aldrich Chemical Company (St. Louis, Mo.) unless otherwise noted, and all starting liquid materials were distilled before use. NMR spectra were recorded on a Varian 300 MHz spectrometer housed at Barry University. Mass spectra were recorded on a Perkin Elmer Clarus 560 S GC/MS system. Elemental analyses were carried out by Galbraith Laboratories (Knoxville, Tenn.) and biological assays were conducted at the Institute of Physiology of the Czech Academy of Sciences in Prague. Melting points were recorded on a MEL-TEMP II purchased from Laboratory Devices and are uncorrected. All radiolabelled compounds (N-[$^3$H]methyl scopolamine, myo-[2-$^3$H(N)]inositol and [2,8-$^3$H]adenine) were purchased from American Radiolabelled Chemicals, Inc. (Saint Louis, Mo.). Common chemicals were purchased from (Sigma, Prague, CZ) in the highest available purity.

Cell culture and membrane preparation: Chinese hamster ovary (CHO) cells stably transfected with the genes of individual human variants of muscarinic receptors were purchased from Missouri S&T cDNA Resource Center (Rolla, Mo., USA). Fresh primary cell culture of smooth muscle cells (SMC) from rat aorta prepared as previously described was kindly provided by Dr. Lucie Bačáková. Primary culture of SMCs was grown to confluency in 75 cm$^2$ flasks in Dulbecco's modified Eagle's medium supplemented with 10% fetal bovine serum. Up to 6-times, 2 million of cells were sub-cultured. Cell cultures and crude membranes from CHO cells were prepared as described previously (Boulos et al., Chem Biol Drug Des 1-12, 2017). Cells were grown to confluency in 75 cm$^2$ flasks in Dulbecco's modified Eagle's medium supplemented with 10% fetal bovine serum and 2 million of cells were subcultured in 100 mm Petri dishes. Medium was supplemented with 5 mM butyrate for the last 24 hours of cultivation to increase receptor expression. When needed, cells were cultivated with pertussis toxin at a final concentration of 25 ng/ml for the 24 hours. Cells were detached by mild trypsinization on day 5 after subculture. Detached cells were washed twice in 50 ml of phosphate-buffered saline and 3 min centrifugation at 250×g. Washed cells were suspended in 20 ml of ice-cold incubation medium (100 mM NaCl, 20 mM Na-HEPES, 10 mM $MgCl_2$, pH=7.4) supplemented with 10 mM EDTA and homogenized on ice by two 30 sec strokes using Polytron homogenizer (Ultra-Turrax; Janke & Kunkel GmbH & Co. KG, IKA-Labortechnik, Staufen, Germany) with a 30-sec pause between strokes. Cell homogenates were centrifuged for 30 min at 30,000×g. Supernatants were discarded, pellets suspended in fresh incubation medium, incubated on ice for 30 minutes and centrifuged again. Resulting membrane pellets were kept at −80° C. until assayed within 10 weeks at a maximum.

Rat dissipated tissues: Suspension of dissipated tissues from rat brain cortex, cerebellum, striatum, ventral tegmental area (VTA) and submaxillary glands was prepared as described previously in supplementary methods. Adult 8-weeks old male Wistar rats were scarified by cervical dislocation in accordance with current legislative and guidelines under permission of Czech Ministry of Agriculture 16OZ23113/2017-17214. Tissues were dissected immediately. Submaxillary glands were minced by scissors. Tissues were dispersed by incubation for 15 min at 37° C. in KHB supplemented with trypsin and trituration every 5 min. Large undissipated parts were removed by cell mesh. Then dissipated tissues were centrifuged 3 min at 250×g, re-suspended in KHB and centrifuged again to remove trypsin. Suspension of dissipated tissues was used immediately in experiments. Two submaxillary glands or about 400 mg of brain tissue was used a 96-sample assay.

Equilibrium radioligand binding experiments: All radioligand binding experiments were optimized and carried out according to general guidelines. Briefly, membranes were incubated in 96-well plates at 30° C. in the incubation medium described above. Incubation volume was 400 µl or 800 µl for competition and saturation experiments with [$^3$H]NMS, respectively. Approximately 30 µg of membrane proteins per sample were used. N-methylscopolamine binding was measured directly in saturation experiments using six concentrations (30 pM to 1000 pM) of [$^3$H]NMS for 1 hour. For calculations of equilibrium dissociation constant ($K_D$), concentrations of free [$^3$H]NMS were calculated by subtraction of bound radioactivity from total radioactivity in the sample and fitting Eq. 1 (data analysis section). Binding of tested ligands was determined in competition experiments with 1 nM [$^3$H]NMS. Membranes were incubated for 1 ($M_2$), 3 ($M_1$, $M_3$, $M_4$) or 5 hours ($M_5$) at 30° C. Inhibition constant $K_I$ was calculated according Eq. 3. Non-specific binding was determined in the presence of 1 pM unlabeled atropine. Incubations were terminated by filtration through Whatman GF/C glass fibre filters (Whatman) using a Brandel cell harvester (Brandel, Geithesburg, Md., USA). Filters were dried in microwave oven and then solid scintillator Meltilex A was melted on filters (105° C., 90 s) using a hot plate. The filters were cooled and counted in Wallac Microbeta scintillation counter.

Measurements of the production of cAMP and inositol phosphates: Levels of second messengers cAMP and inositol phosphates were determined in radiochemical chromatography assays as described previously. To determine level of cAMP, cells in suspension were pre-incubated for 1 h with 0.4 µM [$^3$H]adenine, washed, and incubated for 10 min in the presence of isobutylmethylxanthine and 10 µM forskolin. Then about 200 thousand cells per 0.8 ml sample were incubated for 1 h with carbachol or tested compounds. Incubation was ended by addition of 0.2 ml of 2.5 M HCl to the samples. Samples were applied to alumina columns (1.5 g of alumina per column), washed with 2 ml ammonium acetate (pH=7.0) and eluted from columns with 4 ml ammonium acetate and measured by liquid scintillation spectrometry. $M_2$ and $M_4$ receptors that preferentially inhibit cAMP synthesis via $G_{i/o}$ G-proteins were coupled to the $G_q$-PLC pathway. For this purpose, new CHO cell lines stably expressing promiscuous $G_{15}$ G-protein and $M_2$ or $M_4$ receptor were generated by transfection with pCMV/hygro vector and hygromycin selection. To determine the rate of formation of inositol phosphates $IP_X$, suspended cells were pre-incubated with 0.1 µM [$^3$H]myo-inositol for 60 min, washed, and incubated with 10 mM LiCl for 15 min. Then about 200 thousand cells per 0.8 ml sample were incubated for 1 h with carbachol or tested compounds for 60 min. The incubation was stopped by addition of 0.5 ml of chloroform methanol HCl mixture (2:1:0.1). After separation of water and organic phases, 0.6 ml of water phase was applied to Dowex columns (1.5 g of Dowex per column), washed by 20 ml of 60 mM ammonium formate/5 mM sodium borate buffer and eluted from columns with 4 ml of 1M ammonium formate/0.1 formic acid buffer and measured by liquid scintillation spectrometry. All pre-incubations and incubations were carried in Krebs-HEPES buffer (KHB; final concentrations in mM: NaCl 138; KCl 4; $CaCl_2$ 1.3; $MgCl_2$ 1; $NaH_2PO_4$ 1.2; HEPES 20; glucose 10; pH adjusted to 7.4) supplemented with 10 mM glucose at 37° C.

Data and analysis: Experiments were independent, using different seedings of CHO cells or explanted from different animals. Binding experiments were carried out in 6 experiments with samples in quadruplicates and functional assays were carried out in 5 experiments with samples in triplicates. Experimenters were blind to chemical structures of tested compounds. After subtraction of non-specific binding (binding experiments) or background/blank values (functional experiments) data were normalized to control values determined in each experiment. $IC_{50}$ and $EC_{50}$ values and parameters derived from them ($K_i$ and $K_A$) were treated as logarithms. All data were included in analysis, no outliers were excluded, and normality of distribution was checked. In statistical analysis value of $P<0.01$ was taken as significant for all data. In multiple comparison tests ANOVA with $P<0.01$ was followed by Tukey post-test ($P<0.01$). Statistics was calculated using R.

[$^3$H]NMS Saturation Binding $$y = \frac{B_{MAX} * x}{x + K_D} \qquad \text{Eq. 1}$$

where y is specific binding at free concentration x, $B_{MAX}$ is maximum binding capacity, and $K_D$ is equilibrium dissociation constant.

Competition Binding $$y = 100 - \frac{100 * x}{x + IC_{50}} \qquad \text{Eq. 2}$$

where y is specific radioligand biding at concentration x of competitor expressed as percent of binding in the absence of competitor, $IC_{50}$ is concentration causing 50% inhibition of radioligand binding. Inhibition constant $K_I$ was calculated as:

$$K_I = \frac{IC_{50}}{1 + \frac{[D]}{K_D}} \qquad \text{Eq. 3}$$

where $IC_{50}$ is concentration causing 50% inhibition of [$^3$H] NMS binding calculated according Eq. 2 from competition binding data, [D] is concentration of [$^3$H]NMS used, and $K_D$ is its equilibrium dissociation constant calculated according Eq. 1 from saturation binding data.

Functional Response $$y = 1 + \frac{(E'_{MAX} - 1) * x^{nH}}{EC_{50}^{nH} + x^{nH}} \qquad \text{Eq. 4}$$

where y is functional response at concentration of tested compound x, $E'_{MAX}$ is apparent maximal response to the tested compound, $EC_{50}$ is concentration causing half-efficient concentration and nH is slope factor (Hill coefficient). For bi-phasic response, curves were inhibitory and stimulatory phase were fitted separately.

Operational Model of Functional Agonism

Operational efficacy coefficient τ was determined by fitting Eq. 5 to data from functional assay.

$$y = \frac{E_{MAX} * \tau^{nH} * x^{nH}}{(x + K_A)^{nH} + \tau^{nH} * x^{nH}} \qquad \text{Eq. 5}$$

where y is functional response at concentration of tested compound x, $E_{MAX}$ is maximal response of the system, $K_A$ is equilibrium dissociation constant and nH is slope factor. Eq. 5 was fitted to data from functional experiments. Eq. 5 was fitted to data by the two-step procedure described earlier. In the first step, system $E_{MAX}$ was determined using carbachol, oxotremorine, and pilocarpine as internal standards by global fit to all data for a given receptor subtype and signaling pathway. In the second step, Eq. 5 with $E_{MAX}$ fixed to the value determined in the first step was fitted to individual experimental data sets.

Relative Intrinsic Activity

For comparison of effects of agonists at different receptors and signalling pathways, relative intrinsic activity ($RA_i$) was calculated according to Griffin et al. (Griffin et al., J. Pharmacol. Exp. Ther. 321:1193-1207, 2007):

$$RA_i = \frac{\tau_{carbachol} * K_{Aa}}{\tau_a * K_{Acarbachol}} \qquad \text{Eq. 6}$$

Where $\tau_a$ and $K_{Aa}$ are half-effective concentration and apparent maximal response to the tested compound, respectively. As Hill coefficients were equal to one, $RA_i$ values were calculated according Eq. 7.

$$RA_i = \frac{E'_{MAXcarbachol} * EC_{50a}}{E'_{MAXa} * EC_{50carbachol}} \qquad \text{Eq. 7}$$

Where $EC_{50a}$ and $E'_{MAXa}$ are half-effective concentration and apparent maximal response to the tested compound, respectively.

Signalling Bias

A putative signalling bias between pathway j1 and j2 was estimated by $\Delta\Delta \log(\tau/K_A)$ method according to Eq. 8 based on Eq. 6:

$$\text{bias} = 10^{\Delta\Delta\log\left(\frac{\tau}{K_A}\right)_{j1-j2}} \qquad \text{Eq. 8}$$

Where $$\Delta\Delta\log\left(\frac{\tau}{K_A}\right)_{j1-j2} = \Delta\log\left(\frac{\tau}{K_A}\right)_{j1} - \Delta\log\left(\frac{\tau}{K_A}\right)_{j2} \qquad \text{Eq. 9}$$

Results

Figure 15:
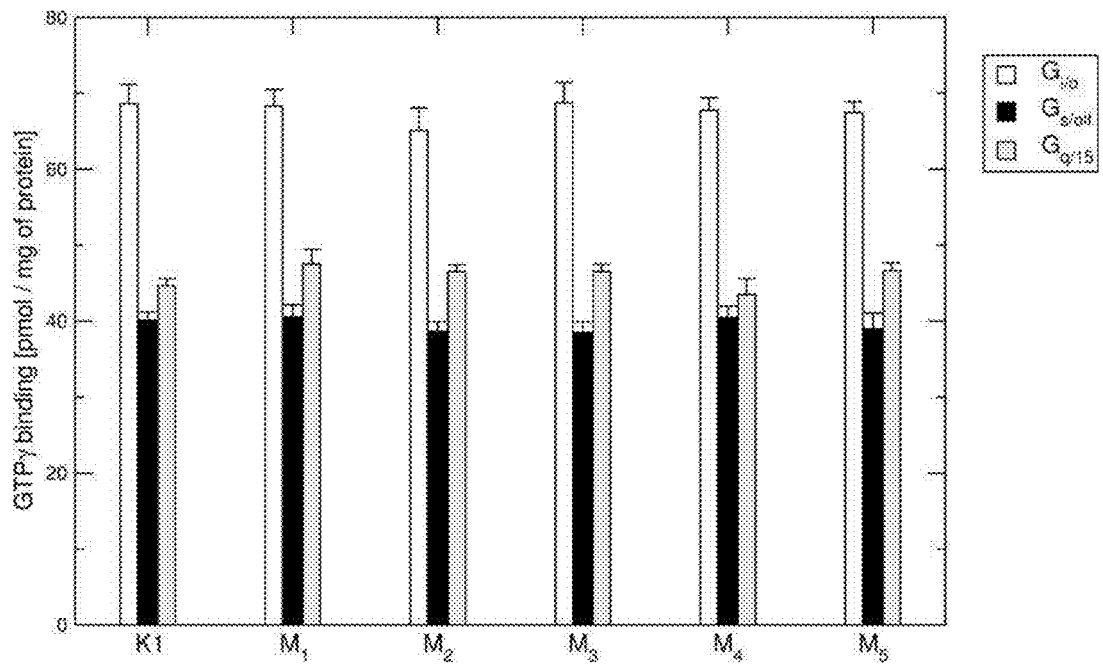
FIG. 15 is a graph showing expression level of G-proteins. Expression levels of individual classes of G-proteins were determined as binding of 0.5 nM [$^{35}$S]GTPγS in the absence of GDP determined in scintillation proximity assay as described in Jakubik et al. (Mol Pharmacol 70: 656-666, 2006).
Figure 16:
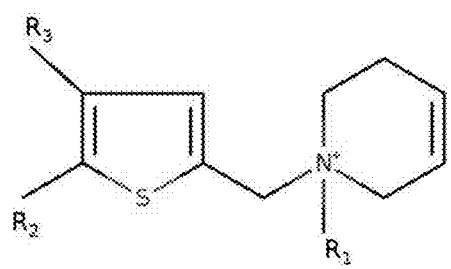
FIG. 16 is a scheme of novel agonists. Core structure of 1-(thiophen-2-ylmethyl)-1,2,3,6-tetrahydropyridin-1-ium. Core structure was substituted at the nitrogen ($R_1$) and at positions 5 ($R_2$) and 4 ($R_3$) of the thiophene ring. Substitutes $R_1$, $R_2$ and $R_3$ are summarized in Table 4.

New compounds were tested in CHO cell lines stably expressing the human variants of individual subtypes of muscarinic receptors. Expression level of individual subtypes of muscarinic receptors was determined in N-methylscopolamine ([$^3$H]NMS) saturation binding studies and are listed alongside with [$^3$H]NMS equilibrium dissociation constants below under Supplemental Information, Table 4. Expression level of individual classes of G-proteins was determined by [$^{35}$S]GTPγS scintillation proximity assay and is summarized in Supplementary information, FIG. 15. Affinity of new compounds (Supplementary Information, FIG. 16) was assessed in competition with 1 nM [$^3$H]NMS (Supplementary Information, Table 5). All compounds completely inhibited the binding of [$^3$H]NMS, suggesting competitive mutually exclusive interaction. All compounds bound to all subtypes of muscarinic receptors with affinity in the micromolar range. Inhibition constants $K_i$ ranged from 0.7 μM for compound 7D at $M_2$ receptors to 54 μM for compound 6A at $M_4$ receptors. Compounds with methylated nitrogen (7A, 7B and 7C) had higher affinity than non-methylated counterparts (6A, 6B and 6C) at all receptor subtypes. Affinities of compounds with halogenated thiophene at the 5-position (7C and 7D) ring were higher than those of non-halogenated congeners, especially at $M_2$ receptors. About 20% binding to $M_2$ and 10% of binding to $M_4$ of compounds 6B and 7B occurred with high affinity (about 30 nM). Reference agonists displayed high and low affinity binding (Example 4-Table 6).

Figure 8:
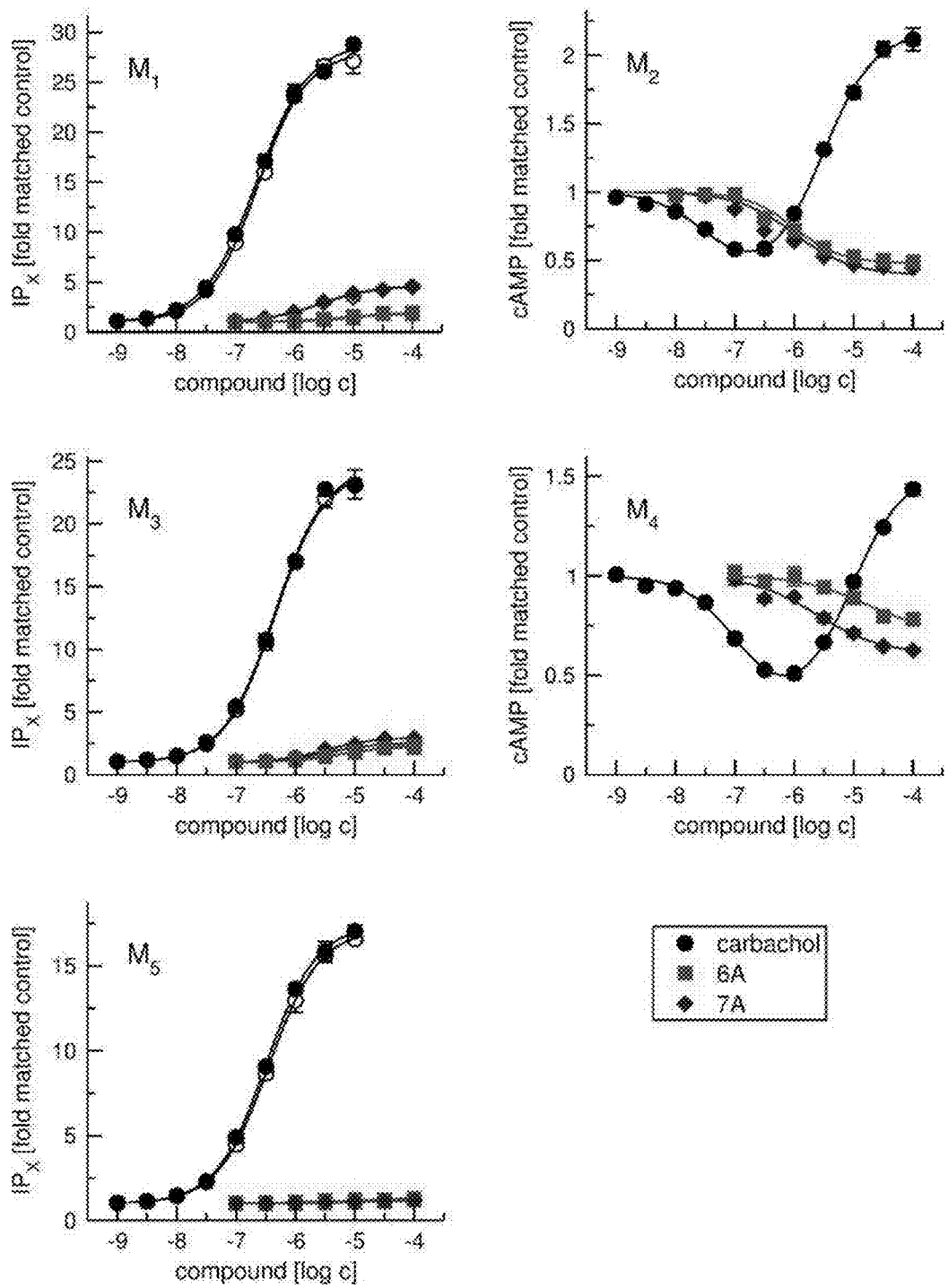
FIG. 8 is a series of graphs showing preferential functional responses to agonists in CHO cells that express individual subtypes of muscarinic receptors. Accumulation of inositol phosphates (IPX) ($M_1$, $M_3$ and $M_5$ CHO cells) or forskolin-stimulated cAMP ($M_2$ and $M_4$ CHO cells) at non-transfected (open symbols) or $G_{15}$ G-protein transfected cells (closed symbols) were measured after stimulation by increasing concentrations of carbachol or tested compounds (see legend). Data are expressed as folds of matched controls and are means±SD from 5 independent experiments performed in triplicates.
Figure 17A:
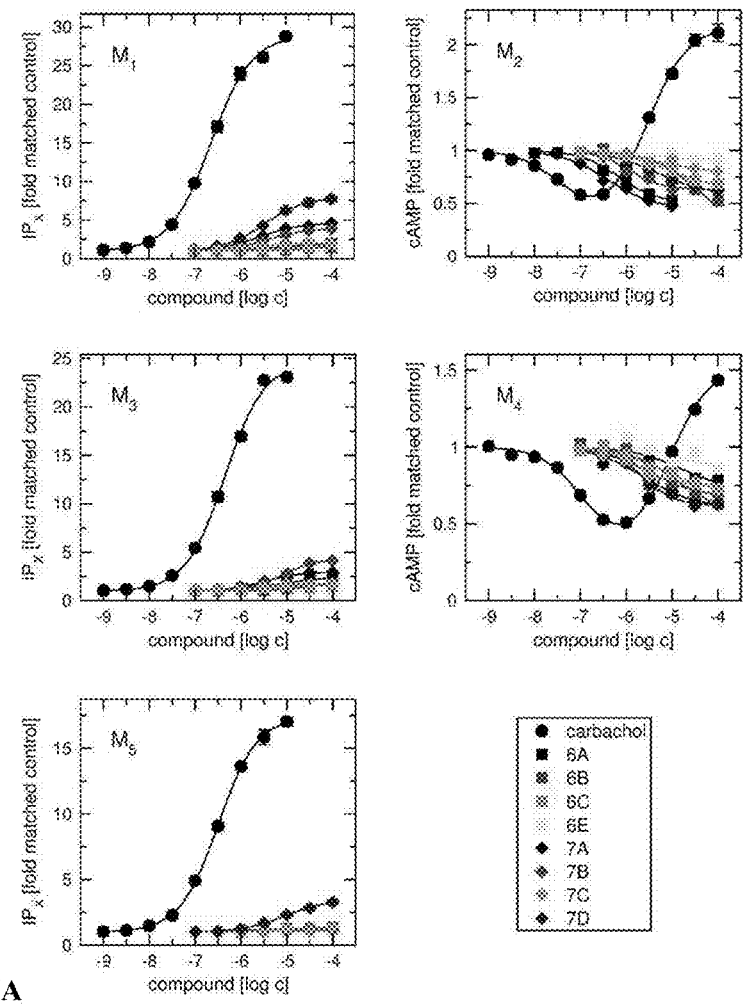
FIGS. 17A and 17B are a series of graphs showing preferential functional responses to agonists in CHO cells that express individual subtypes of muscarinic receptors.
Figure 17B:
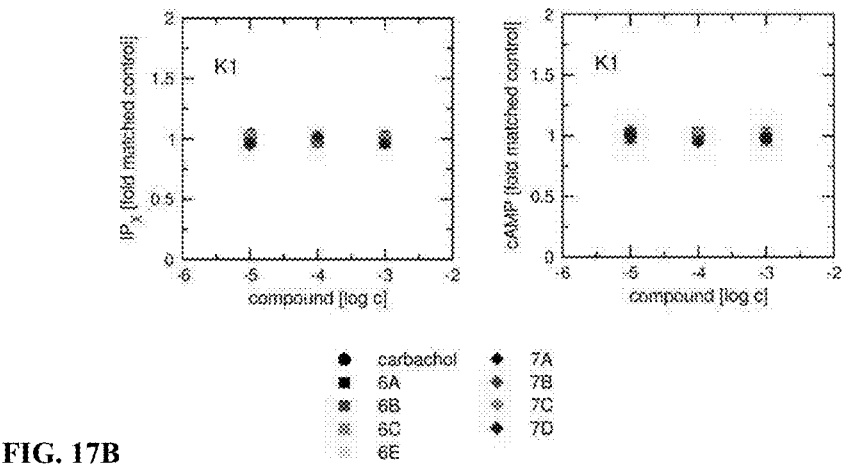

$M_1$, $M_3$ and $M_5$ receptors preferentially activate phospholipase C and increase the level of inositol phosphates ($IP_X$) via coupling with $G_{q/11}$ G-proteins. $M_2$ and $M_4$ receptors preferentially inhibit production of cAMP via coupling with $G_{i/o}$ G-proteins. The ability of tested compounds to activate preferential signalling pathways of muscarinic receptors was determined in functional experiments by measuring accumulation of $IP_X$ at $M_1$, $M_3$ and $M_5$ receptors or inhibition of forskolin-stimulated production of cAMP at $M_2$ and $M_4$ receptors. These results were then compared to responses evoked by the classical non-selective orthosteric agonists, carbachol, oxotremorine and pilocarpine (Supplementary Information, Table 7). Except for compound 6E (methyl group at the 4-position of the thiophene ring), all compounds acted as partial to full agonists at all receptor subtypes, although in many cases, especially at $M_1$, $M_3$ and $M_5$ receptors, their effects were negligible (Supplementary Information Table 7, FIG. 17). In particular, compounds 6A and 7A displayed at $M_2$ and $M_4$ response ($E_{MAX}$) comparable to that of carbachol. Their potency ($pEC_{50}$) at $M_2$ and $M_4$ receptors was higher than at other subtypes (FIG. 8). Overall, all compounds were more potent and more efficacious at $M_2$ and $M_4$ receptors than at other receptors.

Figure 9:
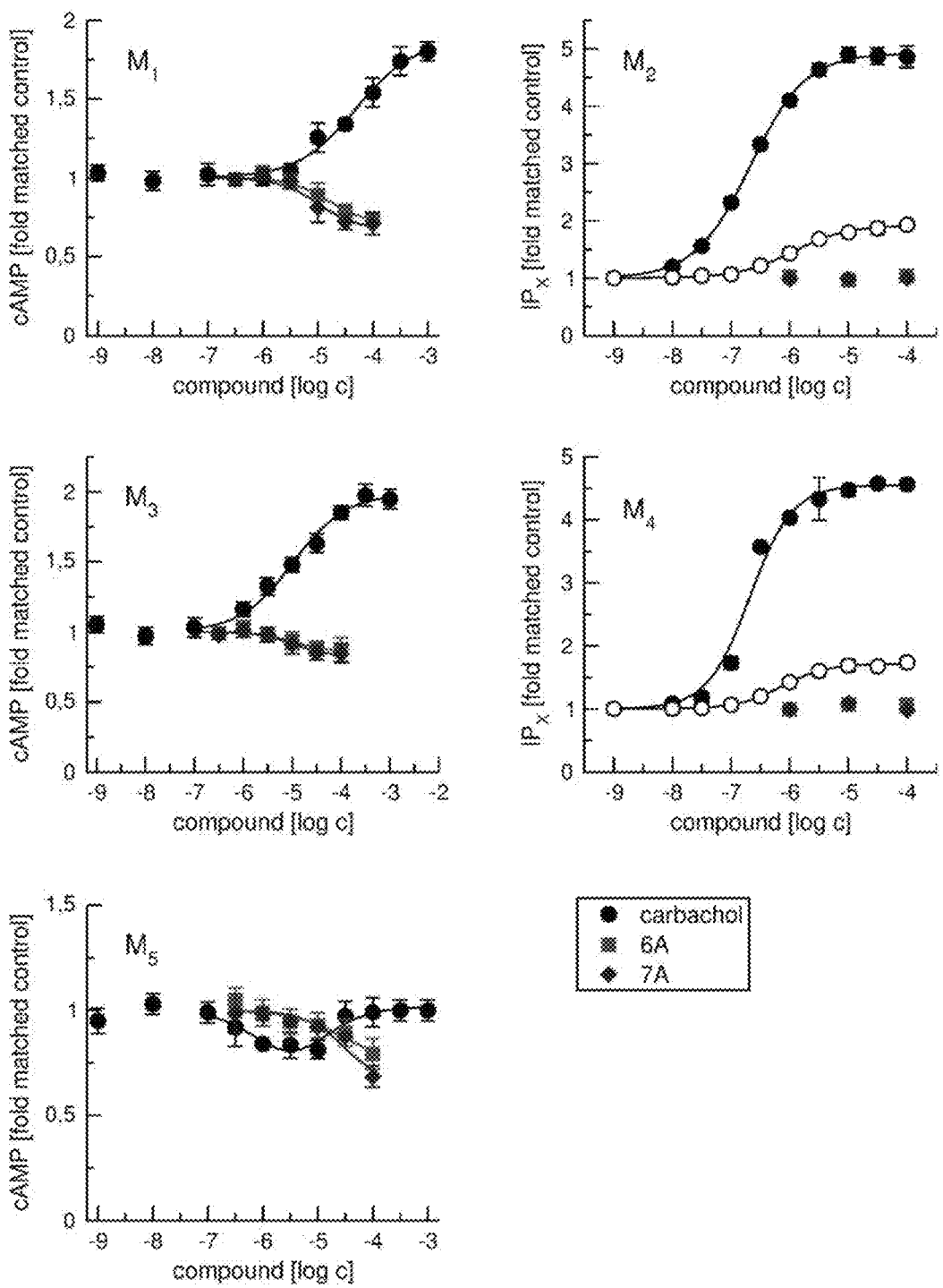
FIG. 9 is a series of graphs showing non-preferential functional responses to agonists in CHO cells that express individual subtypes of muscarinic receptors. Non-preferential signaling was measured, namely accumulation of forskolin-stimulated cAMP ($M_1$, $M_3$ and $M_5$) or IPX ($M_2$ and $M_4$ CHO cells) at non-transfected (open symbols) or $G_{15}$ G-protein transfected cells (closed symbols) after stimulation by increasing concentrations of carbachol (circles) or compounds 6A (squares) and 7A (diamonds). Levels of IPX and cAMP are expressed as of matched controls. Data are means±SD from 5 independent experiments performed in triplicates.

Muscarinic receptors are also able to stimulate non-preferential signalling pathways. The ability of the two most efficacious compounds 6A and 7A to activate non-preferential responses via muscarinic receptors was determined by measuring of forskolin-stimulated production of cAMP at $M_1$, $M_3$ and $M_5$ receptors or accumulation of $IP_X$ at $M_2$ and $M_4$ receptors co-transfected with promiscuous $G_{15}$ G-protein (FIG. 9). Carbachol activated non-preferential signalling pathways at all receptor subtypes. It increased cAMP level at $M_1$ and $M_3$ receptors (Gs) and stimulated accumulation of $IP_X$ ($G_{15}$) at $M_2$ and $M_4$ receptors. At $M_5$ receptors, carbachol inhibited forskolin-stimulated production of cAMP at nanomolar concentrations while at micromolar concentrations it stimulated cAMP production. In contrast to carbachol, compounds 6A and 7A inhibited cAMP production at $M_1$, $M_3$ and $M_5$ receptors but did not stimulate $IP_X$ accumulation at $M_2$ and $M_4$ receptors. Taking together all functional responses, both preferential and non-preferential, compounds 6A and 7A inhibited forskolin-stimulated production of cAMP at all receptor subtypes and did not stimulate the production of cAMP at any subtype. In contrast, carbachol-stimulated production of $IP_X$ and cAMP at all subtypes.

Figure 10:
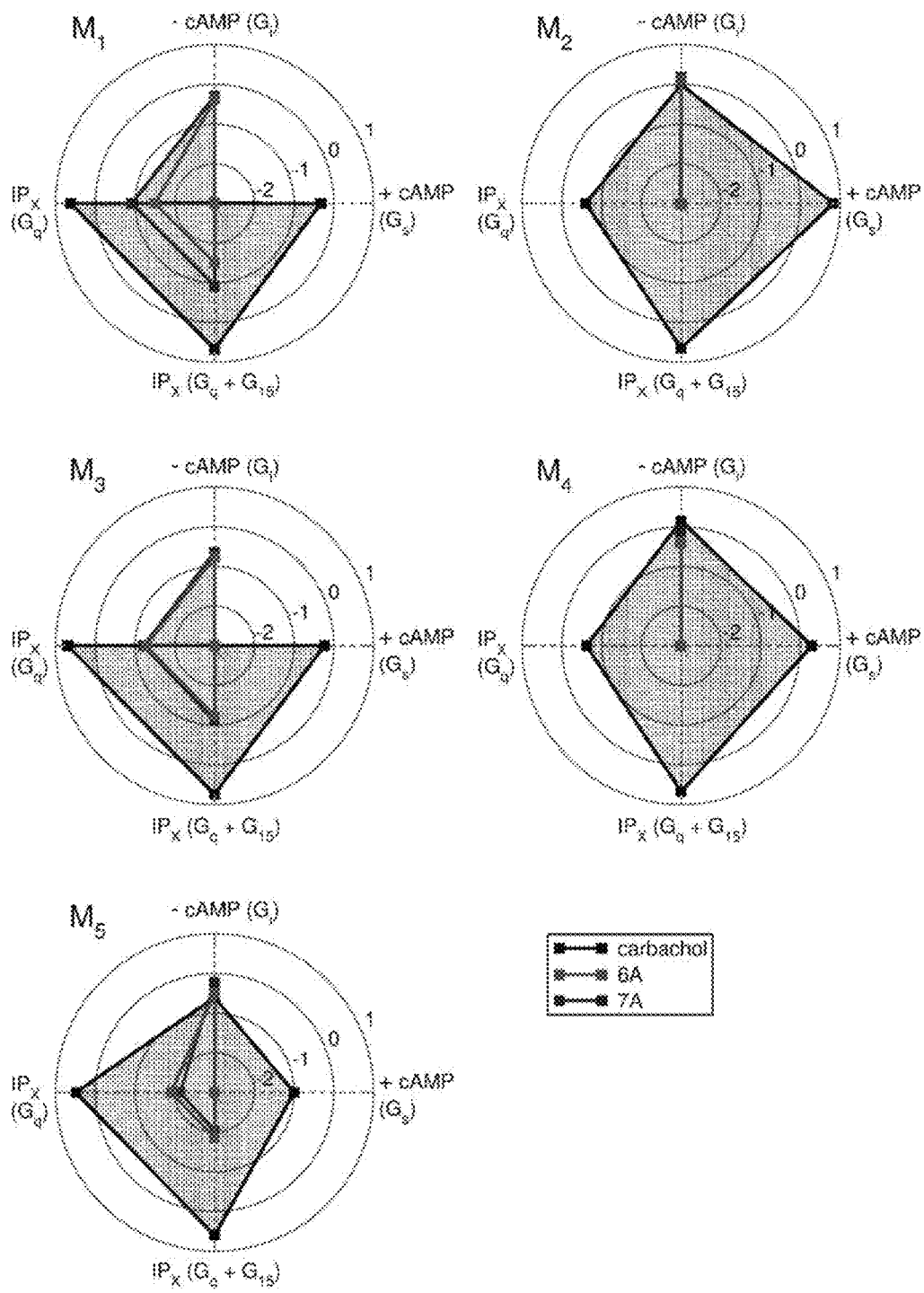
FIG. 10 is a series of polar plots of operational efficiency coefficient τ. Operational efficacy coefficient τ was determined from functional response curves in FIG. 8 and FIG. 9 by fitting Eq. 5. Logarithm of τ values of inhibition of forskolin-stimulated cAMP level (Gi), cAMP stimulation (Gs) and IPX stimulation at non-transfected (Gq) or $G_{15}$ G-protein transfected cells ($G_q+G_{15}$) of reference compound carbachol and compounds 6A and 7A are plotted.

To calculate the operational efficacy coefficient τ of preferential (FIG. 2) as well as non-preferential (FIG. 3) functional response to tested agonists, the system $E_{MAX}$ was determined from functional responses to the reference agonists carbachol, oxotremorine and pilocarpine according to the procedure described recently (Jakubik et al., Sci. Rep. 9:4637, 2019). As carbachol and oxotremorine did not inhibit forskolin-stimulated production of cAMP at $M_1$ and $M_3$ receptors, system $E_{MAX}$ for these systems was determined from functional responses to pilocarpine and compounds 6A and 7A. Then Eq. 5 was fitted to the experimental data. Values of the operational efficacy coefficient τ of carbachol and compounds 6A and 7A (Supplementary Information, Table 7 and 8) are plotted in FIG. 10. Intrinsic activities relative to carbachol $RA_i$ were calculated to analyze potential selectivity of 6A and 7A (Table 3, Supplementary Information Tables 7 and 8). Compounds 6A and 7A had the highest $RA_i$ at $M_2$ (6A, $M_2>M_3≈M_4≈M_5≈M_1$) or $M_2$ and $M_4$ receptors (7A: $M_2>M_4>M_1=M_3≈M_5$) (Table 3). The reference agonist carbachol was efficacious at stimulation of $IP_X$ ($G_q$) and cAMP ($G_s$) production at all subtypes and in lowering cAMP level at $M_2$, $M_4$ and $M_5$ receptors. Compounds 6A and 7A had no $G_s$ efficacy at any receptor subtype. Their $G_q$ efficacy was always lower than efficacy of carbachol. In contrast, their $G_i$ efficacy was (except $M_4$) always higher than efficacy of carbachol. Being $G_i$ efficacious at $M_1$ and $M_3$ receptors compounds 6A and 7A display an absolute $G_i$ bias, while carbachol has no $G_i$ efficacy at these receptors. Being solely efficacious at $G_i$ pathway at $M_2$ and $M_4$ receptors compounds 6A and 7A are also $G_i$ biased at these receptors (Table 3, Supplementary Information, Tables 7 and 8). At $M_5$ receptors compounds 6A and 7A exerted about 10-fold and 30-fold $G_i$ over $G_q+G_{15}$ bias, respectively.

Figure 11:
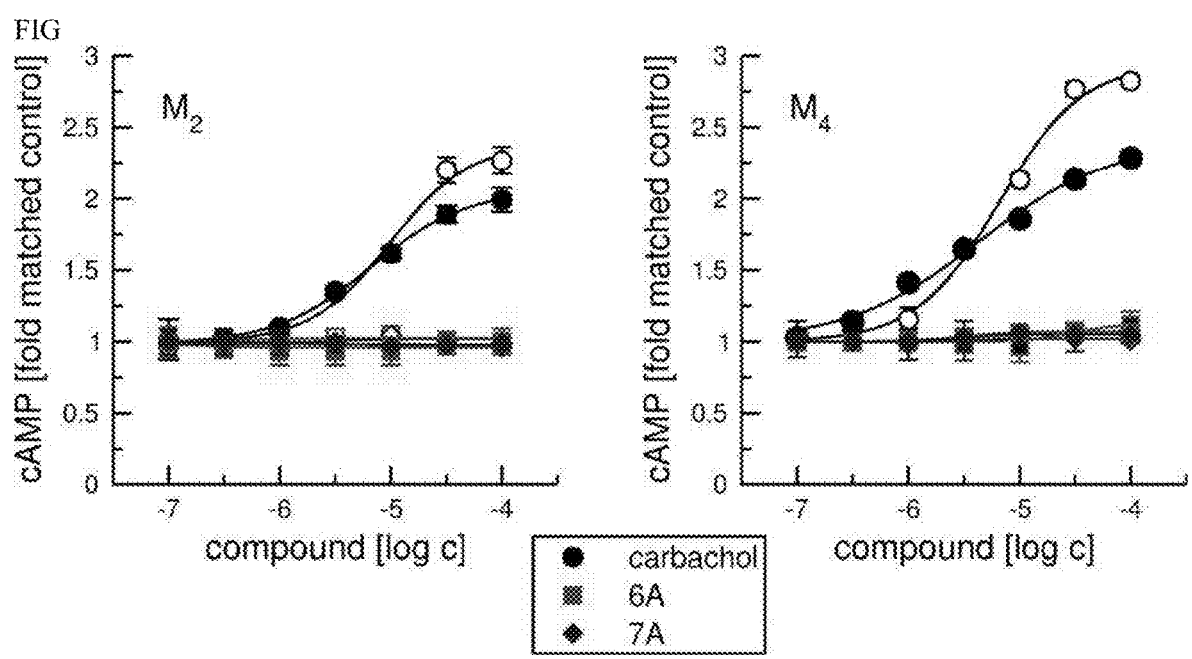
FIG. 11 is a pair of graphs showing accumulation of cAMP at PTX-treated CHO cells. Accumulation of cAMP was measured in CHO cells expressing $M_2$ (left) or $M_4$ receptors (right) that had been treated with pertussis toxin (PTX). Cells were stimulated by increasing concentrations of carbachol (circles), compound 6A (squares) or compound 7A (diamonds) in the presence (full symbols) or absence (open symbols) of 10 μM forskolin. Level of cAMP is expressed as folds of matched controls. Data are means±SD from 5 independent experiments performed in triplicates.
Figure 12:
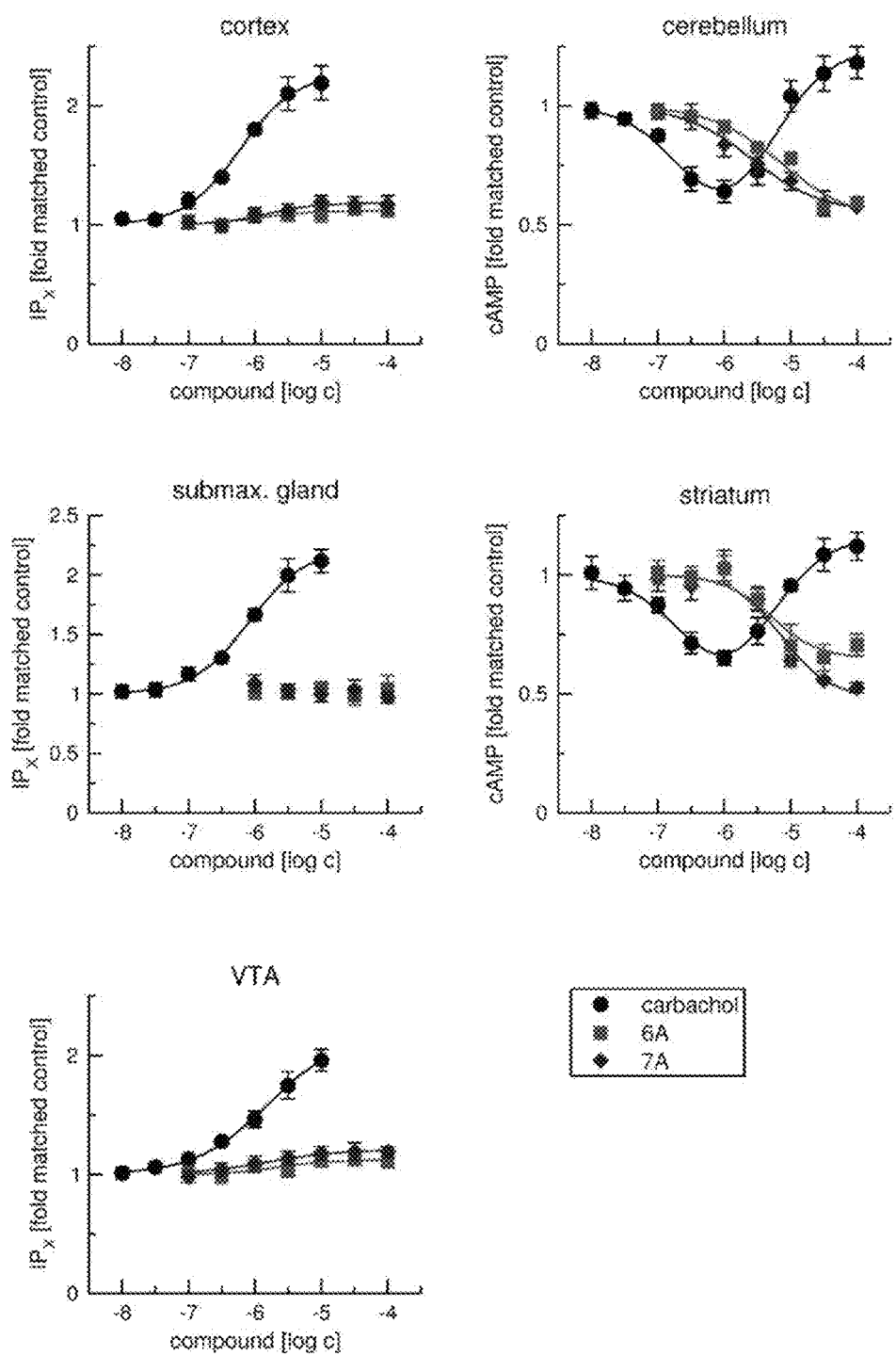
FIG. 12 is a series of graphs showing functional responses to agonists in dissipated rat tissues. Accumulation of $IP_X$ in brain cortex (upper left), submaxillary gland (middle left) and ventral tegmental area (VTA, lower left) or forskolin-stimulated cAMP in the cerebellum (upper right) and striatum (middle right) after stimulation by increasing concentrations of carbachol (circles) or compounds 6A (squares) and 7A (diamonds) was measured. Levels of $IP_X$ and cAMP are expressed as folds of matched controls. Data are means±SD from 5 independent experiments performed in triplicates.

To exclude the possibility that activation of the non-preferential $G_s$ pathway was obscured by activation of the preferential $G_{i/o}$ pathway, accumulation of cAMP was measured in CHO cells expressing $M_2$ or $M_4$ receptors where $G_{i/o}$ G-proteins were inactivated by pertussis toxin (PTX) treatment (FIG. 11). PTX treated cells were cultivated alongside with untreated cells. PTX treatment was successful as it abolished carbachol-mediated decrease in cAMP. In fact, carbachol caused about two-fold increase in forskolin-stimulated (FIG. 11, full circles) as well as basal (FIG. 10, open circles) accumulation of cAMP in PTX-treated cells. Carbachol $EC_{50}$ values in PTX treated cells were the same ($M_2$) or 3-times lower ($M_4$) than in non-treated cells. Unlike carbachol, compounds 6A and 7A did not change cAMP levels even after inactivation of $G_{i/o}$ G-proteins by PTX. Thus potential stimulatory (e.g. $G_s$-mediated) response to compounds 6A and 7A was not obscured by activation of $G_i$ G-proteins.

To exclude the possibility that the observed effects of compounds 6A and 7A are the result of overexpression in the heterologous system, functional response to the compounds was measured ex vivo in dissipated native rat tissues. Native tissues express about 10-times less muscarinic receptors than CHO cell lines (Supplementary Information, Table 9 vs. Table 4). Accumulation of $IP_X$ was measured in brain cortex, submaxillary gland, and ventral tegmental area (VTA) as brain cortex and submaxillary glands are rich in $M_1$ and in $M_3$ receptors, respectively, and VTA is the only region expressing significant amount of $M_5$ receptors. Accumulation of cAMP was measured in $M_2$-rich cerebellum and $M_4$-rich striatum. Carbachol produced profound accumulation of $IP_X$ in the cortex, submaxillary gland and VTA. In contrast to carbachol, compounds 6A and 7A produced no increase in $IP_X$ levels in submaxillary gland and led to negligible increase in $IP_X$ in the cortex and VTA (FIG. 6, left). In the cerebellum and striatum, carbachol caused transient decrease in forskolin-stimulated cAMP level at sub-micromolar concentrations followed by an increase at micromolar concentrations. In contrast to carbachol, compounds 6A and 7A caused only a decrease in cAMP level. $E_{MAX}$ of inhibition of cAMP synthesis in the cerebellum and striatum by compounds 6A and 7A was comparable to inhibition by carbachol. Taken together, compounds 6A and 7A only inhibited cAMP synthesis in dissipated tissues, being sometimes as efficacious as the full agonist carbachol.

Figure 13:
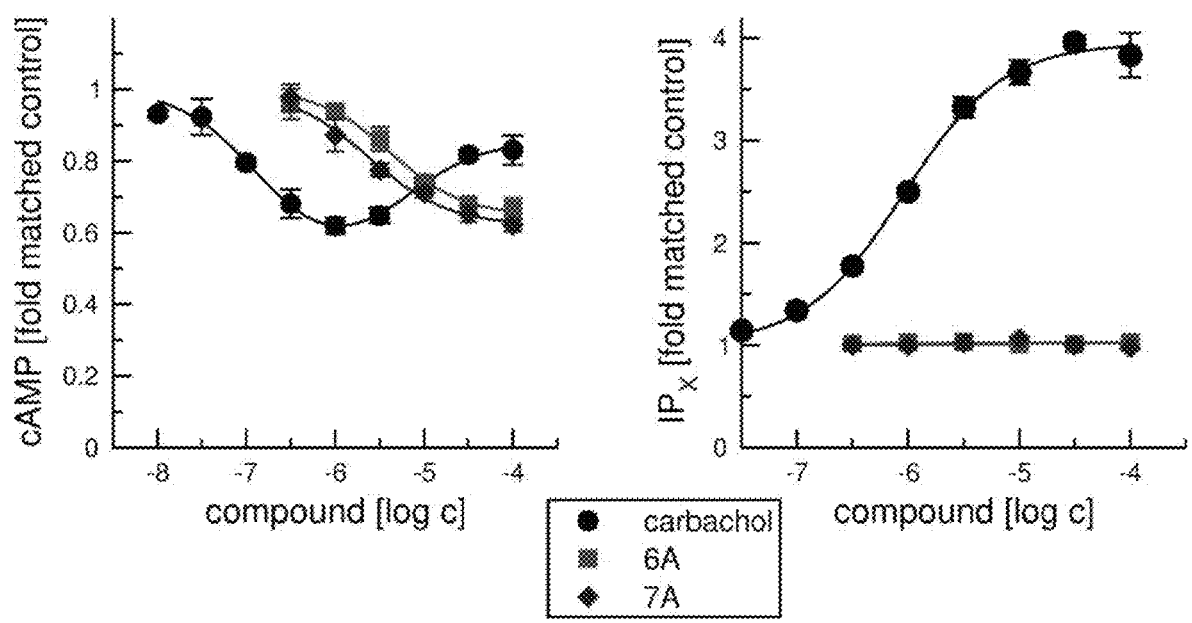
FIG. 13 is a pair of graphs showing functional responses to agonists in primary culture of smooth muscle cells. Accumulation of cAMP (left) or IPX (right) in primary culture of smooth muscle cells were measured after stimulation by increasing concentrations of carbachol (circles) or compounds 6A (squares) and 7A (diamonds). Levels of IPX and cAMP are expressed as folds of matched controls. Data are means±SD from 5 independent experiments performed in triplicates.

Effects of compounds 6A and 7A on both cAMP and $IP_X$ levels were also measured in primary cultures of rat aorta smooth muscle cells that naturally express mainly $M_2$ and to a lesser extent $M_3$ receptors. In this primary cell culture, carbachol caused a transient decrease in cAMP level (FIG. 13, left) as well as an increase in $IP_X$ level (FIG. 13, right). Similar to dissipated native tissues, compounds 6A and 7A only inhibited cAMP synthesis. Maximal inhibition of cAMP synthesis by compounds 6A and 7A was the same as inhibition by carbachol. Taken together, ex vivo results are in agreement with results obtained at CHO cells. Thus, pharmacological profile of 6A and 7A is not an artefact of heterologous high-expression system.

Figure 14:
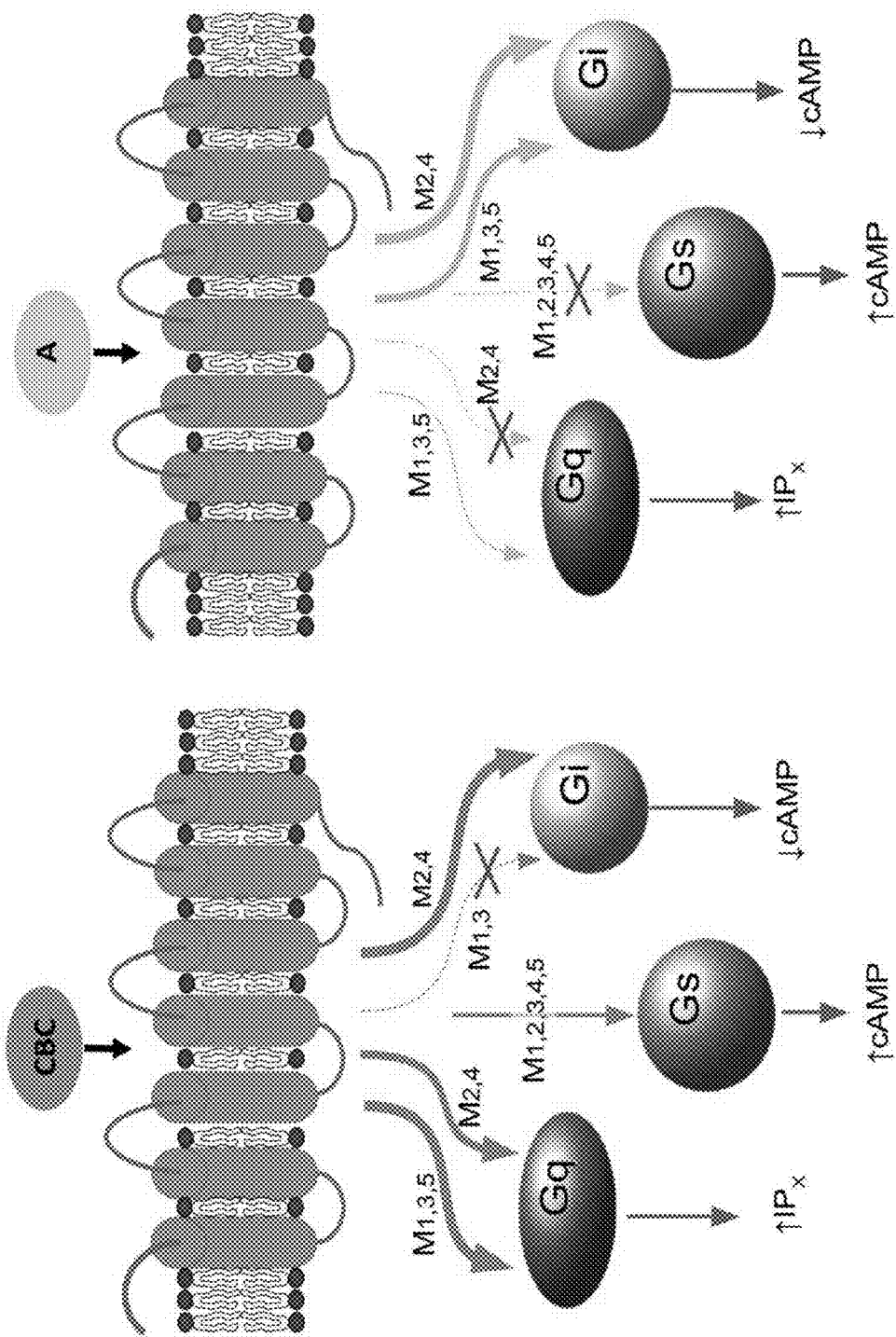
FIG. 14 is a scheme of signalling bias of novel compounds. Comparison of activation of Gi, Gq and Gs signalling pathways by carbachol (CBC, left) and compounds 6A and 7A (A, right) leading to inhibition of cAMP production (Gi) or stimulation of production of IPX (Gq) or of cAMP (Gs). Thickness of arrows denotes efficacy: Thick arrow—high efficacy, thin arrow—low efficacy, dotted arrow—no activity. Carbachol activates Gq and Gs pathways via all receptor subtypes and Gi pathway via M2 and M4. It has no Gi efficacy at M1 and M3. Compounds 6A and 7A activate Gi pathway with high efficacy via all subtypes and Gq pathway with low efficacy via M1, M3 and M5. They have no Gs efficacy at any subtype.

In conclusion, the development of novel muscarinic agonists that are selective for $M_2$ receptors and exhibit bias for Gi proteins, resulting in selective inhibition of production of cAMP (FIG. 14), is a major achievement.

TABLE 3

Efficacies of compounds 6A and 7A to elicit preferential response
Efficacies of compounds 6A and 7A to elicit preferential response
(stimulation of IPX production at $M_1$, $M_3$ and $M_5$ receptors and inhibition of cAMP production at $M_2$ and $M_4$ receptors are expressed as intrinsic activities relative to carbachol (RAi) and as Δlog(τ/KA) to carbachol.

| | 6A | | 7A | |
|---|---|---|---|---|
| | $RA_i$ | $\Delta\log(\tau/K_A)$ | $RA_i$ | $\Delta\log(\tau/K_A)$ |
| $M_1$ | 0.0010 ± 0.0001 | 2.98 ± 0.26 | 0.0111 ± 0.0002 | 1.96 ± 0.16 |
| $M_2$ | 0.067 ± 0.007* | 1.22 ± 0.08* | 0.140 ± 0.008* | 0.93 ± 0.09* |
| $M_3$ | 0.0058 ± 0.0005 | 2.23 ± 0.23 | 0.011 ± 0.001 | 1.94 ± 0.20 |
| $M_4$ | 0.0046 ± 0.0004 | 2.15 ± 0.16 | 0.0209 ± 0.0011 | 1.58 ± 0.22 |
| $M_5$ | 0.0025 ± 0.0008 | 2.60 ± 0.82 | 0.0007 ± 0.0002 | 3.17 ± 0.88 |

*significantly different (P < 0.01) from other subtypes according ANOVA and Tukey post-test. Values are means ± SD from 5 independent experiments performed in triplicates.

Supplemental Information

TABLE 4

Binding, equilibrium dissociation constant KD and maximum binding capacity BMAX.
Parameters of [$^3$H]NMS binding, equilibrium dissociation constant $K_D$ and maximum binding capacity $B_{MAX}$ at the cell lines expressing individual subtypes of muscarinic receptors were determined in the saturation experiments. $K_D$ is expressed as negative logarithm and $B_{MAX}$ is expressed in pmol of binding sites per mg of membrane proteins.

| Subtype | $pK_D$ | $B_{MAX}$ [pmol/mg] |
|---|---|---|
| $M_1$ | 10.00 ± 0.04 | 5.5 ± 0.1 |
| $M_2$ | 9.39 ± 0.02 | 8.0 ± 0.9 |
| $M_3$ | 10.03 ± 0.01 | 8.0 ± 0.1 |
| $M_4$ | 10.05 ± 0.08 | 10 ± 2 |
| $M_5$ | 9.79 ± 0.05 | 1.2 ± 0.1 |

TABLE 5

| | $R_1$ | $R_2$ | $R_3$ | $M_1$ | $M_2$ | $M_3$ | $M_4$ | $M_5$ |
|---|---|---|---|---|---|---|---|---|
| 6A | —H | —H | —H | 4.35 ± 0.07 | 4.37 ± 0.06 | 4.43 ± 0.03 | 4.27 ± 0.02 | 4.3 ± 0.1 |
| 6B | —H | —CH$_3$ | —H | 4.6 ± 0.1 | 4.99 ± 0.07* | 4.64 ± 0.04 | 4.54 ± 0.05 | 4.62 ± 0.07 |
| 6C | —H | —Br | —H | 5.12 ± 0.02* | 5.0 ± 0.1 | 4.85 ± 0.06 | 4.90 ± 0.06 | 4.89 ± 0.04 |
| 6E | —H | —CH$_3$ | —H | 4.5 ± 0.1 | 4.9 ± 0.1* | 4.3 ± 0.1 | 4.5 ± 0.1 | 4.5 ± 0.1 |
| 7A | —CH$_3$ | —H | —H | 4.95 ± 0.07 | 5.1 ± 0.1 | 5.1 ± 0.1 | 5.1 ± 0.1 | 5.0 ± 0.2 |
| 7B | —CH$_3$ | —CH$_3$ | —H | 5.4 ± 0.1 | 5.64 ± 0.07* | 5.28 ± 0.05 | 5.36 ± 0.08 | 5.47 ± 0.04 |
| 7C | —CH$_3$ | —Br | —H | 5.82 ± 0.03 | 6.03 ± 0.03 | 5.69 ± 0.07 | 5.84 ± 0.07 | 6.01 ± 0.08 |
| 7D | —CH$_3$ | —Cl | —H | 5.86 ± 0.08 | 6.16 ± 0.06* | 5.47 ± 0.02 | 5.51 ± 0.06 | 5.77 ± 0.05 |

*significantly different (P < 0.01) from other subtypes according ANOVA and Tukey post-test.
Inhibition constants ($K_I$) of compounds are expressed as negative logarithms of mean ± SD of 6 independent experiments performed in quadruplicates.
About 20 % binding to $M_2$ and 10 % of binding to $M_4$ of compounds 6B and 7B occurred with high affinity with $pK_I$ ranging from 7.5 ± 01 (6B at $M_2$) to 7.7 ± 01(6B at $M_4$).
Compound 6E, Me-group is at position 3 of the thiophene ring, all others at position 5).

TABLE 6

Inhibition constants of reference agonists

| | site | $M_1$ | $M_2$ | $M_3$ | $M_4$ | $M_5$ |
|---|---|---|---|---|---|---|
| carbachol | high | 7.0 ± 0.1 | 6.9 ± 0.1 | 7.1 ± 0.1 | 6.9 ± 0.1 | 6.9 ± 0.1 |
| | low | 5.20 ± 0.04 | 5.02 ± 0.05 | 5.15 ± 0.04 | 5.00 ± 0.05 | 5.03 ± 0.05 |
| oxotremorine | high | 8.1 ± 0.1 | 7.9 ± 0.1 | 8.0 ± 0.1 | 7.9 ± 0.1 | 7.9 ± 0.1 |
| | low | 6.43 ± 0.04* | 6.24 ± 0.03 | 6.35 ± 0.04 | 6.21 ± 0.03 | 6.27 ± 0.04 |
| pilocarpine | high | 7.4 ± 0.1 | 7.2 ± 0.1 | 7.3 ± 0.1 | 7.2 ± 0.1 | 7.2 ± 0.1 |
| | low | 5.83 ± 0.04 | 5.63 ± 0.04 | 5.78 ± 0.04 | 5.61 ± 0.04 | 5.68 ± 0.04 |

*significantly different (P < 0.01) from other subtypes according ANOVA and Tukey post-test.
Inhibition constants ($K_I$) of compounds are expressed as negative logarithms of mean ± SD of 6 independent experiments performed in quadruplicates.

TABLE 7

Parameters of preferential functional response $M_1$   $E_{MAX}$ = 34 ± 3 [fold over basal]

| (↑$P_X$) | $pEC_{50}$ | $E'_{MAX}$ | $pK_A$ | τ | RAi | $\Delta\log(\tau/K_A)$ |
|---|---|---|---|---|---|---|
| carbachol | 6.65 ± 0.04 | 29 ± 3 | 5.9 ± 0.1 | 4.71 ± 0.40 | 1 | 0 |
| oxotremorine | 7.28 ± 0.04 | 25 ± 2 | 6.7 ± 0.1 | 2.55 ± 0.25 | 3.71 ± 0.29 | −0.57 ± 0.06 |
| pilocarpine | 6.15 ± 0.05 | 20 ± 2 | 5.8 ± 0.1 | 1.24 ± 0.08 | 0.212 ± 0.022 | 0.67 ± 0.04 |
| 6A | 5.1 ± 0.1 | 2.0 ± 0.2 | 5.1 ± 0.2 | 0.03 ± 0.01 | 0.0010 ± 0.0001 | 2.98 ± 0.26 |
| 6B | 4.8 ± 0.1 | 2.0 ± 0.2 | 4.8 ± 0.2 | 0.03 ± 0.01 | 0.0005 ± 0.0001 | 3.28 ± 0.38 |
| 6C | 5.46 ± 0.05 | 2.1 ± 0.2 | 5.4 ± 0.2 | 0.03 ± 0.01 | 0.0024 ± 0.0002 | 2.62 ± 0.36 |
| 6E | n.d. | n.d. | n.c. | n.c. | 0 | n.c. |
| 7A | 5.58 ± 0.03 | 4.6 ± 0.4 | 5.5 ± 0.1 | 0.12 ± 0.01 | 0.0111 ± 0.0002 | 1.96 ± 0.16 |
| 7B | 5.30 ± 0.05 | 3.9 ± 0.4 | 5.3 ± 0.1 | 0.09 ± 0.01 | 0.0058 ± 0.0007 | 2.24 ± 0.18 |
| 7C | 5.6 ± 0.2 | 1.8 ± 0.2 | 5.6 ± 0.2 | 0.02 ± 0.01 | 0.0024 ± 0.0004 | 2.62 ± 0.18 |
| 7D | 5.47 ± 0.05 | 7.9 ± 0.8 | 5.4 ± 0.1 | 0.26 ± 0.03 | 0.0165 ± 0.0003 | 1.78 ± 0.21 |

TABLE 7-continued

Parameters of preferential functional response

| $M_2$ | $E_{MAX}$ = 88 ± 2 [% inhibition] | | | | | |
|---|---|---|---|---|---|---|
| ($\downarrow$cAMP) | $pEC_{50}$ | $E'_{MAX}$ | $pK_A$ | $\tau$ | RAi | $\Delta\log(\tau/K_A)$ |
| carbachol | 7.42 ± 0.04 | 44 ± 1 | 7.1 ± 0.1 | 1.0 ± 0.1 | 1 | 0 |
| oxotremorine | 8.24 ± 0.04 | 43 ± 1 | 7.9 ± 0.1 | 0.96 ± 0.08 | 6.34 ± 0.15 | −0.81 ± 0.01 |
| pilocarpine | 7.15 ± 0.04 | 29 ± 1 | 7.0 ± 0.1 | 0.49 ± 0.05 | 0.279 ± 0.010 | 0.45 ± 0.05 |
| 6A | 6.14 ± 0.05 | 50 ± 2 | 5.8 ± 0.1 | 1.32 ± 0.08 | 0.067 ± 0.007 | 1.22 ± 0.08 |
| 6B | 5.04 ± 0.05 | 47 ± 2 | 4.7 ± 0.1 | 1.15 ± 0.08 | 0.0047 ± 0.0004 | 2.35 ± 0.16 |
| 6C | 5.66 ± 0.06 | 24 ± 1 | 5.5 ± 0.1 | 0.38 ± 0.04 | 0.0070 ± 0.0006 | 2.02 ± 0.22 |
| 6E | n.d. | n.d. | n.c. | n.c. | 0 | n.c. |
| 7A | 6.41 ± 0.05 | 53 ± 2 | 6.0 ± 0.1 | 1.51 ± 0.15 | 0.140 ± 0.008 | 0.93 ± 0.09 |
| 7B | 6.03 ± 0.05 | 36 ± 1 | 5.8 ± 0.1 | 0.69 ± 0.07 | 0.029 ± 0.002 | 1.48 ± 0.15 |
| 7C | 5.79 ± 0.03 | 38 ± 2 | 5.5 ± 0.1 | 0.76 ± 0.08 | 0.018 ± 0.002 | 1.69 ± 0.09 |
| 7D | 5.41 ± 0.04 | 40 ± 2 | 5.2 ± 0.1 | 0.83 ± 0.08 | 0.008 ± 0.001 | 2.05 ± 0.19 |

| $M_3$ | $E_{MAX}$ = 29 ± 3 [fold over basal] | | | | | |
|---|---|---|---|---|---|---|
| ($\uparrow P_X$) | $pEC_{50}$ | $E'_{MAX}$ | $pK_A$ | $\tau$ | RAi | $\Delta\log(\tau/K_A)$ |
| carbachol | 6.35 ± 0.04 | 25 ± 3 | 5.5 ± 0.1 | 5.44 ± 0.50 | 1 | 0 |
| oxotremorine | 7.02 ± 0.04 | 22 ± 2 | 6.4 ± 0.1 | 2.97 ± 0.30 | 4.14 ± 0.38 | −0.62 ± 0.06 |
| pilocarpine | 5.88 ± 0.04 | 18 ± 2 | 5.5 ± 0.1 | 1.46 ± 0.08 | 0.238 ± 0.027 | 0.62 ± 0.03 |
| 6A | 5.3 ± 0.1 | 2.5 ± 0.2 | 5.3 ± 0.2 | 0.06 ± 0.01 | 0.0058 ± 0.0005 | 2.23 ± 0.23 |
| 6B | 4.5 ± 0.1 | 2.0 ± 0.2 | 4.8 ± 0.2 | 0.04 ± 0.01 | 0.0006 ± 0.0001 | 3.24 ± 0.34 |
| 6C | 5.3 ± 0.2 | 1.8 ± 0.1 | 5.4 ± 0.2 | 0.03 ± 0.01 | 0.0029 ± 0.0004 | 2.53 ± 0.33 |
| 6E | n.d. | n.d. | n.c. | n.c. | 0 | n.c. |
| 7A | 5.5 ± 0.1 | 3.0 ± 0.3 | 5.5 ± 0.1 | 0.08 ± 0.01 | 0.011 ± 0.001 | 1.94 ± 0.20 |
| 7B | 5.08 ± 0.06 | 4.4 ± 0.4 | 5.3 ± 0.1 | 0.14 ± 0.01 | 0.0077 ± 0.0008 | 2.11 ± 0.12 |
| 7C | 5.6 ± 0.2 | 1.6 ± 0.1 | 5.6 ± 0.2 | 0.02 ± 0.01 | 0.0042 ± 0.0005 | 2.38 ± 0.66 |
| 7D | 5.5 ± 0.2 | 1.8 ± 0.1 | 5.4 ± 0.2 | 0.03 ± 0.01 | 0.0050 ± 0.0006 | 2.30 ± 0.45 |

| $M_4$ | $E_{MAX}$ = 89 ± 2 [% inhibition] | | | | | |
|---|---|---|---|---|---|---|
| ($\downarrow$cAMP) | $pEC_{50}$ | $E'_{MAX}$ | $pK_A$ | $\tau$ | RAi | $\Delta\log(\tau/K_A)$ |
| carbachol | 7.20 ± 0.04 | 55 ± 2 | 6.8 ± 0.1 | 1.41 ± 0.08 | 1 | 0 |
| oxotremorine | 7.85 ± 0.04 | 48 ± 2 | 7.5 ± 0.1 | 1.17 ± 0.08 | 3.81 ± 0.16 | −0.62 ± 0.08 |
| pilocarpine | 7.04 ± 0.04 | 36 ± 1 | 6.8 ± 0.1 | 0.68 ± 0.06 | 0.395 ± 0.010 | 0.32 ± 0.03 |
| 6A | 5.37 ± 0.07 | 25 ± 2 | 5.2 ± 0.1 | 0.39 ± 0.04 | 0.0046 ± 0.0004 | 2.15 ± 0.16 |
| 6B | 5.01 ± 0.04 | 25 ± 2 | 4.9 ± 0.1 | 0.39 ± 0.04 | 0.0020 ± 0.0002 | 2.51 ± 0.20 |
| 6C | 5.67 ± 0.08 | 13 ± 1 | 5.6 ± 0.1 | 0.38 ± 0.04 | 0.0041 ± 0.005 | 2.13 ± 0.12 |
| 6E | n.d. | n.d. | n.c. | n.c. | 0 | n.c. |
| 7A | 5.75 ± 0.05 | 39 ± 2 | 5.5 ± 0.1 | 0.78 ± 0.08 | 0.0209 ± 0.0011 | 1.58 ± 0.22 |
| 7B | 5.54 ± 0.02 | 30 ± 1 | 5.4 ± 0.1 | 0.51 ± 0.05 | 0.0087 ± 0.0009 | 1.90 ± 0.18 |
| 7C | 5.62 ± 0.04 | 11 ± 1 | 5.6 ± 0.1 | 0.14 ± 0.01 | 0.0030 ± 0.0003 | 2.26 ± 0.16 |
| 7D | 5.33 ± 0.05 | 28 ± 1 | 5.2 ± 0.1 | 0.46 ± 0.05 | 0.0048 ± 0.0005 | 2.14 ± 0.19 |

| $M_5$ | $E_{MAX}$ = 21 ± 2 [fold over basal] | | | | | |
|---|---|---|---|---|---|---|
| ($\uparrow P_X$) | $pEC_{50}$ | $E'_{MAX}$ | $pK_A$ | $\tau$ | RAi | $\Delta\log(\tau/K_A)$ |
| carbachol | 6.49 ± 0.04 | 17 ± 2 | 5.8 ± 0.1 | 4.02 ± 0.40 | 1 | 0 |
| oxotremorine | 7.15 ± 0.04 | 16 ± 1 | 6.6 ± 0.1 | 2.60 ± 0.30 | 4.12 ± 0.26 | −0.62 ± 0.07 |
| pilocarpine | 5.97 ± 0.04 | 12 ± 1 | 5.7 ± 0.1 | 1.05 ± 0.08 | 0.191 ± 0.017 | 0.71 ± 0.05 |
| 6A | 5.8 ± 0.1 | 1.19 ± 0.04 | n.c. | n.c. | 0.0025 ± 0.0008 | 3.16 ± 0.88 |
| 6B | 4.82 ± 0.04 | 1.7 ± 0.1 | 4.8 ± 0.1 | 0.04 ± 0.01 | 0.0009 ± 0.0005 | 3.04 ± 0.66 |
| 6C | 5.12 ± 0.06 | 1.36 ± 0.08 | 5.1 ± 0.1 | 0.02 ± 0.01 | 0.0009 ± 0.0003 | 3.03 ± 0.95 |
| 6E | n.d. | n.d. | n.c. | n.c. | 0 | n.c. |
| 7A | 5.1 ± 0.1 | 1.28 ± 0.05 | n.c. | n.c. | 0.0007 ± 0.0001 | 2.60 ± 0.82 |
| 7B | 5.36 ± 0.08 | 1.47 ± 0.07 | 5.3 ± 0.2 | 0.02 ± 0.01 | 0.0021 ± 0.0009 | 2.67 ± 0.41 |
| 7C | 5.5 ± 0.1 | 1.19 ± 0.04 | n.c. | n.c. | 0.0013 ± 0.0005 | n.c. |
| 7D | 5.01 ± 0.04 | 3.5 ± 0.2 | 4.9 ± 0.1 | 0.14 ± 0.01 | 0.0049 ± 0.0006 | 2.31 ± 0.50 | n.c., not calculated;
n.d., not determined.

Parameters of functional response (level of forskolin-stimulated cAMP, $M_2$ and $M_4$, or accumulation of inositol phosphates, $M_1$, $M_3$ and $M_5$) are listed.

Half-efficient concentration ($EC_{50}$) is expressed as negative logarithm and apparent maximal response to agonist ($E'_{MAX}$) is expressed as folds over basal ($M_1$, $M_3$ and $M_5$) or as % of inhibition ($M_2$ and $M_4$).

Hill coefficients are equal to one.

Values are means ± SD from 5 independent experiments performed in triplicates.

TABLE 8

Parameters of functional responses. Parameters of functional responses (cAMP and $IP_X$) upon stimulation of carbachol, oxotremorine, pilocarpine or compound 6A or 7A.

| $M_1G_i$ | $E_{MAX} = 88 \pm 2$ [% of inhibition] | | | | | |
|---|---|---|---|---|---|---|
| ($\downarrow$cAMP) | $pEC_{50}$ | $E'_{MAX}$ | $pK_A$ | $\tau$ | RAi | $\Delta\log(\tau/K_A)$ |
| carbachol | n.d. | n.d. | n.c. | n.c. | | n.c. |
| oxotremorine | n.d. | n.d. | n.c. | n.c. | | n.c. |
| pilocarpine | 6.7 ± 0.1 | 8 ± 1 | 6.6 ± 0.2 | 0.10 ± 0.02 | +inf. | n.c. |
| 6A | 4.93 ± 0.05 | 26 ± 2 | 4.8 ± 0.1 | 0.42 ± 0.04 | +inf. | n.c. |
| 7A | 5.10 ± 0.05 | 30 ± 3 | 4.9 ± 0.1 | 0.52 ± 0.05 | +inf. | n.c. |

| $M_1G_q$ | $E_{MAX} = 34.5 \pm 3$ [fold increase] | | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 6.63 ± 0.04 | 28 ± 3 | 5.9 ± 0.1 | 4.2 ± 0.4 | 1 | 0 |
| oxotremorine | 7.26 ± 0.04 | 25 ± 2 | 6.7 ± 0.1 | 2.6 ± 0.3 | 3.84 ± 0.28 | −0.58 ± 0.05 |
| pilocarpine | 6.13 ± 0.05 | 20 ± 2 | 5.8 ± 0.1 | 1.3 ± 0.1 | 0.219 ± 0.033 | 0.66 ± 0.05 |
| 6A | 5.1 ± 0.1 | 2.0 ± 0.2 | 5.1 ± 0.2 | 0.03 ± 0.01 | 0.0011 ± 0.0007 | 2.96 ± 0.86 |
| 7A | 5.58 ± 0.03 | 4.6 ± 0.4 | 5.5 ± 0.1 | 0.12 ± 0.01 | 0.012 ± 0.006 | 1.93 ± 0.25 |

| $M_1G_q + G_{15}$ | $E_{MAX} = 34 \pm 3$ [fold increase] | | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 6.65 ± 0.04 | 29 ± 3 | 5.9 ± 0.10 | 4.7 ± 0.4 | 1 | 0 |
| oxotremorine | 7.28 ± 0.04 | 25 ± 2 | 6.7 ± 0.1 | 2.6 ± 0.3 | 3.71 ± 0.29 | −0.57 ± 0.06 |
| pilocarpine | 6.15 ± 0.05 | 20 ± 2 | 5.8 ± 0.1 | 1.2 ± 0.1 | 0.212 ± 0.022 | 0.67 ± 0.04 |
| 6A | 5.1 ± 0.1 | 2.0 ± 0.2 | 5.1 ± 0.2 | 0.03 ± 0.01 | 0.0010 ± 0.0001 | 2.98 ± 0.26 |
| 7A | 5.58 ± 0.03 | 4.6 ± 0.4 | 5.5 ± 0.1 | 0.12 ± 0.01 | 0.0111 ± 0.0002 | 1.96 ± 0.16 |

| $M_1G_s$ | $E_{MAX} = 3.8 \pm 0.3$ [fold increase] | | | | | |
|---|---|---|---|---|---|---|
| ($\uparrow$cAMP) | $pEC_{50}$ | $E'_{MAX}$ | $pK_A$ | $\tau$ | RAi | $\Delta\log(\tau/K_A)$ |
| carbachol | 4.30 ± 0.07 | 1.88 ± 0.08 | 4.13 ± 0.08 | 0.46 ± 0.05 | 1 | 0 |
| oxotremorine | 4.95 ± 0.06 | 1.77 ± 0.08 | 4.8 ± 0.1 | 0.38 ± 0.04 | 3.91 ± 0.22 | −0.59 ± 0.06 |
| pilocarpine | 4.1 ± 0.1 | 1.38 ± 0.04 | 4.0 ± 0.2 | 0.16 ± 0.03 | 0.272 ± 0.035 | 0.565 ± 0.058 |
| 6A | n.d. | n.d. | n.c. | n.c. | 0 | n.c. |
| 7A | n.d. | n.d. | n.c. | n.c. | 0 | n.c. |

| $M_2G_i$ | $E_{MAX} = 88 \pm 2$ [% inhibition] | | | | | |
|---|---|---|---|---|---|---|
| ($\downarrow$cAMP) | $pEC_{50}$ | $E'_{MAX}$ | $pK_A$ | $\tau$ | RAi | $\Delta\log(\tau/K_A)$ |
| carbachol | 7.42 ± 0.04 | 44 ± 1 | 7.1 ± 0.1 | 1.0 ± 0.1 | 1 | 0 |
| oxotremorine | 8.24 ± 0.04 | 43 ± 1 | 7.9 ± 0.1 | 1.0 ± 0.1 | 6.34 ± 0.15 | −0.81 ± 0.01 |
| pilocarpine | 7.15 ± 0.04 | 29 ± 1 | 7.0 ± 0.1 | 0.49 ± 0.05 | 0.279 ± 0.010 | 0.45 ± 0.05 |
| 6A | 6.14 ± 0.05 | 50 ± 2 | 5.8 ± 0.1 | 1.3 ± 0.1 | 0.067 ± 0.007 | 1.22 ± 0.08 |
| 7A | 6.41 ± 0.05 | 53 ± 2 | 6.0 ± 0.1 | 1.5 ± 0.2 | 0.140 ± 0.008 | 0.93 ± 0.09 |

| $M_2G_q$ | $E_{MAX} = 5.5 \pm 0.4$ [fold over basal] | | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 6.01 ± 0.04 | 1.91 ± 0.07 | 5.9 ± 0.1 | 0.2 ± 0.1 | 1 | 0 |
| oxotremorine | 6.68 ± 0.05 | 1.60 ± 0.05 | 6.6 ± 0.1 | 0.2 ± 0.1 | 3.08 ± 0.28 | −0.49 ± 0.05 |
| pilocarpine | 5.82 ± 0.05 | 1.27 ± 0.05 | 5.8 ± 0.1 | 0.06 ± 0.03 | 0.192 ± 0.018 | 0.72 ± 0.05 |
| 6A | n.d. | n.d. | n.c. | n.c. | 0 | n.c. |
| 7A | n.d. | n.d. | n.c. | n.c. | 0 | n.c. |

| $M_2G_q \pm G_{15}$ | $E_{MAX} = 5.8 \pm 0.4$ [fold over basal] | | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 6.67 ± 0.05 | 4.9 ± 0.3 | 5.9 ± 0.1 | 4.5 ± 0.5 | 1 | 0 |
| oxotremorine | 7.15 ± 0.05 | 4.1 ± 0.3 | 6.7 ± 0.1 | 1.9 ± 0.2 | 2.41 ± 0.22 | −0.38 ± 0.05 |
| pilocarpine | 6.07 ± 0.05 | 3.3 ± 0.2 | 5.8 ± 0.1 | 0.9 ± 0.1 | 0.146 ± 0.013 | 0.84 ± 0.08 |
| 6A | n.d. | n.d. | n.c. | n.c. | 0 | n.c. |
| 7A | n.d. | n.d. | n.c. | n.c. | 0 | n.c. |

| $M_2G_s$ | $E_{MAX} = 4.1 \pm 0.3$ [fold increase] | | | | | |
|---|---|---|---|---|---|---|
| ($\uparrow$cAMP) | $pEC_{50}$ | $E'_{MAX}$ | $pK_A$ | $\tau$ | RAi | $\Delta\log(\tau/K_A)$ |
| carbachol | 5.42 ± 0.04 | 3.6 ± 0.2 | 4.5 ± 0.1 | 6.6 ± 0.5 | 1 | 0 |
| oxotremorine | 5.94 ± 0.04 | 3.1 ± 0.2 | 5.4 ± 0.1 | 2.3 ± 0.2 | 2.65 ± 0.018 | −0.42 ± 0.04 |
| pilocarpine | 5.02 ± 0.05 | 2.0 ± 0.1 | 4.9 ± 0.1 | 0.50 ± 0.06 | 0.152 ± 0.009 | 0.82 ± 0.08 |

TABLE 8-continued

Parameters of functional responses. Parameters of functional responses (cAMP and $IP_X$) upon stimulation of carbachol, oxotremorine, pilocarpine or compound 6A or 7A.

| | | | | | | |
|---|---|---|---|---|---|---|
| 6A | n.d. | n.d. | n.c. | n.c. | 0 | n.c. |
| 7A | n.d. | n.d. | n.c. | n.c. | 0 | n.c. |

| $M_3G_i$ | | $E_{MAX} = 88 \pm 2$ [% of inhibition] | | | | |
|---|---|---|---|---|---|---|
| ($\downarrow$cAMP) | $pEC_{50}$ | $E'_{MAX}$ | $pK_A$ | $\tau$ | RAi | $\Delta\log(\tau/K_A)$ |
| carbachol | n.d. | n.d. | n.c. | n.c. | | n.c. |
| oxotremorine | n.d. | n.d. | n.c. | n.c. | | n.c. |
| pilocarpine | 6.4 ± 0.1 | 9 ± 1 | 6.4 ± 0.2 | 0.11 ± 0.02 | +inf. | n.c. |
| 6A | 5.11 ± 0.07 | 13 ± 1 | 5.0 ± 0.1 | 0.17 ± 0.02 | +inf. | n.c. |
| 7A | 5.06 ± 0.06 | 16 ± 1 | 5.0 ± 0.1 | 0.22 ± 0.02 | +inf. | n.c. |

| $M_3G_q + G_{15}$ | | $E_{MAX} = 29 \pm 3$ [fold over basal] | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 6.33 ± 0.04 | 25 ± 3 | 5.5 ± 0.1 | 5.0 ± 0.5 | 1 | 0 |
| oxotremorine | 7.00 ± 0.04 | 22 ± 2 | 6.4 ± 0.1 | 2.9 ± 0.3 | 4.14 ± 0.38 | −0.62 ± 0.06 |
| pilocarpine | 5.86 ± 0.04 | 18 ± 2 | 5.5 ± 0.1 | 1.4 ± 0.1 | 0.238 ± 0.027 | 0.62 ± 0.03 |
| 6A | 5.3 ± 0.1 | 2.5 ± 0.2 | 5.3 ± 0.2 | 0.06 ± 0.01 | 0.0058 ± 0.0005 | 2.23 ± 0.23 |
| 7A | 5.5 ± 0.1 | 3.0 ± 0.3 | 5.5 ± 0.1 | 0.08 ± 0.01 | 0.011 ± 0.001 | 1.94 ± 0.20 |

| $M_3G_q$ | | $E_{MAX} = 29 \pm 3$ [fold over basal] | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 6.35 ± 0.04 | 25 ± 3 | 5.5 ± 0.1 | 5.4 ± 0.5 | 1 | 0 |
| oxotremorine | 7.02 ± 0.04 | 22 ± 2 | 6.4 ± 0.1 | 3.0 ± 0.3 | 4.14 ± 0.41 | −0.62 ± 0.06 |
| pilocarpine | 5.88 ± 0.04 | 18 ± 2 | 5.5 ± 0.1 | 1.5 ± 0.1 | 0.238 ± 0.025 | 0.62 ± 0.06 |
| 6A | 5.3 ± 0.1 | 2.4 ± 0.2 | 5.3 ± 0.2 | 0.05 ± 0.01 | 0.0056 ± 0.0008 | 2.26 ± 0.48 |
| 7A | 5.4 ± 0.1 | 2.6 ± 0.3 | 5.4 ± 0.1 | 0.06 ± 0.01 | 0.0084 ± 0.0011 | 2.08 ± 0.34 |

| $M_3G_s$ | | $E_{MAX} = 3.9 \pm 0.3$ [fold increase] | | | | |
|---|---|---|---|---|---|---|
| ($\uparrow$cAMP) | $pEC_{50}$ | $E'_{MAX}$ | $pK_A$ | $\tau$ | RAi | $\Delta\log(\tau/K_A)$ |
| carbachol | 4.90 ± 0.05 | 2.0 ± 0.1 | 4.7 ± 0.1 | 0.57 ± 0.06 | 1 | 0 |
| oxotremorine | 5.58 ± 0.05 | 1.9 ± 0.1 | 5.4 ± 0.1 | 0.48 ± 0.05 | 4.23 ± 0.28 | −0.63 ± 0.06 |
| pilocarpine | 4.73 ± 0.05 | 1.46 ± 0.05 | 4.7 ± 0.1 | 0.19 ± 0.02 | 0.299 ± 0.18 | 0.524 ± 0.055 |
| 6A | n.d. | n.d. | n.c. | n.c. | 0 | n.c. |
| 7A | n.d. | n.d. | n.c. | n.c. | 0 | n.c. |

| $M_4G_i$ | | $E_{MAX} = 89 \pm 2$ [% inhibition] | | | | |
|---|---|---|---|---|---|---|
| ($\downarrow$cAMP) | $pEC_{50}$ | $E'_{MAX}$ | $pK_A$ | $\tau$ | RAi | $\Delta\log(\tau/K_A)$ |
| carbachol | 7.20 ± 0.04 | 55 ± 2 | 6.8 ± 0.1 | 1.4 ± 0.1 | 1 | 0 |
| oxotremorine | 7.85 ± 0.04 | 48 ± 2 | 7.5 ± 0.1 | 1.2 ± 0.1 | 3.81 ± 0.16 | −0.62 ± 0.08 |
| pilocarpine | 7.04 ± 0.04 | 36 ± 1 | 6.8 ± 0.1 | 0.68 ± 0.06 | 0.395 ± 0.010 | 0.32 ± 0.03 |
| 6A | 5.07 ± 0.07 | 25 ± 2 | 4.9 ± 0.1 | 0.39 ± 0.04 | 0.0046 ± 0.0004 | 2.15 ± 0.16 |
| 7A | 5.75 ± 0.05 | 39 ± 2 | 5.5 ± 0.1 | 0.78 ± 0.08 | 0.0209 ± 0.0011 | 1.58 ± 0.22 |

| $M_4G_q$ | | $E_{MAX} = 5.1 \pm 0.5$ [fold over basal] | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 5.99 ± 0.05 | 1.78 ± 0.05 | 5.9 ± 0.1 | 0.24 ± 0.03 | 1 | 0 |
| oxotremorine | 6.79 ± 0.05 | 1.58 ± 0.04 | 6.7 ± 0.1 | 0.17 ± 0.02 | 4.69 ± 0.17 | −0.67 ± 0.06 |
| pilocarpine | 5.80 ± 0.05 | 1.15 ± 0.03 | 5.8 ± 0.1 | 0.04 ± 0.01 | 0.124 ± 0.014 | 0.91 ± 0.08 |
| 6A | n.d. | n.d. | n.c. | n.c. | 0 | n.c. |
| 7A | n.d. | n.d. | n.c. | n.c. | 0 | n.c. |

| $M_4 G_q + G_{15}$ | | $E_{MAX} = 5.2 \pm 0.4$ [fold over basal] | | | | |
|---|---|---|---|---|---|---|
| ($\uparrow IP_X$) | $pEC_{50}$ | $E'_{MAX}$ | $pK_A$ | $\tau$ | RAi | $\Delta\log(\tau/K_A)$ |
| carbachol | 6.72 ± 0.05 | 4.5 ± 0.3 | 6.0 ± 0.1 | 4.8 ± 0.5 | 1 | 0 |
| oxotremorine | 7.33 ± 0.05 | 4.0 ± 0.3 | 6.8 ± 0.1 | 2.5 ± 0.2 | 3.50 ± 0.33 | −0.54 |
| pilocarpine | 6.05 ± 0.05 | 2.9 ± 0.2 | 5.8 ± 0.1 | 0.8 ± 0.1 | 0.117 ± 0.015 | 0.934 |
| 6A | n.d. | n.d. | n.c. | n.c. | 0 | n.c. |
| 7A | n.d. | n.d. | n.c. | n.c. | 0 | n.c. |

| $M_4G_s$ | | $E_{MAX} = 3.9 \pm 0.3$ [fold increase] | | | | |
|---|---|---|---|---|---|---|
| ($\uparrow$cAMP) | $pEC_{50}$ | $E'_{MAX}$ | $pK_A$ | $\tau$ | RAi | $\Delta\log(\tau/K_A)$ |

TABLE 8-continued

Parameters of functional responses. Parameters of functional responses (cAMP and $IP_X$) upon stimulation of carbachol, oxotremorine, pilocarpine or compound 6A or 7A.

| | | | | | | |
|---|---|---|---|---|---|---|
| carbachol | 4.94 ± 0.04 | 2.9 ± 0.2 | 4.5 ± 0.1 | 1.9 ± 0.2 | 1 | 0 |
| oxotremorine | 5.56 ± 0.04 | 2.6 ± 0.2 | 5.2 ± 0.1 | 1.3 ± 0.1 | 3.58 ± 0.31 | −0.55 ± 0.06 |
| pilocarpine | 4.57 ± 0.05 | 1.67 ± 0.06 | 4.5 ± 0.1 | 0.30 ± 0.04 | 0.150 ± 0.17 | 0.82 ± 0.06 |
| 6A | n.d. | n.d. | n.c. | n.c. | 0 | n.c. |
| 7A | n.d. | n.d. | n.c. | n.c. | 0 | n.c. |

| $M_5G_i$ | $E_{MAX}$ = 92 ± 2 [% of inhibition] | | | | | |
|---|---|---|---|---|---|---|
| (↓cAMP) | $pEC_{50}$ | $E'_{MAX}$ | $pK_A$ | τ | RAi | $\Delta\log(\tau/K_A)$ |
| carbachol | 6.45 ± 0.05 | 18 ± 1 | 6.4 ± 0.1 | 0.24 ± 0.03 | 1 | 0 |
| oxotremorine | 7.15 ± 0.05 | 22 ± 2 | 7.0 ± 0.1 | 0.31 ± 0.03 | 6.44 ± 0.67 | −0.79 ± 0.06 |
| pilocarpine | 6.50 ± 0.06 | 12 ± 1 | 6.4 ± 0.1 | 0.15 ± 0.02 | 0.697 ± 0.080 | 0.126 ± 0.04 |
| 6A | 4.66 ± 0.07 | 22 ± 2 | 4.5 ± 0.1 | 0.31 ± 0.04 | 0.021 ± 0.002 | 1.70 ± 0.21 |
| 7A | 4.50 ± 0.07 | 34 ± 2 | 4.3 ± 0.1 | 0.59 ± 0.02 | 0.026 ± 0.003 | 1.67 ± 0.18 |

| $M_5G_q$ | $E_{MAX}$ = 22 ± 2 [fold over basal] | | | | | |
|---|---|---|---|---|---|---|
| (↑$IP_X$) | $pEC_{50}$ | $E'_{MAX}$ | $pK_A$ | τ | RAi | $\Delta\log(\tau/K_A)$ |
| carbachol | 6.45 ± 0.05 | 17 ± 2 | 5.8 ± 0.1 | 3.1 ± 0.4 | 1 | 0 |
| oxotremorine | 7.13 ± 0.04 | 16 ± 1 | 6.6 ± 0.1 | 2.2 ± 0.3 | 4.37 ± 0.29 | −0.64 |
| pilocarpine | 5.975 ± 0.04 | 12 ± 1 | 5.7 ± 0.1 | 1.0 ± 0.1 | 0.205 ± 0.023 | 0.69 |
| 6A | 5.8 ± 0.1 | 1.16 ± 0.04 | n.c. | n.c. | 0.0023 ± 0.0007 | n.c. |
| 7A | 5.1 ± 0.1 | 1.26 ± 0.05 | n.c. | n.c. | 0.0006 ± 0.0002 | n.c. |

| $M_5G_q + G_{15}$ | $E_{MAX}$ = 21 ± 2 [fold over basal] | | | | | |
|---|---|---|---|---|---|---|
| (↑$IP_X$) | $pEC_{50}$ | $E'_{MAX}$ | $pK_A$ | τ | RAi | $\Delta\log(\tau/K_A)$ |
| carbachol | 6.49 ± 0.04 | 17 ± 2 | 5.8 ± 0.1 | 4.0 ± 0.4 | 1 | 0 |
| oxotremorine | 7.15 ± 0.04 | 16 ± 1 | 6.6 ± 0.1 | 2.6 ± 0.3 | 4.12 ± 0.26 | −0.62 ± 0.07 |
| pilocarpine | 5.97 ± 0.04 | 12 ± 1 | 5.7 ± 0.1 | 1.1 ± 0.1 | 0.191 ± 0.017 | 0.71 ± 0.05 |
| 6A | 5.8 ± 0.1 | 1.19 ± 0.04 | 5.8 ± 0.1 | 0.009 ± 0.003 | 0.0025 ± 0.0008 | 2.60 ± 0.82 |
| 7A | 5.1 ± 0.1 | 1.28 ± 0.05 | 5.7 ± 0.1 | 0.014 ± 0.003 | 0.0007 ± 0.0002 | 3.17 ± 0.88 |

| $M_5G_s$ | $E_{MAX}$ = 3.5 ± 0.3 [fold increase] | | | | | |
|---|---|---|---|---|---|---|
| (↑cAMP) | $pEC_{50}$ | $E'_{MAX}$ | $pK_A$ | τ | RAi | $\Delta\log(\tau/K_A)$ |
| carbachol | 4.58 ± 0.06 | 1.23 ± 0.03 | 4.5 ± 0.1 | 0.10 ± 0.02 | 1 | 0 |
| oxotremorine | 5.42 ± 0.06 | 1.22 ± 0.03 | 5.4 ± 0.1 | 0.09 ± 0.02 | 6.62 ± 0.58 | −0.82 ± 0.08 |
| pilocarpine | 4.4 ± 0.2 | 1.11 ± 0.05 | n.c. | n.c. | 0.288 ± 0.049 | 0.540 ± 0.06 |
| 6A | n.d. | n.d. | n.c. | n.c. | 0 | n.c. |
| 7A | n.d. | n.d. | n.c. | n.c | 0 | n.c. | n.c., not calculated;
n.d., not determined.
Parameters of non-preferential functional responses are listed.
Half-efficient concentration ($EC_{50}$) is expressed as negative logarithm and apparent maximal response to agonist ($E'_{MAX}$) is expressed as folds over basal (increase in $IP_X$ level – $G_q$), % of inhibition (decrease in cAMP level – $G_i$) and fold increase (increase in cAMP level – $G_s$).
Hill coefficients are equal to one.
Values are means ± SD from 5 independent experiments performed in triplicates.

TABLE 9

Expression levels of muscarinic receptors in tissues. Binding of 2 nM [$^3$H]NMS to membranes prepared from rat tissues is expressed in pmol per mg of membrane protein.

| Tissue | 2 nM [$^3$H]NMS binding [pmol/mg] |
|---|---|
| brain cortex | 0.52 ± 0.08 |
| cerebellum | 0.48 ± 0.08 |
| striatum | 0.58 ± 0.08 |
| submaxillary gland | 0.18 ± 0.04 |
| ventral tegmental area (VTA) | 0.38 ± 0.07 |

Values are means ± SD from 5 independent determinations performed in triplicates.

Synthesis:

(thiophen-2-yl)methanol (2A)

Procedure was the same as 2B. Reagents used: 1.50 g of sodium methylate, 3.0 g of sodium borohydride, 12.0 g of thiophene carboxaldehyde (0.107 mol), 75 mL of methanol. 11.0 g recovered (90.16%). $^1$H-NMR (300 MHz, $CDCl_3$) δ 7.3 (1H, d), 7.0 (2H, m), 4.8 (2H, s), 2.2 (1H, bs).

2-(chloromethyl)thiophene (3A)

Procedure was the same as 3B. Reagents used: 9.5 g (0.083 mol) of 2A, 25.32 g (0.0966 mol) of triphenyl phosphine, 60 mL of anhydrous carbon tetrachloride. 7.0 g recovered (63.64%). $^1$H-NMR (300 MHz, $CD_3Cl_3$) δ 7.75 (1H, d), 7.5 (2H, m), 4.8 (2H, s).

1-[(thiophen-2-yl)methyl]pyridin-1-ium chloride (4A)

Procedure was the same as 4B. Reagents used: 7.0 g of 3A (0.0528 mol), 4.43 g (0.0528 mol) of pyridine, 20 mL of acetonitrile. 8.72 g recovered (78%). $^1$H-NMR (300 MHz, D$_2$O) δ 8.8 (2H, d), 8.4 (1H, t), 7.9 (2H, t), 7.4 (1H, d), 7.2 (1H, dd), 7.0 (1H, d), 5.9 (2H, s).

1-[(thiophen-2-yl)methyl]-1,2,3,6-tetrahydropyridine (5A)

Procedure was the same as 5B. Reagents used: 6.4 g of 4A (0.0302 mol) in 50 mL of methanol, 5.71 g sodium borohydride (0.151 mol), 75 mL of 0.1 N sodium hydroxide. 4.78 g recovered (88.51%). $^1$H-NMR (300 MHz, CDCl$_3$) δ 7.2 (1H, d), 6.9-7.0 (2H, m), 5.8 (1H, m), 5.7 (1H, m), 3.8 (2H, s), 3.0 (2H, m), 2.6 (2H, t), 2.2 (2H, m).

1-[(thiophen-2-yl)methyl]-1,2,3,6-tetrahydropyridin-1-ium chloride (6A)

Procedure was the same as 6B. Reagents used: 1.0 g of 5A (0.0056 mol) in 10 mL of methylene chloride, excess HCl gas. 0.51 g recovered (42.5%) after recrystallization from n-butanol, m.p. 193.5-194.4° C. $^1$H-NMR (300 MHz, D$_2$O) δ 7.5 (1H, d), 7.2 (1H, d), 7.0 (1H, dd), 5.8 (1H, m), 5.55 (1H, m), 4.45 (2H, s), 3.6 (2H, m), 3.5 (1H, m), 3.1 (1H, m), 2.3 (2H, m). Anal. Calcd. For C$_{10}$H$_{14}$NSCl: C, 55.70%, H, 6.5%, N, 6.5%, S, 14.85%, Cl, 16.45%. Found: C, 55.52%, H, 6.42%, N, 6.14%, S, 14.33%, Cl, 16.50%.

1-methyl-1-[(thiophen-2-yl)methyl]-1,2,3,6-tetrahydropyridin-1-ium iodide (7A)

Procedure was the same as 7B. Reagents used: 1.0 mL of methyl iodide, 1.0 g of 5A (0.0056 mol), 2.0 mL acetonitrile. 0.92 g (51.4%) recovered after recrystallization from n-butanol, m.p. 129-130° C. $^1$H-NMR (300 MHz, D$_2$O) δ 7.6 (1H, d), 7.3 (1H, d), 7.1 (1H, dd), 5.9 (1H, m), 5.6 (1H, m), 4.6 (2H, s), 3.9 (1H, m), 3.6 (1H, m), 3.4 (2H, m), 2.9 (3H, s), 2.4 (2H, m). Anal. Calcd. For C$_{11}$H$_{16}$NSI: C, 41.13%, H, 4.99%, N, 4.36%, S, 9.97%, I, 39.55%. Found: C, 41.16%, H, 4.94%, N, 4.16%, S, 9.20%, I, 39.59%.

(5-methylthiophen-2-yl)methanol (2B)

A solution containing 1.50 g of sodium methylate, 3.0 g of sodium borohydride and 25 ml of methanol was slowly added to a mixture containing 13.5 g (0.107 mol) of 5-methyl thiophenecarboxaldehyde and 50.0 mL of methanol with stirring and cooling. The reaction mixture was acidified over crushed ice with 6 M HCl. The mixture was then extracted with anhydrous ether several times, combined ether extracts were dried over anhydrous magnesium sulfate, filtered and concentrated to afford 4.6 g (33.6%). $^1$H-NMR (300 MHz, CD$_3$COCD$_3$) δ 6.7 (1H, d), 6.6 (1H, d), 4.6 (2H, s), 4.4 (1H, bs), 2.4 (3H, s).

2-(chloromethyl)-5-methylthiophene (3B)

A mixture containing 2.3 g of 2B (0.018 mol), 13 ml of anhydrous CCl$_4$ and 5.47 g of triphenylphosphine (0.021 mol) was refluxed for over one hour. After cooling, 100 mL of anhydrous pentane was added and the reaction mixture was filtered, residue washed with another 100 mL of anhydrous pentane. The combined pentane extracts was concentrated and distilled under vacuum to afford 1.44 g (54.75%) at 800/15 mm Hg. $^1$H-NMR (300 MHz, CD$_3$COCD$_3$) δ 7.0 (1H, d), 6.7 (1H, d), 4.9 (2H, s), 2.5 (3H, s).

1-[(5-methylthiophen-2-yl)methyl]pyridin-1-ium chloride (4B)

A mixture containing 1.44 g of 3B (0.010 mol), 0.84 g of pyridine (0.010 mol) and 5.0 mL of acetonitrile was stirred overnight at room temperature. The solution was concentrated to afford 1.92 g (86.88%). $^1$H-NMR (300 MHz, D$_2$O) δ 8.8 (2H, d), 8.4 (1H, t), 7.9 (2H, t), 7.0 (1H, d), 6.65 (1H, d), 5.8 (2H, s), 2.35 (3H, s).

1-[(5-methylthiophen-2-yl)methyl]-1,2,3,6-tetrahydropyridine (5B)

A solution containing 0.38 g (0.010 mol) of sodium borohydride and 17.0 mL of 0.10 N NaOH was slowly added to another solution of 1.92 g (0.00852 mol) of 4B in 12.0 mL of methanol with stirring and cooling. After 30 minutes of additional stirring and cooling, the solution was acidified with 6 M HCl and pH was readjusted to 7-8 with 1M NaOH. The solution was then extracted three times with CH$_2$Cl$_2$ and all organic extracts were combined, dried over anhydrous MgSO$_4$, filtered and concentrated to yield 1.50 g (92.0%). $^1$H-NMR (300 MHz, CDCl$_3$) δ 6.75 (1H, d), 6.6 (1H, d), 5.8 (1H, m), 5.7 (1H, m), 3.8 (2H, s), 3.0 (2H, d), 2.6 (2H, d), 2.45 (3H, s), 2.2 (2H, m).

1-[(5-methylthiophen-2-yl)methyl]-1,2,3,6-tetrahydropyridin-1-ium chloride (6B)

Excess hydrogen chloride gas was passed through a solution containing 0.75 g (0.00389 mol) of 5B dissolved in 9 mL of acetonitrile. The solution was stirred overnight at room temperature, concentrated and the residue was recrystallized from n-butanol/ether to yield 0.645 g (72.39%), m.p. 175-176° C. $^1$H-NMR (300 MHz, D$_2$O) δ 6.95 (1H, d), 6.7 (1H, d), 5.8 (1H, m), 5.55 (1H, m), 4.35 (2H, s), 3.6-3.4 (3H, m), 3.05 (1H, m), 2.35 (3H, s), 2.25 (2H, m). Anal. Calcd. For C$_{11}$H$_{16}$NSCl: C, 57.51%, H, 6.97%, N, 6.10%, S, 13.97%, Cl, 15.45%. Found: C, 57.08%, H, 7.12%, N, 5.83%, S, 14.10%, Cl, 15.92%. 1-methyl-1-[(5-methylthiophen-2-yl)methyl]-1,2,3,6-tetrahydropyridin-1-ium iodide (7B) Excess iodomethane was added to a solution containing 0.75 g (0.00389 mol) of 5B dissolved in 9 mL of acetonitrile. The solution was stirred overnight at room temperature, concentrated and the residue was recrystallized from n-butanol to yield 0.50 g (38.46%), m.p. 159-160° C. $^1$H-NMR (300 MHz, D$_2$O) δ 7.1 (1H, d), 6.75 (1H, d), 5.9 (1H, m), 5.6 (1H, m), 4.5 (2H, s), 3.95-3.85 (1H, m), 3.65 (1H, m), 3.4-3.3 (2H, m), 2.9 (3H, s), 2.4 (2H, m), 2.35 (3H, s). Anal. Calcd. For C$_{12}$H$_{18}$NSI: C, 42.99%, H, 5.37%, N, 4.18%, S, 9.57%, I, 37.89%. Found: C, 43.57%, H, 5.42%, N, 4.17%, S, 9.21%, I, 39.51%.

(5-bromothiophen-2-yl)methanol (2C)

A solution containing 1.06 g (0.020 mol) sodium methylate, 2.15 g (0.0573 mol) of sodium borohydride and 25 ml of methanol was slowly added to a mixture containing 9.57 g (0.0535 mol) of 5-bromo thiophenecarboxaldehyde and 30.0 mL of methanol with stirring and cooling. The reaction mixture was acidified over crushed ice with 6 M HCl. The mixture was then extracted with anhydrous ether several times, combined ether extracts dried over anhydrous magnesium sulfate, filtered and concentrated to afford 6.5 g (67.15%). $^1$H-NMR (300 MHz, CDCl$_3$) δ 6.9 (1H, d), 6.8 (1H, d), 4.6 (2H, s), 2.0 (1H, bs).

2-bromo-5-(chloromethyl)thiophene (3C)

Procedure same as 3B. Reagents used: 6.55 g (0.0362 mol) of 2C, 10.94 g (0.042 mol) of triphenyl phosphine, 25 mL of anhydrous carbon tetrachloride. About 4.67 g recovered (64.7%). The crude product was distilled under vacuum to afford 2.17 g of pure 3C (30.1%), b.p. 70° C./10 mm Hg. $^1$H-NMR (300 MHz, CD$_3$Cl$_3$) δ 6.9 (1H, d), 6.8 (1H, d), 4.7 (2H, s).

1-[(5-bromothiophen-2-yl)methyl]pyridin-1-ium chloride (4C)

Procedure same as 4B. Reagents used: 2.17 g of 3C (0.0109 mol), 0.84 g (0.010 mol) of pyridine, 5 mL of acetonitrile. 2.30 g (72.7%) recovered. $^1$H-NMR (300 MHz, D$_2$O) δ 9.8 (2H, d), 8.4 (2H, t), 7.9 (1H, t), 7.0 (1H, d), 6.9 (1H, d), 5.8 (2H, s).

1-[(5-bromothiophen-2-yl)methyl]-1,2,3,6-tetrahydropyridine (5C)

Procedure was same as 5B. Reagents used: 2.0 g of 4C (0.0069 mol) in 10 mL of methanol, 0.40 g sodium borohydride (0.0105 mol), 14 mL of 0.1 N sodium hydroxide. 1.36 g recovered (76.8%). $^1$H-NMR (300 MHz, CDCl$_3$) δ 6.9 (1H, d), 6.7 (1H, d), 5.8 (1H, m), 5.65 (1H, m), 3.75 (2H, s), 3.0 (2H, d), 2.6 (2H, t), 2.2 (2H, m).

1-[(5-bromothiophen-2-yl)methyl]-1,2,3,6-tetrahydropyridin-1-ium chloride (6C)

Procedure same as 6B. Reagents used: 0.55 g of 5C (0.00213 mol) in 10 mL of acetonitrile, excess HCl gas. 0.30 g recovered (47.6%) after recrystallization from n-butanol, m.p. 205.3-206.5° C. $^1$H-NMR (300 MHz, D$_2$O) δ 7.05 (1H, d), 6.95 (1H, d), 5.9-5.8 (1H, m), 5.55 (1H, m), 4.4 (2H, m), 3.4-3.6 (3H, m), 3.1 (1H, m), 2.3 (2H, m). Anal. Calcd. For C$_{10}$H$_{13}$NSBrCl: C, 40.79%, H, 4.41%, N, 4.75%, S, 10.87%. Found: C, 40.70%, H, 4.53%, N, 4.88%, S, 9.79.

1-[(5-bromothiophen-2-yl)methyl]-1-methyl-1,2,3,6-tetrahydropyridin-1-ium iodide (7C)

Procedure same as 7B. Reagents used: 1.0 mL of methyl iodide, 0.80 g of 5C (0.0031 mol), 1.5 mL acetonitrile. 0.90 g (72.58%) recovered after recrystallization from n-butanol, m.p. 151-152.3° C. $^1$H-NMR (300 MHz, D$_2$O) δ 7.1 (1H, d), 7.05 (1H, d), 5.9 (1H, m), 5.6 (1H, m), 4.6 (2H, s), 3.9-3.8 (1H, m), 3.7-3.6 (1H, m), 3.4-3.3 (2H, m), 2.9 (3H, s), 2.4 (2H, m). Anal. Calcd. For C$_{11}$H$_{15}$NBrSI: C, 33.04%, H, 3.75%, N, 3.50%, S, 8.00%. Found: C, 33.4%, H, 3.82%, N, 3.62%, S, 7.02%.

(5-chlorothiophen-2-yl)methanol (2D)

0.821 g (0.022 mol) of sodium borohydride dissolved in 30 mL of 0.1N NaOH was slowly added to a mixture containing 2.8 g (0.0191 mol) of 5-chloro thiophenecarboxaldehyde and 10.0 mL of methanol with stirring and cooling. The reaction mixture was acidified over crushed ice with 6 M HCl. The mixture was then extracted with anhydrous ether several times, combined ether extracts dried over anhydrous magnesium sulfate, filtered and concentrated to afford 1.87 g (65.9%). $^1$H-NMR (300 MHz, CDCl$_3$) δ 7.0 (1H, d), 6.9 (1H, d), 4.7 (2H, s), 2.2 (1H, bs).

2-chloro-5-(chloromethyl)thiophene (3D)

Procedure was the same as 3B. Reagents used: 1.85 g (0.0126 mol) of 2D, 3.83 g (0.0146 mol) of triphenyl phosphine, 10 mL of anhydrous carbon tetrachloride to afford 1.53 g (72.8%). $^1$H-NMR (300 MHz, CD$_3$Cl$_3$) δ 6.85 (1H, d), 6.78 (1H, d), 4.7 (2H, s).

1-[(5-chlorothiophen-2-yl)methyl]pyridin-1-ium chloride (4D)

Procedure was the same as 4B. Reagents used: 1.50 g of 3D (0.0090 mol), 0.62 g (0.009 mol) of pyridine, 5 mL of acetonitrile. 1.2 g (54.3%) recovered. $^1$H-NMR (300 MHz, D$_2$O) δ 8.75 (1H, t), 8.4 (2H, t), 7.9 (2H, t), 7.06 (1H, d), 6.85 (1H, d), 5.75 (2H, s).

1-[(5-chlorothiophen-2-yl)methyl]-1,2,3,6-tetrahydropyridine (5D)

Procedure was the same as 5B. Reagents used: 1.2 g of 4D (0.0049 mol) in 6 mL of methanol, 0.282 g sodium borohydride (0.00744 mol) in 8 mL of 0.1 N sodium hydroxide. 0.87 g recovered (83.5%). $^1$H-NMR (300 MHz, CDCl$_3$) δ 6.75 (1H, d), 6.7 (1H, d), 5.75 (1H, m), 5.65 (1H, m), 3.7 (2H, s), 3.0 (2H, m), 2.6 (2H, t), 2.2 (2H, m).

1-[(5-chlorothiophen-2-yl)methyl]-1-methyl-1,2,3,6-tetrahydropyridin-1-ium iodide (7D)

Procedure was the same as 7B. Reagents used: 1.0 mL of methyl iodide, 0.40 g of 5D (0.00187 mol), 2 mL acetonitrile. 0.56 g (83.6%) recovered after recrystallization from n-butanol, m.p. 153.4-155.2° C. $^1$H-NMR (300 MHz, D$_2$O) δ 7.1 (1H, d), 6.9 (1H, d), 5.9 (1H, m), 5.6 (1H, m), 4.55 (2H, s), 3.95-3.8 (1H, m), 3.7-3.6 (1H, m), 3.4-33 (2H, m), 2.95 (3H, s), 2.45 (2H, m). Anal. Calcd. For C$_{11}$H$_{15}$NSICl: C, 37.17%, H, 4.22%, N, 3.94%, S, 9.00%. Found: C, 37.57%, H, 4.27%, N, 3.84%, S, 9.21%.

(4-methylthiophen-2-yl)methanol (2E)

Same procedure as 2B. Reagents used: 0.2284 g of sodium methylate, 0.45 g of sodium borohydride, 2.10 g of 4-methylthiophene carboxaldehyde (0.017 mol), 25 mL of methanol. 2.03 g of recovered (96.3%). $^1$H-NMR (300 MHz, CDCl$_3$) δ 6.85 (1H, s), 6.90 (1H, s), 4.65 (2H, s), 2.25 (3H, s). 2-(chloromethyl)-4-methylthiophene (3E) Procedure was the same as 3B. Reagents used: 2.00 g (0.0156 mol) of 2E, 4.01 g (0.0153 mol) of triphenyl phosphine, 12 mL of anhydrous carbon tetrachloride. 2.0 g recovered (87.3%). $^1$H-NMR (300 MHz, CD$_3$Cl$_3$) δ 7.1 (1H, s), 7.0 (1H, s), 4.9 (2H, s), 2.2 (3H, s).

1-[(4-methylthiophen-2-yl)methyl]pyridin-1-ium chloride (4E)

Procedure was the same as 4B. Reagents used: 2.0 g of 3E (0.0137 mol), 1.08 g (0.0137 mol) of pyridine, 5 mL of acetonitrile. 1.23 g recovered (39.8%). $^1$H-NMR (300 MHz, D$_2$O) δ 9.8 (2H, d), 8.4 (1H, t), 7.95 (2H, m), 7.1 (1H, s), 7.05 (1H, s), 5.8 (2H, s), 2.1 (3H, s).

1-[(4-methylthiophen-2-yl)methyl]-1,2,3,6-tetrahydropyridine (5E)

Procedure was the same as 5B. Reagents used: 1.2 g of 4E (0.0053 mol) in 7 mL of methanol, 0.218 g sodium borohydride (0.00576 mol), 10 mL of 0.1 N sodium hydroxide. 0.50 g recovered (49.0%). $^1$H-NMR (300 MHz, CD$_3$COCD$_3$) δ 6.4 (1H, s), 6.3 (1H, s), 5.7 (1H, m), 5.65 (1H, m), 3.7 (2H, s), 2.95 (2H, m), 2.85 (2H, t), 2.55 (2H, t), 2.2 (3H, s).

1-[(4-methylthiophen-2-yl)methyl]-1,2,3,6-tetrahydropyridin-1-ium chloride (6E)

Excess hydrogen chloride gas was passed through a solution containing 0.25 g (0.0013 mol) of 5E dissolved in 2 mL of dichloromethane. The solution was stirred overnight at room temperature, concentrated and the residue was recrystallized from n-butanol to yield 0.20 g (68.9%), m.p. 149-152° C. $^1$H-NMR (300 MHz, D$_2$O) δ 7.06 (1H, s), 7.05 (1H, s), 5.9-5.8 (1H, m), 5.6-5.5 (1H, m), 4.4 (2H, s), 3.6-3.40 (3H, m), 3.1-3.0 (1H, m), 2.3 (2H, m), 2.1 (3H, s). Anal. Calcd. For C$_{11}$H$_{16}$NSCl: C, 57.51%, H, 6.97%, N, 6.10%, S, 13.97%. Found: C, 56.27%, H, 6.76%, N, 5.79%, S, 13.17%.

Other Embodiments

Any improvement may be made in part or all of the muscarinic agonists, compositions, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A composition comprising a pharmaceutically acceptable carrier and a muscarinic agonist having the formula:

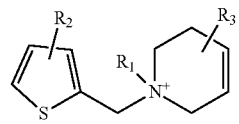

or a pharmaceutically acceptable salt thereof, wherein:
R$_1$=H or Me;
R$_2$=H, Me, Et, OMe, OEt, F, Cl, Br, I, or NO$_2$; and
R$_3$=H, Me, Et, OMe or CO$_2$Me, wherein R$_3$ may be bonded to any carbon of the 6-membered ring,
in a therapeutically effective amount for selectively activating at least one of: muscarinic receptor M$_2$ and muscarinic receptor M$_4$, and selectively activating Gi/o signaling in a subject.

2. The composition of claim 1, wherein R$_1$, R$_2$, and R$_3$=H and the muscarinic agonist has the formula:

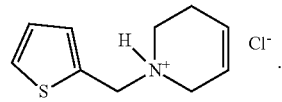 [SMILES: C1=CC[NH+](Cc2cccs2)CC1 ; [Cl-]]

3. The composition of claim 1, wherein R$_1$=Me, and R$_2$, and R$_3$=H, and the muscarinic agonist has the formula:

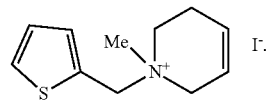

4. The composition of claim 1, wherein the therapeutically effective amount is from about 1 mg to about 1000 mg.

5. The composition of claim 1, wherein the composition is formulated for oral or parenteral administration.

* * * * *